US009895125B2

(12) United States Patent
Besson

(10) Patent No.: US 9,895,125 B2
(45) Date of Patent: Feb. 20, 2018

(54) MULTI-SOURCE CT SYSTEMS AND PRE-RECONSTRUCTION INVERSION METHODS

(71) Applicant: Guy M. Besson, Broomfield, CO (US)

(72) Inventor: Guy M. Besson, Broomfield, CO (US)

( * ) Notice: Subject to any disclaimer, the term of this patent is extended or adjusted under 35 U.S.C. 154(b) by 175 days.

(21) Appl. No.: 14/946,626

(22) Filed: Nov. 19, 2015

(65) Prior Publication Data

US 2016/0166223 A1   Jun. 16, 2016

Related U.S. Application Data

(60) Provisional application No. 62/081,858, filed on Nov. 19, 2014, provisional application No. 62/118,591, (Continued)

(51) Int. Cl.
*A61B 6/00* (2006.01)
*A61B 6/03* (2006.01)

(52) U.S. Cl.
CPC ............ *A61B 6/5205* (2013.01); *A61B 6/032* (2013.01); *A61B 6/4007* (2013.01); *A61B 6/4435* (2013.01); *A61B 6/54* (2013.01)

(58) Field of Classification Search
CPC ............................ A61B 6/4014; A61B 6/4007
See application file for complete search history.

(56) References Cited

U.S. PATENT DOCUMENTS

| 4,150,293 A | 4/1979 | Franke |
| 5,841,141 A | 11/1998 | Gullberg et al. |

(Continued)

FOREIGN PATENT DOCUMENTS

WO   2014028930 A1   2/2014

OTHER PUBLICATIONS

International Search Report and Written Opinion corresponding to International Patent Application No. PCT/US2015/061679; dated Mar. 29, 2016; 14 pages.

(Continued)

*Primary Examiner* — Hoon Song
(74) *Attorney, Agent, or Firm* — Lathrop Gage LLP

(57) ABSTRACT

A computed tomography scanner has multiple radiation sources or source arrays, in specific geometric dimensions for optimized imaging speed. A CT system with maximum fan-angle $\Gamma$ and K simultaneously active x-ray sources distributed over an angle of $\pi-2\Gamma$ radians, the sources partially overlapping on a detector array, measures summed projection data corresponding to K or less line-integrals at each detector element. When the CT machine's dimensions $R_M$, $R_d$, and $R_S$, corresponding respectively to the measurement field-of-view, detector distance from iso-center, and source distance from iso-center, are such that projections of the two extreme radiation sources do not overlap on the detector, the individual line-integrals can be recovered by inversion of linear systems comprising K or less rows in fewer unknown than rows; the unknowns given by the exponential of the negative of the line integrals to be recovered. The CT scanner then reconstructs an image from the line-integral estimates.

50 Claims, 42 Drawing Sheets

Related U.S. Application Data filed on Feb. 20, 2015, provisional application No. 62/186,991, filed on Jun. 30, 2015.

(56) References Cited

U.S. PATENT DOCUMENTS

| | | |
|---|---|---|
| 6,973,158 B2 | 12/2005 | Besson |
| 8,755,493 B2 | 6/2014 | Travish et al. |
| 2006/0233295 A1 | 10/2006 | Edic et al. |
| 2008/0049891 A1 | 2/2008 | Yin et al. |
| 2008/0317197 A1* | 12/2008 | Matsuzaki ............ G01T 1/1615 378/9 |
| 2009/0101838 A1 | 4/2009 | Boyden et al. |
| 2010/0135454 A1 | 6/2010 | Noo |
| 2010/0322498 A1 | 12/2010 | Wieczorek et al. |
| 2013/0121553 A1 | 5/2013 | Thibault et al. |
| 2013/0251097 A1 | 8/2013 | Zou |
| 2014/0241489 A1 | 8/2014 | Zhang et al. |
| 2015/0366522 A1 | 12/2015 | Besson |

OTHER PUBLICATIONS

Besson, G. M.; New CT system architectures for high temporal resolution with applications to improved geometric dose efficiency and cardiac imaging; Medical Physics 42, 2668-2678 (May 2015).

Besson, G.M.; Old Ideas New Again: A System Concept for Fast CT Using Semi-Conventional Approaches; The third international conference on image formation in X-ray computed tomography; pp. 303-306.

Besson, G.M.; A new CT system architecture for high temporal resolution with applications to improved geometric dose efficiency and sparse sampling; Medical Imaging 2015: Physics of Medical Imaging, edited by Christoph Hoeschen, Despina Kontos, Proc. of SPIE vol. 9412; pp. 94120Y-1-94120Y-11.

\* cited by examiner

MULTI-SOURCE CT SYSTEMS AND PRE-RECONSTRUCTION INVERSION METHODS

CLAIM OF PRIORITY

The present document claims priority to U.S. Provisional Patent Application 62/081,858 filed 19 Nov. 2014. The present document also claims priority to U.S. Provisional Patent Application 62/118,591 filed 20 Feb. 2015. The present document also claims priority to U.S. Provisional Patent Application 62/186,991 filed 30 Jun. 2015. The contents of the aforementioned patent applications are incorporated herein by reference.

FIELD OF THE INVENTION

This disclosure relates to the field of electromagnetic (EM) radiation imaging systems, and more particularly to the use of multi-source simultaneous radiation exposure in computed tomography (CT) imaging systems. In particular, the disclosure addresses methods, algorithms and systems for x-ray radiation CT imaging using simultaneous exposure from two or more radiation sources, although it is not limited to the imaging of radiation sources in the x-ray energy range.

BACKGROUND

X-ray projection imaging or CT imaging provides a number of benefits, as is known in the art. CT requires acquiring projections or views from a multiplicity of angles around the object from which a tomographic image of structures within the object or patient is derived.

Since the beginning of CT, cardiac imaging has been a key technology driver. Multiple innovations have attempted to address high temporal resolution needed. Although current CT systems can image a cross-section of the heart in about 100 milliseconds, this may not be sufficiently fast for full diagnostic information.

Faster complete data acquisition sufficient for reconstruction of a tomographic image of a slice of interest are enabled through what is known in the art as "half-scan," or "partial-scan" imaging, where projections are acquired for a particular slice to be imaged during a gantry rotation angle less than 360 degrees.

CT systems with a rotating gantry typically have only one radiation source; although at least one medical imaging system is commercially available with two radiation sources.

In the available medical imaging dual-source CT system, the two x-ray tubes are offset by an angle of about 95 degrees. In this system, however, the second imaging chain with a radiation source and a detector does not cover the full imaging field of view: the corresponding projections are truncated.

Security imaging, such as aviation security imaging, also requires very high scanning throughput, which is improved by high temporal resolution. Security CT systems with rotating gantries are available with two radiation sources: in one of these, the two sources are positioned as close as possible and power is pinged from one to the other at various kVp levels, tube current, and beam filtration, to acquire dual-energy projection data.

Other CT security systems use multiple sources arranged on a fixed gantry. This necessarily results in a relatively sparse sampling in the view-angle direction (also named the "projection angle direction").

SUMMARY

The methods and systems disclosed herein allow for high temporal resolution imaging and throughput in both medical imaging and security applications. In particular, system designs are introduced that optimize imaging speed and imaging efficiency specifically in the context of half-scan imaging.

In an embodiment, a computed tomography (CT) imaging system has a radiation detector array and a rotating gantry supporting a plurality $N_s \geq 3$ radiation sources configured to project partially overlapping projections on the radiation detector array. The radiation sources are configured to radiate simultaneously during at least part of imaging, and include at least first and second extreme sources, the first and second extreme sources defining a central angle $\theta_s$ between them. Other radiation sources of the plurality of radiation sources are located between the first and second extreme sources. The central angle $\theta_s$ is less than $\pi$ radians and sufficiently large that the respective projections of radiation from the two extreme sources do not overlap each other on the radiation detector array, but the projections of radiation from each extreme source overlaps one or more projections of radiation from at least one other radiation source of the plurality of radiation sources on the radiation detector array. A processor of the CT system receives data from the radiation detector array and has a memory, the memory has firmware for performing a pre-reconstruction inversion process on the data from the radiation detector array.

In another embodiment, a method of performing a computed tomography (CT) scan of an object in an imaging zone includes providing a plurality of radiation sources, each radiation source directed at an imaging zone and having a fan angle sufficient to cover a field of view, and providing a radiation detector array disposed to receive radiation projected through the field of view by the radiation sources. When enabled, the radiation projected by a first source of the plurality of radiation sources overlaps on the detector array at least in part radiation projected by a second source of the plurality of radiation sources. The method continues with enabling the plurality of radiation sources through a detector integration time of the radiation detector array; measuring radiation received by elements of the radiation detector array through the detector integration time as a set of measurements; and recovering estimates of individual line integrals, recovering further comprising: partitioning the set of measurements into a set of summed line-integrals partitioned into sub-sets; and inverting a linear system associated to each subset to provide individual line integral data. It is noted that the time integration function can be performed in firmware; as is the case in CT systems with photon-counting detectors, wherein each detected photon is recorded with its time of arrival. Integrated measurements are then formed by grouping together such measurements within specific time intervals.

In another embodiment, a computed tomography (CT) imaging system has a stationary gantry with a plurality $N_s$ of partially overlapping radiation sources with a flying radiation detector array which has an extended aperture. A controller is provided and coupled to control motion of the detector array and operation of the overlapping radiation sources, the controller configured to define an instant of time t wherein a plurality greater than or equal to three of K active radiation sources of the partially overlapping radiation sources are in view of the detector and configured to simultaneously irradiate the detector array with overlapping radiation projections on the detector array, the at least three active radiation sources comprising two extreme radiation sources in view of the detector array at instant t. In this embodiment, the two extreme radiation sources in view of the radiation detector at time t define a central angle θs such that the respective projections of the two extreme sources do not overlap on the detector.

In another embodiment, a computed tomography (CT) imaging system has a rotating source gantry with a plurality $N_s$ of partially overlapping radiation sources mounted thereon, the rotating source gantry configured to rotate around a rotation axis; and a flying detector gantry with an extended aperture and a radiation detector array, the rotating gantries configured such that at a particular instant in time t a plurality K≥2 of active radiation sources are in view of the detector array, a subset of the plurality K of active radiation sources being configured to simultaneously irradiate, the subset further defining two extreme radiation sources in view of the detector at instant t, the flying detector gantry configured to rotate about the rotation axis. The system also has an image processor coupled to receive data from the flying detector and having a memory, the memory containing firmware adapted to perform a pre-reconstruction inversion process. In this system two of the K partially overlapping radiation sources are extreme radiation sources in view of the detector at time t define a central angle $θ_s$ such that the respective projections of the two extreme sources do not overlap on the detector.

In another embodiment, a CT system in an optimized geometry has an imaging-field-of-view centered on a rotation axis and of radius $R_M$ as measured from the rotation axis; the system including a rotating gantry supporting two radiation sources located at a minimum distance $R_S$ from the rotation axis and separated by a central angle $Δθ_s$, with a system fan-angle Γ given by $$Γ = \arcsine\left(\frac{R_M}{R_S}\right).$$

In this system substantially $$Γ = \frac{π}{6}$$

and the central angle between the two radiation sources is substantially:

$$Δθ_S = π - 2Γ = \frac{2π}{3}.$$

In another embodiment, a CT system in an optimized geometry has an imaging-field-of-view of centered on a rotation axis and of radius $R_M$ as measured from the rotation axis; the system including a rotating gantry supporting three radiation sources at a minimum distance $R_S$ from the rotation axis and defining two extreme radiation sources separated by a central angle $θ_s$; and a system fan-angle Γ given by $$Γ = \arcsine\left(\frac{R_M}{R_S}\right);$$

where substantially $$Γ = \frac{π}{10}$$

and the central angle between the two extreme radiation sources is substantially:

$$θ_S = π - 2Γ = \frac{4π}{5}.$$

In another embodiment, a CT system in an optimized geometry has an imaging-field-of-view centered on a rotation axis and of radius $R_M$ as measured from the rotation axis; and a rotating gantry supporting five radiation sources at a minimum distance $R_S$ from the rotation axis, and configured to rotate about the rotation axis with a system fan-angle Γ given by $$Γ = \arcsine\left(\frac{R_M}{R_S}\right);$$

and substantially $$Γ = \frac{π}{10}$$

with the radiation sources substantially equispaced over a central angle equal to 2π.

In another embodiment, an x-ray radiation imaging system has a plurality of individual radiation sources and a radiation detector array, the sources configured to expose an object or living being simultaneously, the simultaneously exposing source projections overlapping at least in part on the radiation detector.

DETAILED DESCRIPTION

Definitions

Figure 1:
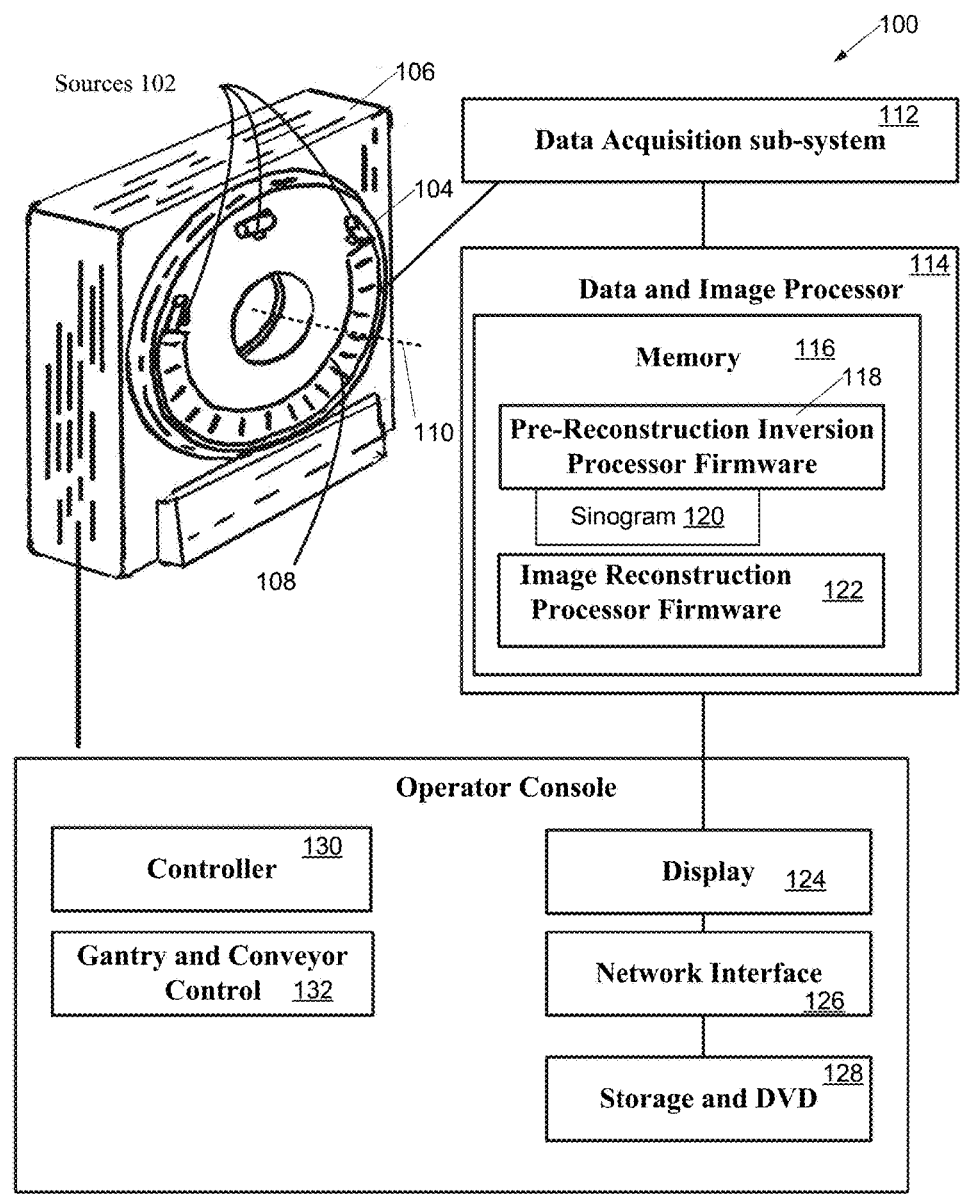
FIG. 1 is a diagram illustrating a CT system frame and gantry per an embodiment of the present invention.

The following terms are used in this invention disclosure with the specific meaning now described.

"Radiation source:" A punctual, individual source of radiation useful for imaging in CT. In particular, an x-ray source; this includes x-ray sources in all their variations, from individual x-ray tube, including fixed-anode tubes, rotating-anode tubes, to individual radiation source elements in a controllable array of radiation source, to large radiation sources that sweep an electron beam in a vacuum envelope to define in time a spatial excursion of a radiation focal-spot (the area from which most of the useful radiation in the beam is emitted). Radiation sources include conventional x-ray tubes as well as "cold-cathode" x-ray sources; carbon nanotubes x-ray sources; piezoelectric x-ray sources; magnetostrictive x-ray sources; tribogenic x-ray sources; and generally any x-ray source as known in the art. Further, the term radiation source will also be understood to comprise light and electromagnetic radiation source in all practical energy/wavelengths practical for imaging; charged particle radiation source, such as proton radiation source; and generally any form of radiation useful for imaging. In the claims, the term "radiation source" will be understood to comprise any/all of the above.

"Fan-angle:" the angle of a projection line from the source (modeled as a point source) to the center of one cell on an array of detector cells. Generally the fan-angle is measured from the central line joining the source to the system iso-center O. Thus an x-ray path or projection line fan-angle is relative to the source.

"Imaging or measurement field-of-view (MFOV) of radius $R_M$:" the radius of a disk centered on system iso-center O such that in normal operation the full field-of-view is exposed by one or a plurality of radiation source(s) for the acquisition of a fan-beam projection. The radius $R_M$ in turn is given by the measurement cell that is furthest away from iso-center, in third-generation CT geometry; in fourth-generation geometry, it is determined by the x-ray source collimator(s) lateral extents, and by the timing of individual detector cell data acquisition.

"Maximum fan-angle:" For a given distance $R_S$ from the iso-center O to a given source, the maximum fan-angle associated with the measurement field-of-view of radius $R_M$ is given by:

$$\Gamma = a\sin\frac{R_M}{R_S}.$$

An "axial" scan occurs when the source rotates around the patient with the patient table not advancing through the gantry. Such a scan may include data acquisition over more or less than one 360-degree source rotation, as further explained below.

A "helical scan" occurs when the patient table is advanced through the gantry concurrent with x-ray source activation and rotation around the patient table.

"Full-scan:" Refers to a data acquisition mode wherein an x-ray source rotates 360-degrees around the patient or object to be imaged, and projection data for one particular slice in the patient are acquired over 360-degrees of source angles. In helical acquisition mode, the x-ray source rotates continuously within the gantry for an extended period of time (often termed "a scan"), and data for several "full-scans" are acquired in "a scan." Thus the term "scan" by itself can be ambiguous.

"Half-scan:" Refers to a data acquisition mode where for a given slice through the object, the x-ray source rotates and data are acquired over a source angle excursion equal to $\pi+2\Gamma$.

"Partial-scan:" Refers to a data acquisition mode where for a given slice through the object, the x-ray source rotates and data are acquired over a source angle excursion in the range $[\pi+2\Gamma, 2\pi]$. This is an extension of the concept of half-scan data acquisition described above.

"Over-scan:" Refers to a data acquisition mode and image reconstruction method where for a given slice through the object, data acquired with source angular excursion greater than $2\pi$ contribute to the reconstruction of the given tomographic slice.

All the above data acquisition modes may occur during a scan comprising source exposure and data acquisition from a multiplicity of rotations. In that case, the respective terms apply to the reconstruction of a specific image surface from a subset of the total "scan" projection data.

"Central angle:" The angle between two lines passing through iso-center O, and measured at O. It is convenient to specify source angles, source separations, and detector angular extents, in terms of their respective central angles.

"System matrix:" By linearization of the CT data acquisition problem it is possible to represent the relationship between the unknowns (image pixel linear x-ray attenuation coefficient values) and the measurements (projection measurements acquired by the detector) by a matrix, termed the "system matrix."

"Inverse Problem:" A problem involving the estimation of unknowns from a set of measurement, most measurements relating two or more unknown in a single equation. The inverse problem may be linear or not.

"Matrix Inversion:" The algebraic process of determining unknowns from a set of measurements in a linear formulation of a problem.

"Under-determined inverse problem:" An inverse problem with more unknowns than measurements.

"Ill-posed inverse problem:" An inverse problem such that noise or uncertainties in the measurements are amplified through any attempt at inversion. The system matrix for such an imaging system, either as posed or as a result of linearization, then exhibits a large "condition number," as is known in the art. Computed tomography is a proto-typical example of a data acquisition modality leading to an ill-posed inversion problem, that of reconstructing tomographic images from the acquired projection data.

"Regularization:" An under-determined or ill-posed inverse problem can be regularized by the use of a-priori information about the object being imaged. That is, specific constraints are applied to the problem. For example, in CT imaging, we know the unknowns (which are the linear attenuation coefficients of the object being imaged) to be positive. Thus we impose our inversion estimates to be positive.

"Primary beam:" The x-ray beam transmitted through an object without deflection or scattering.

"Scattered radiation:" any x-ray radiation that has undergone a deflection/scattering event on its originally straight travel path.

"Simultaneous exposure:" In the context of this disclosure, simultaneous exposure occurs when two or more x-ray/radiation sources are simultaneously active and irradiating the patient/object to be imaged.

"Simultaneous exposure of an individual detector cell:" In this document, simultaneous exposure of an individual detector cell occurs when two or more x-ray sources are simultaneously active and their projections overlap on at least part of the detector; that is, at least one detector cell is being impinged by primary beams from two or more x-ray sources. In the following the term "simultaneous exposure" is also used with this meaning when there is no risk of confusion.

"Radiation source array:" A plurality of individual x-ray sources provided as a single sub-system. In specific cases, the individual x-ray source elements within the array can be addressed or controlled individually.

"Activated (pertains to a radiation source):" The radiation source is energized and is ready to produce a radiation beam. For example, in a conventional x-ray tube, the filament may be heated by a current and electrons "boiled off." However, the electron beam to the anode may be cut-off or pinched by an applied voltage, so that the amount of emitted radiation is either non-existent or very small. So an activated radiation source may emit a radiation beam or not.

"Detector," also "radiation detector:" Refers to the sub-system comprising the entirely of radiation measurement cells; each of these cells gives rise to a measurement at specific time intervals ("time sampling intervals") and is referred to as an "individual detector cell." Detector cells may be arranged on a variety of surface configurations; all the cells in a detector do not need to form a contiguous surface. A detector may include several components, such as separate detector arrays. For illustration, in some configurations, a component of the detector is rotating on a gantry, and another component of the detector is fixed in the laboratory coordinate system.

"Central ray:" A mathematical line from the mathematical, punctual center of source to the detector passing through the system iso-center O.

"Gantry:" Mechanical apparatus supporting a rotating source, array of source, or plurality of sources, and optionally one or a plurality of detector(s).

"Drum:" Part of a gantry, a drum is a mechanical device that rotates around the patient or object to be imaged in CT. Thus a CT system may present one or more rotating gantry/drums. Synonym for "rotating gantry" component.

"Image reconstruction:" The CT inverse problem of recovering the object linear attenuation coefficient spatial distribution from a set of projection measurements.

"Projection:" A set of measurements normally associated with a source at a given position with respect to the object. In CT, a given projection is considered complete if substantially all rays from the source through the measurement field-of-view are traversed by an x-ray beam and give rise of a detector measurement. Also called a "view." The term projection is also used to denote the mathematical set of lines originating at a source, passing through the MFOV, and impinging on the detector; whether or not actual radiation beams are emitted by the source.

"Fan-beam projection:" In CT, projections are acquired at a given time in the form of a fan of rays emitted by a source, irradiating the measurement-field-of-view, and then impinging on a detector. In any practical implementation, a fan-projection is acquired during a finite time interval, called the "detector integration time."

"Low-exposure:" A relative term, describing illumination of an object by a radiation beam of lower intensity than expected in typical imaging practice.

"Projection ray:" Geometrically, a line from a punctual radiation source to the punctual center of an individual detector at a given time.

By extension, a projection ray: the geometric envelope of the lines originating from one point on the x-ray source focal spot and ending on the surface of an individual detector cell at a given instant in time. Thus a projection ray in this sense is a beam around a center line with a limited three-dimensional spatial extend and a cross-section area in a plane orthogonal to the projection ray above defined. Thus a ray corresponds to the envelope of the x-ray paths extending from the entire active focal spot area on the x-ray source to the entire active detector cell area, at a given instant in time. To each ray through the object we associate a line-integral of the object linear attenuation coefficients.

By extension, a projection ray: corresponds to the total three-dimensional volume obtained when the three-dimensional beam described above corresponding to one instant in time is swept during an integration time corresponding to the acquisition of one detector cell sample. To such a projection ray, we associate a line-integral and a measurement at the detector.

"Line-integral:" The measurement associated to a projection ray in a CT system. A projection typically comprises several thousand line integrals; and a complete data set (see "sinogram") for one image to be reconstructed typically comprises several hundreds of projections worth of line-integral data. The line-integrals form the input to the image reconstruction methods/process—independently of the specific of the image reconstruction algorithm; that is, all reconstruction algorithms take as input the line-integral data, also referred as the "individual line-integral" data, as opposed to the summed projection data that are part of the present invention. A line-integral L refers to an integral over a path; and the description below by abuse of language occasionally use the term line-integral to refer to a path through the object, or a line associated with this path, corresponding to the individual line-integral measurement.

"Detector quarter-offset:" A system configuration whereby by offsetting the detector such that a central ray from a source intersect a detector cell at ¼ or ¾ of its width, the conjugate ray of a given line-integral L—acquired after substantially 180-degrees gantry rotation—will be sampled that is parallel and laterally offset from L by about ½ of the detector width. This enables the acquisition of sinogram data sets with higher resolution. Conversely, the quarter offset can be ignored and the conjugate ray considered to provide a second estimate of line-integral L. Similar sampling effects are achieved by deflecting the electron beam focal spot on the x-ray target, either magnetically or electrostatically.

"Summed projection data," or "summed line-integrals:" In the CT systems of the present invention, some line-integrals may be measured individually; but most line-integrals are measured in sums; that is, a given measurement is associated to radiation detected along a plurality of paths ending on one detector cell at a given time/time-interval. It is thus necessary to examine conditions under which the individual line-integral data may be estimated from the summed data, as is required for image reconstruction. This disclosure describes CT systems that lead to summed data from which the individual line-integral estimates may be recovered, and methods of doing so. This implies necessarily solving an inverse problem.

Thus the systems and methods of the present invention are concerned, at least in part, with the setting and solving of a "pre-reconstruction inversion problem." As is described in the disclosure, specific CT system designs lead to conditions that are favorable to the solving of this problem.

"Line-integral bundle," or "L-bundle:" In the CT systems of the present invention, often measurements of one specific line-integral involve other line integrals, through the summed projection data described above. Generally speaking, for a system having $N_s$ radiation sources, over a half system rotation, $N_s$ summed measurement will involve a particular line-integral L. To each such measurement is associated a set of up to $N_s-1$ other individual line-integrals. Thus the set of all individual line-integrals associated through summed measurement with line L is described as the "L-line-integral bundle," or line-integral bundle for short. Since each individual-line integral is associated to an unknown, to the L-bundle corresponds a set of unknowns that can be retrieved through a pre-reconstruction inversion process. To each L-bundle is associated a corresponding set of equations, the solution of which provides estimates for each of the individual line-integrals associated with the summed measurements for the L-bundle.

"L-sheath:" Under certain assumptions related to detector quarter offset and/or electron-beam focal spot deflection—specifically if we ignore the effect of detector quarter offset, we consider the line integrals sets associated to a given line L and corresponding to a full-scan acquisition or more; that is, data acquisition with system gantry rotation over $2\pi$ or more. The concept of L-bundle is thus extended to that of L-sheath, the collection of relevant L-bundles associated with a specific line integral measurement and path L. Each line-integral sheath is associated a system of equations, that under the specific conditions described in this disclosure, may be inverted to give an estimate of the individual line-integral measurement associated to L. Since under those specific data-acquisition modes a given line-integral L will be estimated as part of a plurality of bundles, we will have access to several estimates of the line-integral L; statistics and signal processing methods are known in the art that allow to obtain an improved estimate for line-integral L as compared to each separately obtained estimate. In general, a given line-integral L will figure in one bundle for a half-rotation; 2 bundles for a full-rotation; and so-forth.

"Central ray:" A projection ray from a source to the detector surface passing through the system iso-center O (that is, the point O is included in the projection ray).

A projection is "truncated" if some of the rays in the projection that do intersect the imaging field-of-view do not lead to a measurement; this does not include the effect of x-rays falling on an anti-scatter grid element or such on the detector.

Conversely, a projection is "un-truncated" if all projection rays intersecting the imaging field-of-view lead to a measurement.

"Sinogram (single row and multi-row detectors):" A sinogram is a set of projection data associated with a given slice through the object. The sinogram is thus the data set used by a given CT image reconstruction algorithm to generate a tomographic image in a pre-selected slice of interest. In CT, it is often arranged as a set of views, each including a set of detector cell measurements. A typical CT sinogram contains about 1,000 views or projections, each projection containing several hundred measurements. During a typical scan, projection are acquired that can be re-arranged/re-organized into sinograms in a large number of ways. It is typical to associate the term sinogram to the set of data that will be used for the reconstruction of a specific tomographic image.

"Detector distance:" In this document, the term "detector distance" means the smallest (minimum) of the distances from the system iso-center O to the detector surface along the central rays from the various sources to the detector surface.

"Flying detector:" In this document, the term "flying detector" means a detector mounted on the inside surface of a rotating gantry; the rotating gantry being generally cylindrical in shape and centered on the system iso-center O. In operation, the flying detector rotates inside a second gantry that supports a plurality of radiation sources. The flying detector comprises an extended aperture of dimensions such that x-ray sources arranged on the gantry external to the flying detector can illuminate therethrough over a central angle substantially equal to $(\pi-2\Gamma)$ radians; therefore, depending on the geometry of the system, and the dimension of the outer gantry supporting the sources, the actual aperture dimension may differ to some extent from the nominal $(\pi-2\Gamma)$ radians; this aperture is referred to as the "extended flying detector aperture" or "extended aperture" for short. The outer gantry, supporting the x-ray sources, may be either rotating or fixed in the laboratory reference frame (if it rotates, it can rotate in either direction with respect to the flying detector rotation direction). The flying detector further has active detector cells distributed over a central angle substantially equal to the complementary arc in $2\pi$ radians, that is $(\pi+2\Gamma)$ radians. The flying detector may have one or a plurality of detector cell rows, generally arranged along the z direction. It may have other elements as known in the art, including anti-scatter-grids (ASGs); the ASGs lamellas may be arranged in a direction generally parallel to the central imaging plane defined by axes x and y. The flying detector may include indirect or direct radiation detection elements as known in the art. Also called "flying detector gantry."

A radiation source is said to be "in view of the detector" or "visible from the detector" if it is activated, and such that when the source is not muted (as by electron-beam pinching as described above) the entire fan-beam of radiation rays originating from the source, exiting the source collimator element, and intersecting the imaging field-of-view, impinges or would impinge on the surface of radiation detector (whether on a radiation detection element, an ASG lamella, or another component of the radiation detector). That is, the corresponding projection is un-truncated. In the context of a system with a flying detector, this implies that any ray from such a source passing through the MFOV is not blocked by flying detector components other than the entrance surface of the radiation detector; i.e. during the (short) time duration that a subset of the mathematical lines from the source through the MFOV are blocked by the flying detector, the source is NOT considered in view of the detector.

"Source distance:" In general, the radiation sources will be positioned on a gantry, either rotating or fixed, at substantially the same distance from iso-center. However, in specific designs, this distance may vary from source to source; in particular, should radiation source arrays be generally arranged on flat surfaces, then the distances from the various individual source elements to O (or to the rotation axis) will vary slightly. More generally, it may be desirable to position the sources at position offsets with respect to their distance to O. In the claims, the term "source distance" and the variable means the smallest (minimum) of the distances from the system iso-center O to the radiation sources focal spot centers along the central rays from O to the respective radiation source focal spot centers.

"System fan-angle $\Gamma$:" Similarly, since the maximum useful fan-angle is generally associated to the radius of the measurement/imaging field-of-view $R_M$ and to the source distance, to each source corresponds a maximum fan-angle value $\Gamma$ as previously described. In this document, by system fan-angle or Greek letter $\Gamma$ it is meant the largest of these fan-angles, associated with the one source the closest from iso-center; in other word, is defined by $R_M$ and the source distance $R_S$ defined above; Thus the system fan-angle is given by:

$$\Gamma = a\sin\left(\frac{R_M}{R_S}\right).$$

"Extreme sources:" $\theta_S$ is the central angle between the two extreme sources in a set of $N_s$ sources arranged over a central angle generally less than $(\pi+2\Gamma)$ radians on a rotating gantry, whether the sources be equispaced or not. In a system with a flying detector, and either a rotating source gantry of a fixed gantry supporting a large number of sources, the extreme source angle $\theta_S$ represents the central angle between the two sources in view of the detector at a given time t through the flying detector extended aperture. Thus in principle, the extreme source angle can vary with time, $\theta_S=\theta_S(t)$.

When the sources are equispaced, the angle $\Delta\theta_s$ represents the central angle between two adjacent sources.

A set of $N_s$ radiation sources is said to be "partially overlapping" if the projections associated with adjacent sources, virtual or actual radiation projections, overlap at least partially on at least part of the detector. Thus when radiation sources are partially overlapping, at least a subset of the detector cells would give rise to summed line-integral measurement(s), when x-ray beams are emitted by the adjacent sources.

A CT system iso-center is a location, generally coinciding with the system center of rotation. It is understood that due to mechanical tolerances, vibrations, the system iso-center in practice lies within a small, mathematically defined, volume of space. It is generally located on the system rotation axis, see below.

"Optimized geometry:" within this document, refers to a CT system such that the system fan-angle has been calculated according to a specific criterion described herein. A system with parameter values substantially equal to the optimized values is then considered in an optimized geometry. Thus various CT scanner geometries and geometrical dimensions are described; corresponding to a typical medical CT system dimensions; a "long" and a "short" CT system geometry as compared to the medical CT system.

"Electron-beam radiation sources:" wherein an electron beam can be swept laterally within an extended vacuum envelope. The extent of lateral sweep is such that an electron-beam radiation source can be used as a substitute for a source array of significant extent; that is a large number of individual sources.

"System rotation axis" or "rotation axis:" Generally defined as the z axis; is the axis of rotation for the radiation sources, the radiation detector, or both. This is an imaginary line associated with the main rotational movement of the gantry, and generally perpendicular to the main imaging plane; the main imaging plane itself containing two mathematical coordinate axes for x and y. The intersection of the rotation axis and the main imaging plane defines the system iso-center O, c.f. above description, a mathematical point from which various system distances are measured. In case of elements being offset in z from the system central planes, their respective distances "from iso-center" are in fact measured from the system axis of rotation. Thus their "distances" refer to distances to/from the rotation axis.

In this document, the terms "a sin" or "a sine" refer to an Arcsine function, an inverse of sine function. More specifically it refers to the inverse of the sine function with range −90 degrees to 90 degrees.

The description below assumes clockwise system rotation; actual system rotation can be in either direction.

The System

It should be noted that the matter contained in the following description and/or shown in the accompanying drawings may be embodied in various forms, and should therefore be interpreted as illustrative, and not in a limiting sense. Elements shown in the drawings are not necessarily to scale and may be exaggerated, enlarged or simplified, to facilitate understanding of the invention.

Whereas the invention is described in terms of x-ray radiation CT, it applies also to optical CT, proton CT, and other forms of computed tomography, including diffractive modalities such as ultrasound. It also is relevant to CT in all of its applications, including but not limited to diagnostic medical CT, screening medical CT, therapy medical CT (MeV energies), aviation security screening, industrial design, research, and screening; and others.

Additionally, while the invention is primarily described with a detector mounted on a rotating gantry, it applies as well to configurations where the detector is fixed and the sources are mounted on a rotating gantry within the space defined by the detectors, a detector configuration similar to the "fourth-generation CT" known in the prior art. The invention also applies to CT systems with substantially a full circular array of x-ray sources on a fixed part of the gantry, with detectors of specific shapes and configurations rotating within.

Further, it is understood that the x-ray sources, although shown co-planar in the attached figures, may be offset with respect to the z-axis. Sources offset in z may present advantages in terms of the acceptable imaging pitch: the pitch being the defined as the ratio of table advance per rotation divided by the detector width along z, as measured on the center axis z. This source offset along z may also optionally be combined with an offset of the detector cells in z (variable along the detector arc). Accordingly, when in the following description reference is made to an angle between two or more sources, or an angular gantry rotation range, it is understood that such angle refers to an angle between two sources as projected orthogonally on a the x-y plane of the system gantry, fixed in the laboratory. Such angles when measured with respect to lines in the plane x-y originating from O are also referred as "central angles." Thus detector arrays and source arrays may be presenting an elongated dimension axis at an angle with-respect-to the x-y plane.

Arrays of individual x-ray source emitters are now becoming possible, and some such technologies are in the prototype stage. XinRay Systems, Research Triangle Park, N.C., has developed linear arrays of individually addressable sources (http://xinraysystems.com/), utilizing proprietary carbon nanotube based X-ray sources ("cold cathode" tubes). U.S. Pat. No. 8,755,493 discloses piezoelectric or pyroelectric crystals capable of generating high-energy electron beams and thus x-rays; the technology is potentially available to form an array of point sources. Tribogenics (http://tribogenics.com/), Los Angeles, Calif., has developed an alternative way to emit high-energy electrons that may in specific implementations be amenable to the design of arrays of x-ray sources. Thus the invention also applies to imaging systems provided with arrays of x-ray sources.

Additional CT embodiments with both rotating sources and fixed sources describe systems with arrays of x-ray sources substantially distributed over an angle covering up to $(\pi+2\Gamma)$ radians in central angle.

In the entirety of this document, it is understood that various sources among a system's plurality of radiation sources may emit radiations of various spectral properties and with various focal spot distributions. The various spectral properties come from, as is known in the art in the case of x-ray sources, choices of target material, tube current (mA), peak kilo-voltage (kVp), and beam filtration. The focal spot intensity distribution varies depending on the beam optics properties of each source. Thus, for example, a subset of the system sources may be operated at a given kVp, beam current, and beam filtration, and a second subset at another kVp, beam current, and beam filtration. Many combinations are possible.

A multiple-source CT scanner system 100 (FIG. 1) as described herein has multiple radiation sources 102, which in a particular embodiment are X-ray tubes. The radiation sources 102 are mounted in a cylindrical, rotatable, gantry 104 that is rotatably mounted in a frame 106. The rotatable gantry 104 has a cylindrical passage in which a patient or object to be scanned is positioned on a movable table or conveyor (not shown) that passes through the passage. The cylindrical passage has an axis 110 known herein as the iso-center of the system. A radiation detector array 108 is mounted to receive radiation emitted by sources 102 that may have passed through the patient or object in the passage. In some embodiments the detector array 108 is mounted to the gantry and rotates with the tubes, in other embodiments the detector array is mounted to the frame, as described herein. The detector array 108 is coupled to provide radiation detection measurements through a data acquisition subsystem 112 into a processor 114. Processor 114 has a memory system 116 that contains an inversion firmware 118 that processes detector data into a sonogram 120. Memory 116 also contains an image reconstruction firmware 122 that constructs tomographic images of the patient or object to be scanned, the tomographic images may be viewed on display 124, uploaded via network interface 126 into an electronic medical records system (not shown) or radiological database, or written onto DVD's for physical record storage, radiologist review, or transfer to other facilities. Gantry 104, radiation sources 102, and data acquisition 112 all operate under control of a controller 130 and gantry & conveyor control 132.

Figure 1A:
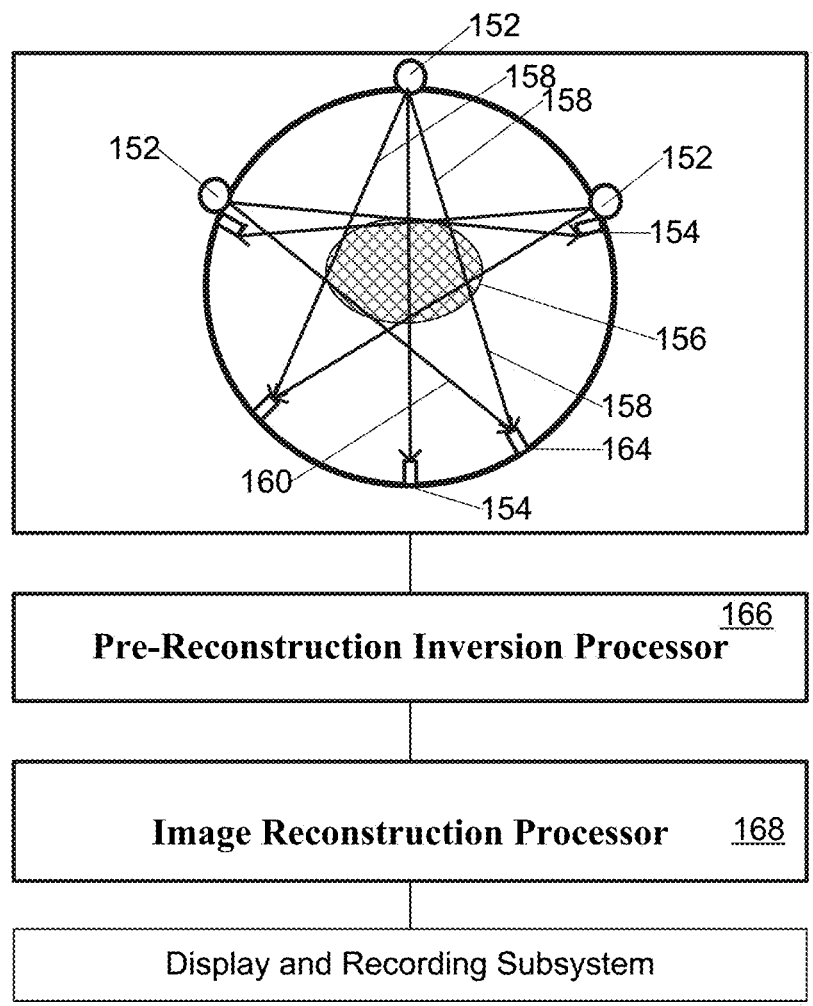
FIG. 1A is a schematic representation of the CT system of FIG. 1.

System 100, 150 is representable schematically as illustrated in FIG. 1A, where radiation sources 152 are represented as circles and specific individual detector elements 154 of the radiation detector array are represented as rectangles. The patient or object to be scanned 156 is located such that at least some lines 158, 160, and 162 drawn from radiation sources 152 to radiation detector elements 154, 164 pass through the patient or object 156. When radiation sources 152 are active, X-ray radiation passes along each line 158 to the detector elements, and some of the radiation is absorbed by patient or object 156, attenuation along each line is a line integral of attenuation at multiple points in the patient or object 156 along the line. Each detector element receives a signal that represents a sum of radiation along each line (and thus a function of each line integral of attenuation) 160, 162 from active radiation sources that illuminates that element 164. Signals from detector elements 154, 164, are passed to the pre-reconstruction inversion processor 166, which is implemented as inversion firmware 118 in memory 116 executing on processor 114 to provide sonogram data to a reconstruction processor 168 implemented as reconstruction firmware 122 in memory 116 executing on processor 114 to provide images.

Figure 2:
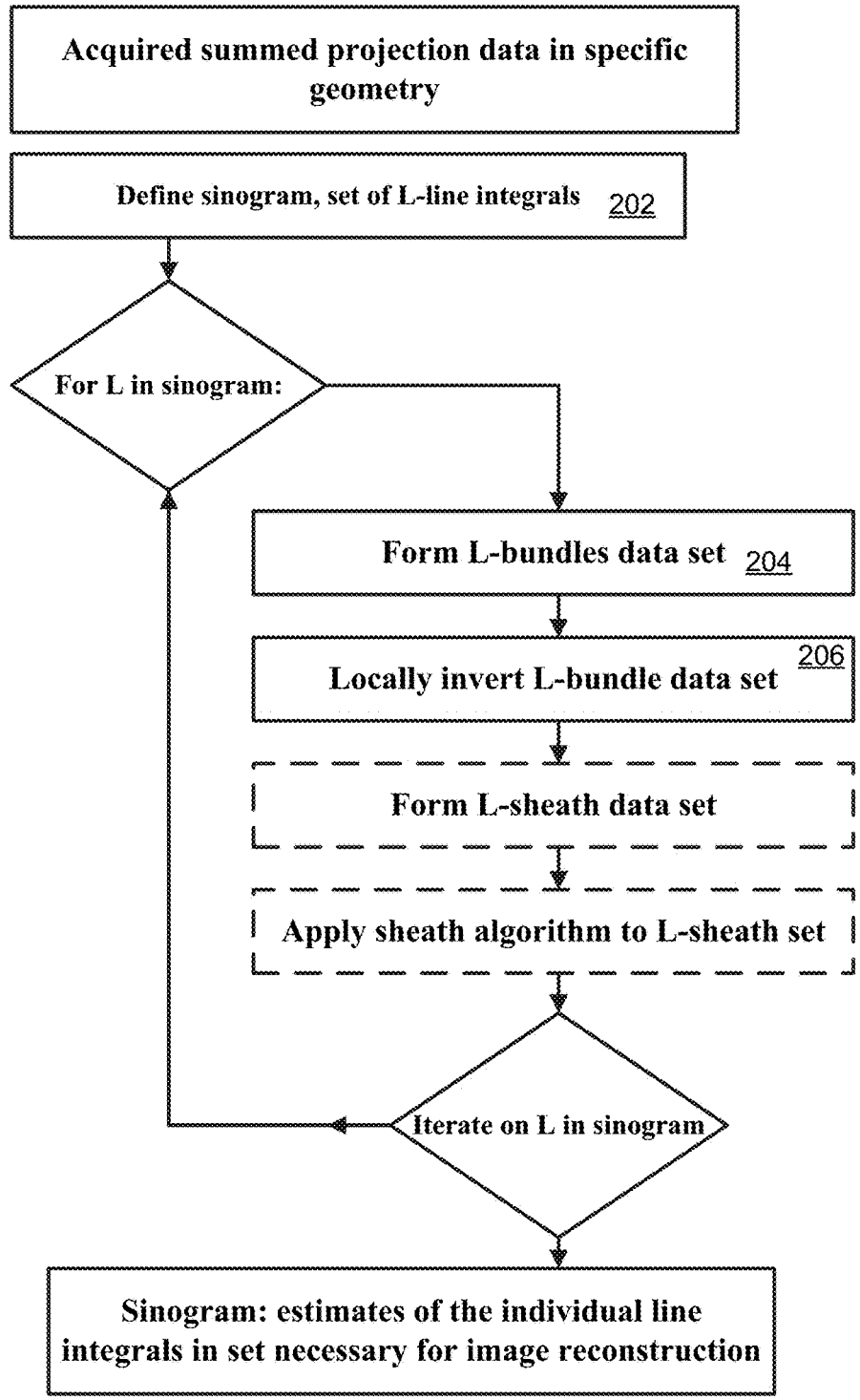
FIG. 2 is an approximate flowchart of a method to perform a pre-reconstruction inversion for a CT system per an embodiment of the present invention.

Tasks performed by pre-reconstruction inversion firmware 118 are illustrated in FIG. 2. Since, in CT scanning systems of the present invention, projections on detector array 108 from two or more radiation sources 152 may overlap, meaning that one or more radiation detector elements 154 receives direct un-scattered radiation from two or more of sources 152, the line integral signals from the radiation detector elements 154, 164 must be separated to produce a sinogram that can be processed with conventional image reconstruction firmware 122. In order to do so, the inversion firmware 118 determines lines L (corresponding to lines 158, 160) associated with paths from each radiation source 152 and each radiation detector element 154, 164. Those lines L associated with each detector element 164 are grouped into an "L-Bundle" or group of related lines. The ensuing L-bundle is then inverted 206, or solved, to separate the radiation detector total readings into separate contributions associated with each line of the L-bundle; these separate contributions are then associated with the corresponding lines in the sinogram provided for image reconstruction. An L-sheath is a collection of L-bundles associated with a line-integral L.

Figure 3A:
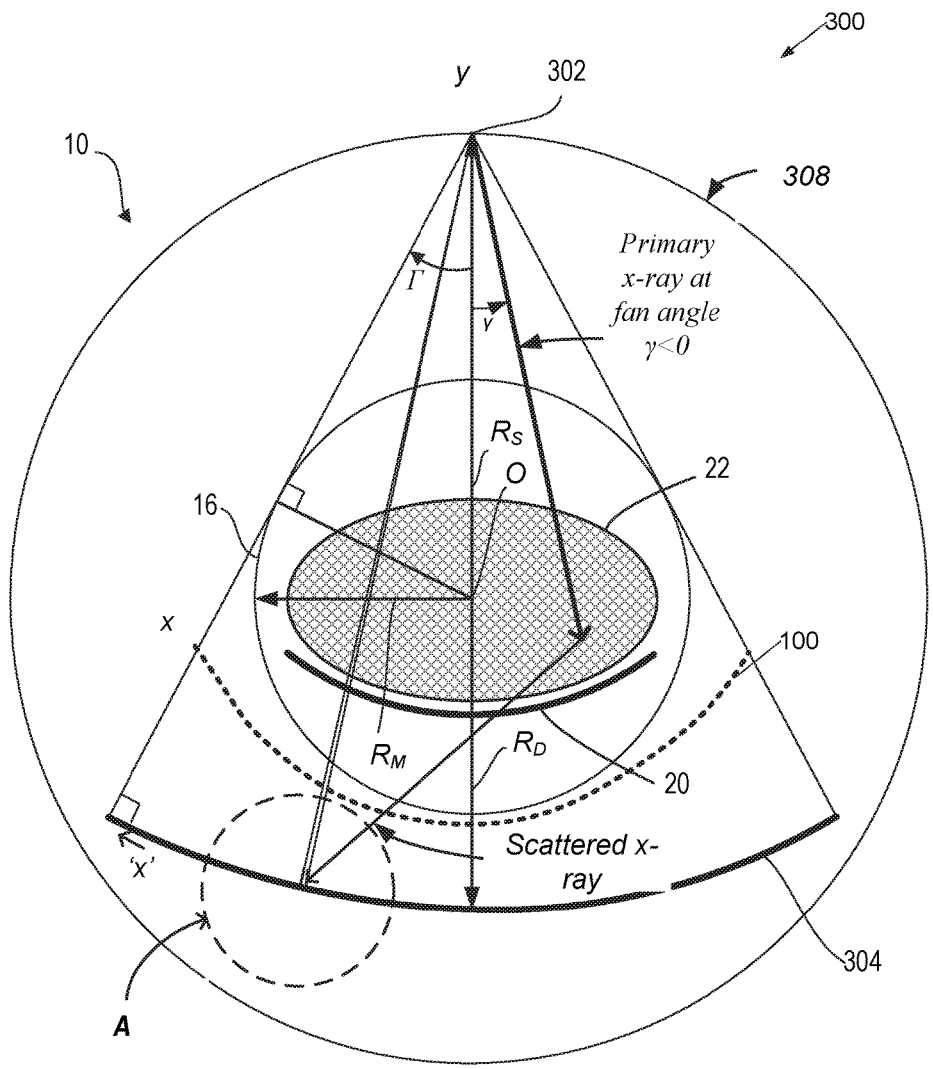
FIG. 3A is a diagram describing the PRIOR ART geometry of a typical third-generation CT system.
Figure 3B:
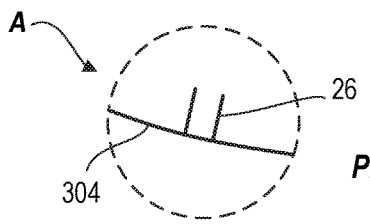
FIG. 3B is a closeup view of a portion of PRIOR ART FIG. 3A.

Turning now to FIG. 3A, the geometry of a prior art CT system 300 is schematically shown. In a "third-generation" geometry, an x-ray tube 302 and a detector array 304 are mounted opposite a patient imaging area on a common rotating gantry (not shown), the source S 302 at radius $R_S$ from the system iso-center O, and the distance from O to the detector on the line from source S through O being $R_D$. As the gantry rotates, source S 302 describes a circle 308. A measured imaging volume or field of view of radius $R_M$ is exposed to radiation from any source position on the circular source trajectory of radius $R_S$. In a typical third-generation geometry, detector array 304 cells and anti-scatter-grids 26 (FIG. 3B) are arranged on an arc of a circle centered at the source S, so every ray from the source through the imaging field of view intersects the detector arc essentially orthogonally. The detector may assume any practical configuration under condition that any ray through the measured-field-of-view intersects the detector array (not necessarily orthogonally); an example will be provided in the geometries of FIG. 9 and following.

A quantity of interest is the dimensionless ratio $Q_R = R_M / R_s$ through which the maximum or useful source fan-angle Γ is defined:

$$\Gamma = \arcsin(Q_R).$$

In the following, various values for $Q_R$ and associated geometries are discussed.

Figure 4:
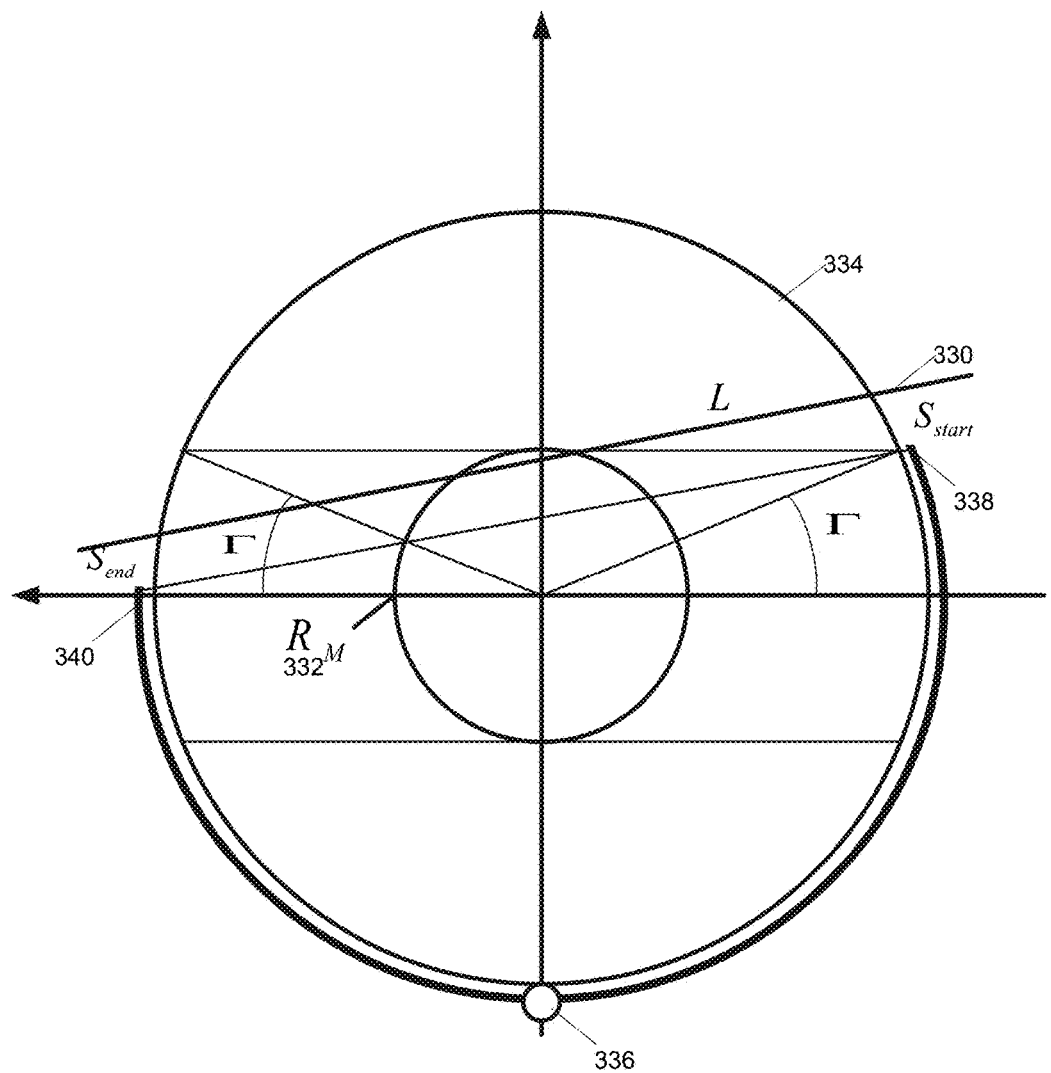
FIG. 4 schematically illustrates the source sampling requirements for full-scan and half-scan complete data acquisition.

In FIG. 4, conditions leading to a complete data acquisition for a tomographic slice of interest are described. It is assumed that every line from a source position S that intersects the detector will provide one measurement of the associated line integral of the x-ray attenuation coefficient; this assumption is equivalent to stating that the detector has a continuous active surface with no gap between sampling cells, an assumption only approximated in practical CT systems. This assumption, commonly made in technical descriptions of CT, is appropriate.

FIG. 4 illustrates an arbitrary line L 330 crossing the measured/imaging field of view indicated by the circle of radius $R_M$ 332 in a CT scanning machine. It is readily seen that a radiation source rotating a full 360-degree circle will be in a position to generate an x-ray beam along line L at two points, each corresponding to an intersection of L with the source trajectory circle 334. Accordingly, in a "full-scan," corresponding to 360 degrees source rotation, every line integral that crosses the object is sampled twice, once with the radiation source at each of two diametrically opposed intersections of line L with the source trajectory. The condition for complete data acquisition sufficient for tomographic image reconstruction, as known in the art, is that any line that crosses the object is measured at least once. Thus a full-scan provides twice the necessary measurements for imaging. It is possible in fan-beam geometries to acquire a complete data set from a smaller source rotation angular range, as is discussed below.

In FIG. 4, a source 336 is shown at the six-o'clock position; and a source angular range with starting point $S_{start}$ 338 and ending point $S_{end}$ 340 is shown by a thick line outside the source circle trajectory. As is clear from the figure, in fan-beam CT data acquisition any source angular range less than $(\pi+2\Gamma)$ radians is not sufficient to provide a complete data acquisition. Conversely, it can be shown and is known in the art that in fan-beam data acquisition a source angular range and data acquisition over exactly $(\pi+2\Gamma)$ radians is necessary and sufficient for a complete CT data acquisition (for substantially exact reconstruction of one image of a static object occupying the entire measured field of view).

Figure 5:
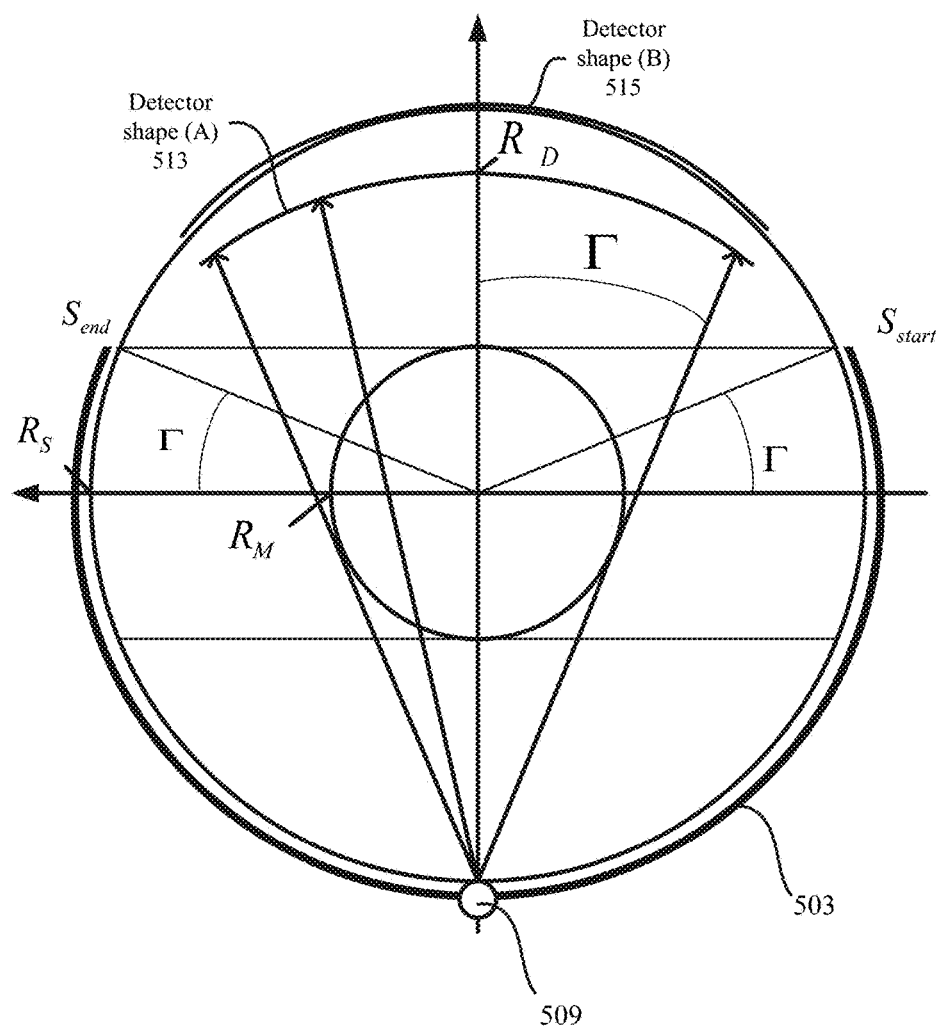
FIG. 5 depicts a source angular range necessary and sufficient for complete data acquisition in a half-scan, and also illustrates two possible geometric detector arrangements.

FIG. 5 is a schematic representation 503 of the minimum source angular excursion to obtain a complete data set for one cross-section image reconstruction, in what is called a "half-scan," that is, data acquisition over $(\pi+2\Gamma)$ radians. This is shown for a source excursion centered on the six o'clock position 509. Also illustrated are two possible detector shapes 513 and 515, the detector(s) rotating in synchrony with the x-ray source(s). Naturally the center of the source projection acquisition range can in principle be located at any position on the source trajectory, depending on the specifics of a data acquisition sequence and the desired reconstructed tomographic image.

Figure 6:
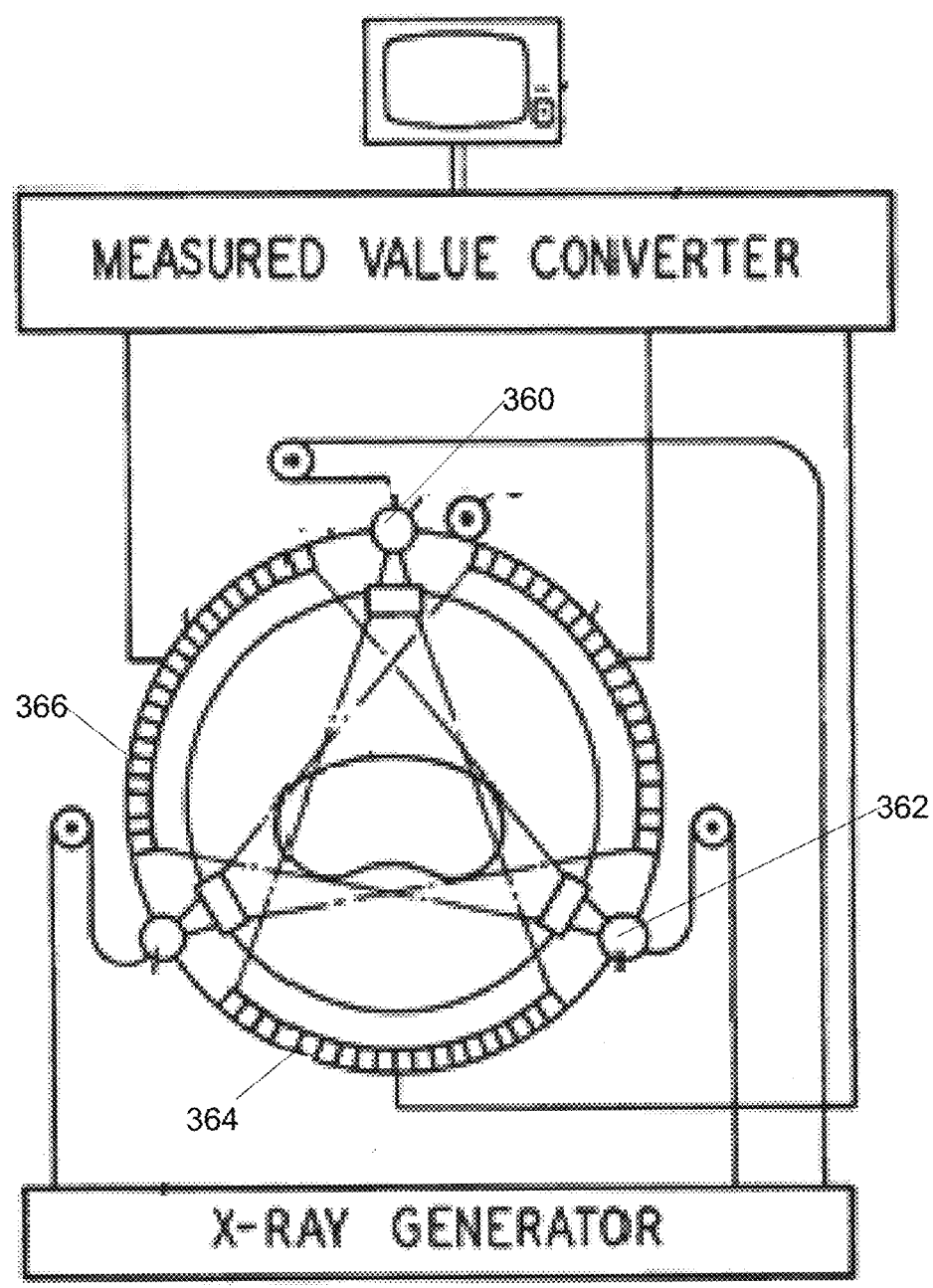
FIG. 6 depicts a PRIOR ART CT system with three radiation sources equispaced over 360 degrees, where each source illuminates a separate detector array.

FIG. 6 illustrates a rotating gantry system with three imaging chains equispaced around 360 degrees, as described in, U.S. Pat. No. 4,150,293 to Franke. Each imaging chain has a radiation source, such as an x-ray tube 360, 362 and a matching detector 364, 366. The matching detectors 364, 366 are mounted on the rotating gantry; in another configuration the detector could be stationary, consisting of a full ring of detector cells, with the three tubes rotating within the area thus defined. Because the three imaging chains operate concurrently, the minimum gantry rotation to obtain source projections/views over 360 degrees is thus 120 degrees. It is convenient to introduce the speed-up factor ratio $Q_s(2\pi)$ that compares the gantry rotation angle for two systems to acquire 360 degrees worth of views:

$Q_s(2\pi)$=(Gantry rotation angle,System 1)/(Gantry rotation angle,System 2).

From the above considerations, for the system to FIG. 4 (System 2) as compared to the reference system of FIG. 1 (System 1):

$Q_s(2\pi)=3.$

For further performance comparison, it is useful to define the normalized speed-up ratio, which accounts for the number of sources $N_s$ and therefore describes the efficiency of the acquisition speed increase:

$$\hat{Q}_s = \frac{Q_s}{N_s}.$$

For the system of FIG. 4, $\hat{Q}_s(2\pi)=1.0$.

The speed-up factor ratio $Q_s(\pi+2\Gamma)$ and normalized ratio $\hat{Q}_s(\pi+2\Gamma)$ are defined similarly to compare the half-scan performance of two systems—that is the respective gantry rotations that are required to acquire the minimum general half-scan data set corresponding to $\pi+2\Gamma$ radians worth of view/projection data acquisition.

Figure 7:
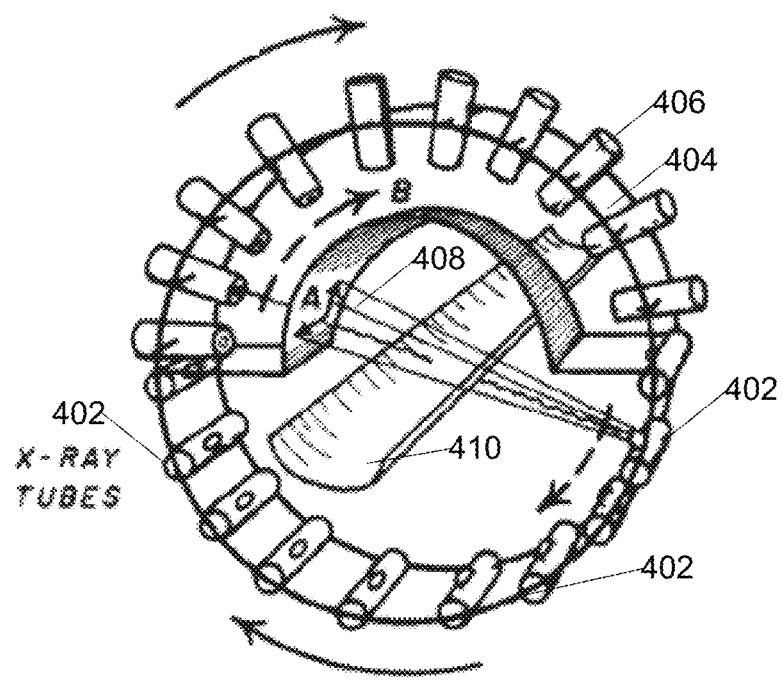
FIG. 7 is a diagram for an experimental CT system with multiple radiation sources equispaced over 180 degrees, according to a PRIOR ART development, wherein each projection associated to an x-ray source and a detector is truncated.

FIG. 7 illustrates an early one-of-a-kind prototype CT system (the "DSR") developed at the Mayo Clinic and having twenty-eight x-ray sources 402 (10 illustrated) equally spaced in a semi-circle (exactly $\pi$ radians or 180 degrees) and mounted on a rotating gantry with an opposing array of radiation detector elements 406 such that x-rays 408 could pass from sources 402 to detectors 408 through a patient or object to be scanned (not shown) positioned on a conveyor 410, as described in R A Robb, A H Lent, B K Gilbert, and A Chu: "The Dynamic Spatial Reconstruct or, A Computed Tomography System for High-Speed Simultaneous Scanning of Multiple Cross Sections of the Heart." Journal of Medical Systems, Vol. 4, No. 2, 1980. This prototype was developed in an attempt at capturing better images of the beating heart; however, there is no description of efficiency of data acquisition speed-up. The use of two, three, or more x-ray sources arranged in a specific arc less than 180 degrees is not contemplated. In particular, the use of a two or a multiplicity of sources arranged in an arc of $\pi-2\Gamma$ radians is not contemplated. It can be shown that the speed-up factors and normalized speed-up factors for such a system with 28 sources arranged over a semi-circle in a typical medical imaging geometry are respectively:

$Q_{28}(\pi+2\Gamma)=4.46; \hat{Q}_{DSR}(\pi+2\Gamma)\sim0.16$ for half-scan imaging; and $Q_{28}(2\pi)=1.75; \hat{Q}_{DSR}(2\pi)\sim0.06$ for full-scan imaging.

Accordingly, such an arrangement of sources is relatively inefficient, as will be described further below. Further, it is noted that the architecture of the DSR is unlike what is described in the present invention: the DSR had a very long geometry, and was limited by the detector technology available at the time; each "imaging chain" having one of the 28 sources and a detector imaged a field-of-view of only 21.4 cm in diameter (versus 50 cm in a typical medical imaging CT). Accordingly the projections were truncated, and a larger field-of-view could be obtained only by combining data from several imaging chains. In that sense, the DSR is akin to a "second-generation" CT system—and these have not been in practical use since the late 1970s.

Figure 8:
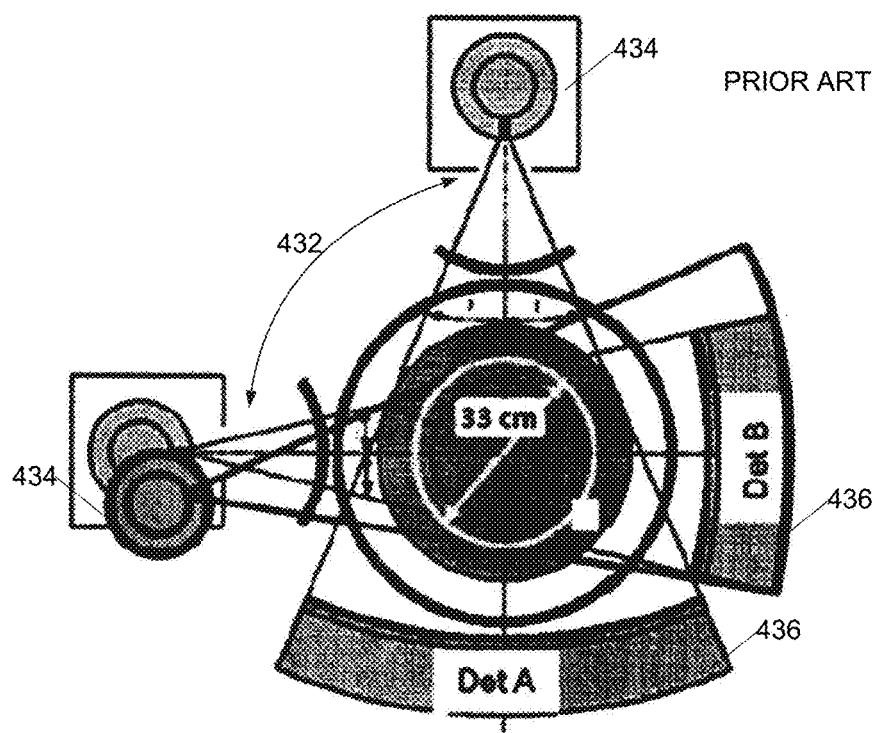
FIG. 8 presents a PRIOR ART medical imaging CT system with the two source offset by about 95 degrees.

FIG. 8 illustrates a medical CT imaging system with two sources over an arc less than 180 degrees. However, the angle 432 between the two sources 434, originally set at 90 degrees, led in that particular design to a truncated second set of projections on detectors 436, with a measured field of view of about 26 cm in diameter, as reported in TG Flohr et al. "First performance evaluation of a dual-source CT (DSCT) system." Eur. Radiol. 16, 256-268 (2006). In a second version of that system, the second tube was offset at about 95 degrees from the first tube, to increase the measured field of view to about 33 cm in diameter, as reported in R Raupach, "Dual Energy Imaging with Dual Source CT System." AAPM Annual Meeting Presentation. Optimization of the dual-source system with respect to half-scan imaging speed or efficiency is not considered. A dual-source system with x-ray tubes optimally distributed with respect to data acquisition speed and efficiency within an arc of angle less than 180 degrees and acquiring non-truncated projections is not presented.

Figure 9:
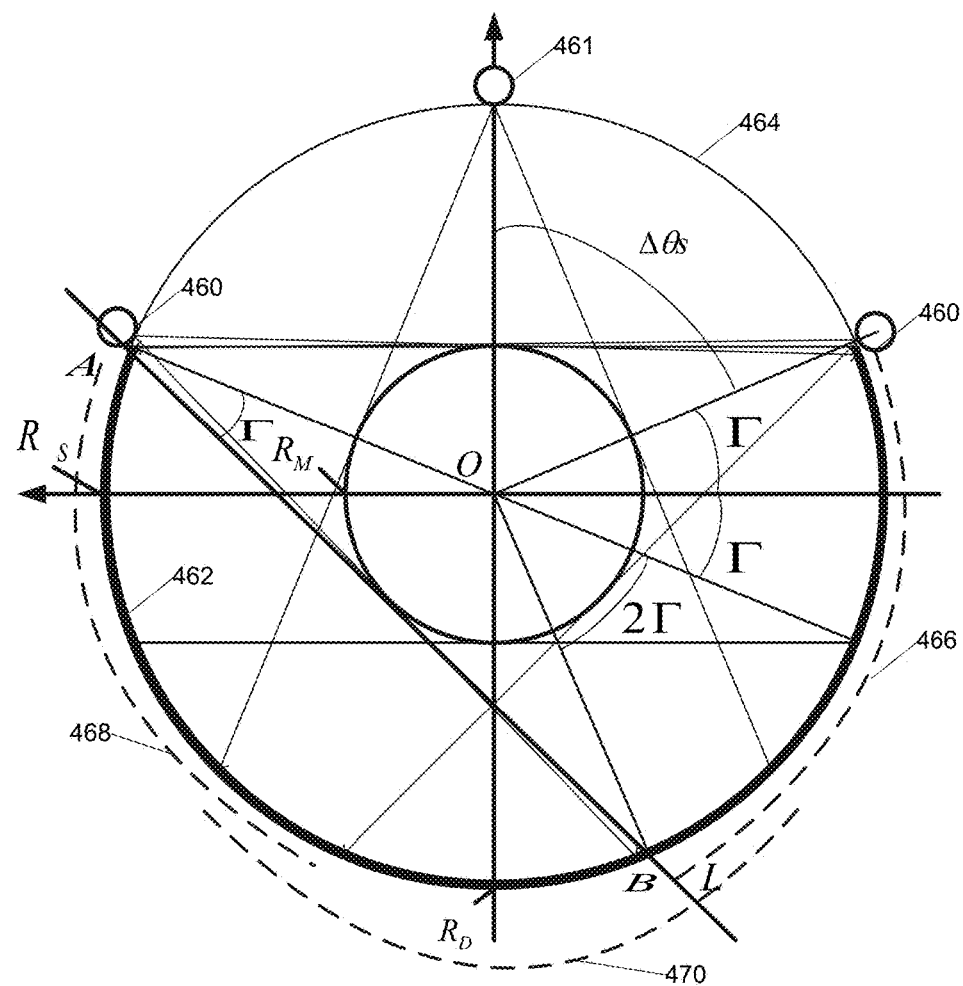
FIG. 9 schematically illustrates a CT system with three radiation sources in a system of geometric dimensions typical of medical imaging, according to an embodiment.

A "half-scan" embodiment of a CT system with three x-ray sources 460, 461 is illustrated in FIG. 9. In the system of FIG. 9, three x-ray tubes 460, 461 are provided and generally arranged on an arc 464, the arc central angle covering less than $\pi$ radians. In the system illustrated, the arc sustained by the sources is substantially equal to (π−2Γ) radians, and the detector array occupies the complementary arc 462, or substantially (π+2Γ) radians. The detector is mounted on the same gantry as the sources, and thus rotates with the sources. The detector arc may assume a variety of shapes. In the system illustrated there is substantial deviation from the iso-centered detector array arc typical of fourth-generation CT. This may be done to improve upon the average alignment between the local normal to the detector cell surface and the impinging radiation. In the system illustrated, the projections 466, 468 of the two extreme sources do not overlap on the detector; although both of these projections overlap at least in part with the beam projected 470 by the central source 461. The use of a distribution central angle for the sources $\theta_s \leq (\pi-2\Gamma)$ radians is advantageous as then, assuming a detector substantially covering the complementary angle in $2\pi$, none of the sources' projections are truncated and the sources are fully utilized.

FIG. 9 illustrates a system with three radiation sources distributed over an arc with extent $\theta_s = \pi - 2\Gamma$ radians in a system with a hybrid design: both radiation sources and the detector are mounted together on a rotating gantry, as is typical in medical imaging CT; however, the detector arc is centered on the system iso-center O, whereas in a typical medical imaging CT system it is centered at the source; further, the detector (central) angle, or angular extent of the active cells, is wider than on a typical CT. The illustrated system dimensions, typical of a medical imaging CT system, are: $R_s$=570 mm; and with $R_d$ the distance from iso-center O to the projection of the central source through iso-center O onto the detector $R_d \sim R_s$. Let $R_M$ be the radius of the measurement field, which defines the diameter of a circular area within which a patient cross-section or a piece of luggage, or any other object to be scanned, must fit entirely for complete data acquisition. The dimensionless ratio $$Q_R = \frac{R_M}{R_S} \sim 0.439;$$

the maximum radiation fan-angle from the central ray joining the source to the detector is: $\Gamma$=a sin($Q_R$)~0.454 radians. The ratio $Q_R$ allows comparison of CT system geometries in terms of short ($Q_R$ relatively large) to long ($Q_R$ relatively small). As we will see below, the above $Q_R$ value of 0.439 defines an intermediate point. In this geometry, we have $$\Delta\theta_s = \frac{\pi - 2\Gamma}{N_s - 1} \sim \frac{2.2335}{2} \sim 1.12 \text{ radians,}$$

and accordingly 1.82~4Γ>Δθ$_s$>2Γ~0.91, and thus:

θ$_s$=2Δθ$_s$>4Γ.

It is apparent from the FIG. 9 that in such a configuration the minimum gantry rotation required to achieve full sampling of a slice of interest is max{Δθ$_s$, 4Γ}=4Γ. (The term Δθ$_s$ comes from the requirement to avoid source angular sampling gaps; the factor 4Γ from the requirement for the source at about 2 o'clock to rotate [clockwise rotation assumed here] from the position indicated in the figure to point B on the line L.) Thus $Q_s$ (π+2Γ) and the normalized ratio $\hat{Q}_s$(π+2Γ) are given respectively by (for the specific system dimensions illustrated):

$$Q_s(\pi + 2\Gamma) = \frac{\pi + 2\Gamma}{4\Gamma}; \hat{Q}_s(\pi + 2\Gamma) = \frac{Q_s(\pi + 2\Gamma)}{3},$$

with numerical values:

$Q_s$(π+2Γ)~2.23;$\hat{Q}_s$(π+2Γ)~0.74.

It is noted again that the disclosed systems are not limited by a particular physical location of the detector: the detector design may be that of a fixed detector with full 360-degree angular coverage, as in "fourth-generation" CT; or a rotating detector of "arbitrary" shape intersecting the full fan-beam projection, as illustrated by bold dashed line 480 in FIG. 3A.

From the above discussion it is clear that maximum speed gains would be obtained for a system with: Δθ$_s$=4Γ, which in turn requires:

$$\Delta\theta_s = \frac{\pi - 2\Gamma}{N_s - 1} = 4\Gamma.$$

For N$_s$=3 this equation implies:

$$\Gamma_s = \pi/10 \text{ and thus } \frac{R_M}{R_s} = \sin\pi/10 = \sim 0.31.$$

For $R_M$=250 mm this requires $R_s$~809 mm, a long geometry. For such geometry, we get $Q_s$(π+2Γ)=3.0 exactly;$\hat{Q}_s$(π+2Γ)=1.0 exactly.

Here we note that a half-scan optimized system with three x-ray sources, a factor three in increased half-scan acquisition speed, and a relative efficiency equal to 1.0 is obtained. In such geometry, there is no projection overlap on the detector.

Figure 10A:
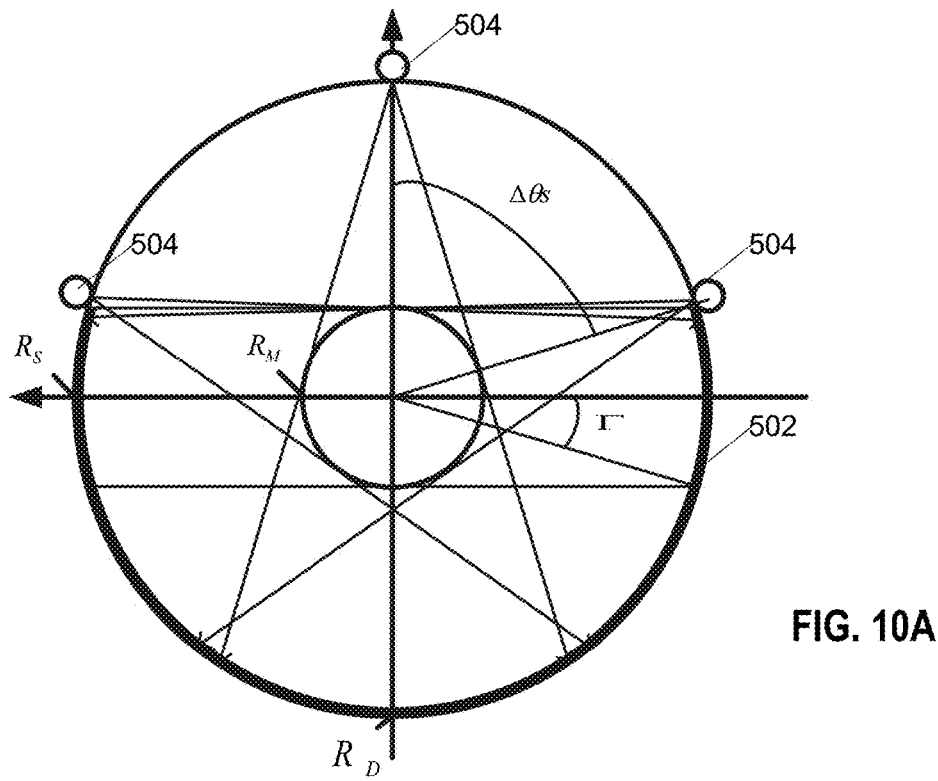
FIG. 10A presents a CT system with three radiation sources in a long geometry optimized for fast and efficient half-scan imaging, according to an embodiment.

FIG. 10A presents a system with such a long geometry. It is interesting to note that the condition Δθ$_s$=4Γ also corresponds to the necessary source spacing such that the projected fan-beams do not overlap on the detector 502; and in principle making room for the radiation tubes 504 to be located at positions that do not interfere with measurement of the projected beams. This applies strictly when the detector distance as defined above is equal to the source radius $R_d \sim R_s$; it can be relaxed somewhat (allowing the sources to be closer in angle and thus a somewhat reduced length geometry) with a detector at a larger distance, $R_d > R_s$. Thus in terms of speed-ratio and avoiding projection data overlap, a long geometry is favorable.

Figure 10B:
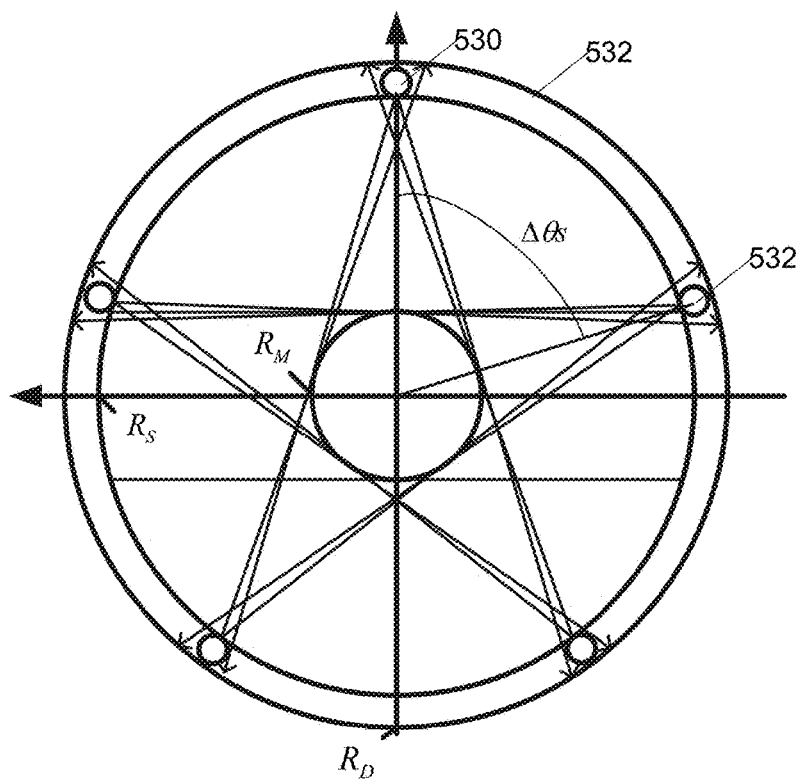
FIG. 10B shows a CT system with five radiation sources equispaced over 360 degrees, in a long geometry, according to an embodiment.

It is noted that for such a long geometry, a system similar to that of FIG. 6 but with five radiation sources equispaced over 360 degrees is possible, without truncation of the fan-beam projections nor overlap of the source projections on the detector. Such a system in shown in FIG. 10B, in a "fourth-generation" geometry, that is with a fixed detector ring 532 and a set of radiation tubes 530 rotating within. For such a system, the following ratios are obtained:

$Q_s$(2π)=5.0 exactly;$\hat{Q}_s$(2π)=1.0 exactly.

Here it is noted that a full-scan optimized system with five x-ray sources, a factor five in increased full-scan acquisition speed, and a relative efficiency equal to 1.0 is obtained.

Further, it is noted that in half-scan optimized geometry (in a CT system with typical medical imaging dimensions), the use of four or more tubes is not advantageous from a speed improvement or efficiency view-point, since the limiting factor then lies with the term $4\Gamma$. Only very long CT geometries would benefit from a fourth radiation tube for improved half-scan speed (when the sources are distributed over an angle $\pi-2\Gamma$ of radians). Below the condition $\theta_s \leq (\pi-2\Gamma)$ radians is relaxed and a near-optimal geometry for $N_s=4$ is obtained.

Figure 11:
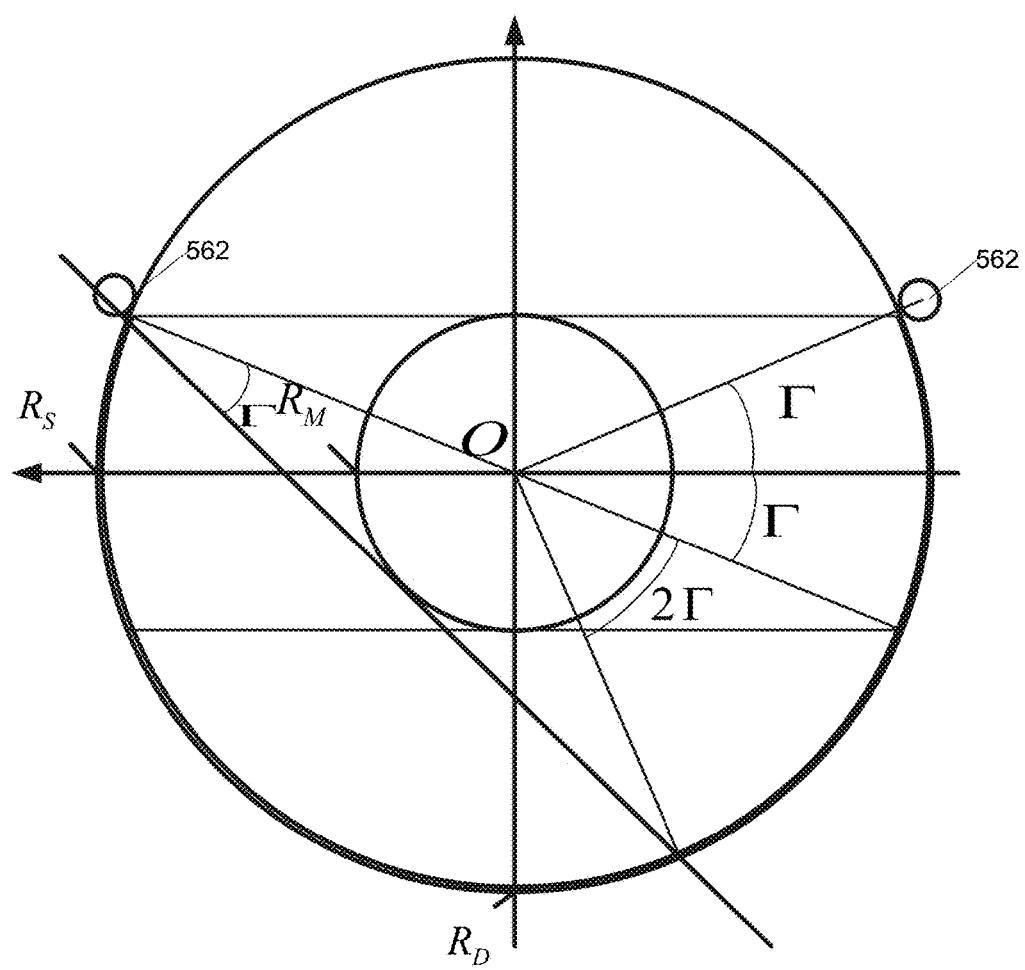
FIG. 11 shows a CT system with two radiation sources in a typical medical CT geometry, according to an embodiment.

FIG. 11 shows an exemplary CT system with two radiation sources 562 in a typical medical CT geometry as above with: $\Delta\theta_s=\pi-2\Gamma\sim2.23$ and $4\Gamma\sim1.82$. In such a configuration, the minimum gantry rotation for complete half-scan data acquisition is given by:

$$\max\{\Delta\theta_s=\pi-2\Gamma,4\Gamma\}=-2\Gamma.$$

Thus $Q_s(\pi+2\Gamma)$ and the normalized ratio $\hat{Q}_s(\pi+2\Gamma)$ are given respectively by:

$$Q_s(\pi+2\Gamma)=\frac{\pi+2\Gamma}{\pi-2\Gamma}; \hat{Q}_s(\pi+2\Gamma)=\frac{Q_s(\pi+2\Gamma)}{2},$$

with numerical values:

$Q_s(\pi+2\Gamma)\sim1.81; \hat{Q}_s(\pi+2\Gamma)\sim0.90.$

Now optimizing these ratios by setting $\pi-2\Gamma=4\Gamma$, we obtain:

$$\Gamma = \pi/6$$

and thus $$\frac{R_M}{R_s} = \sin\pi/6 = 0.5.$$

For $R_M=250$ mm, this requires $R_s=500$ mm, a short geometry. For such geometry we get:

$Q_s(\pi+2\Gamma)=2.0$ exactly and $\hat{Q}_s(\pi+2)=1.0$ exactly.

Here it is noted that a half-scan optimized system with two x-ray sources, a factor two in increased half-scan acquisition speed, and a relative efficiency equal to 1.0 is obtained in a short geometry.

Figure 12:
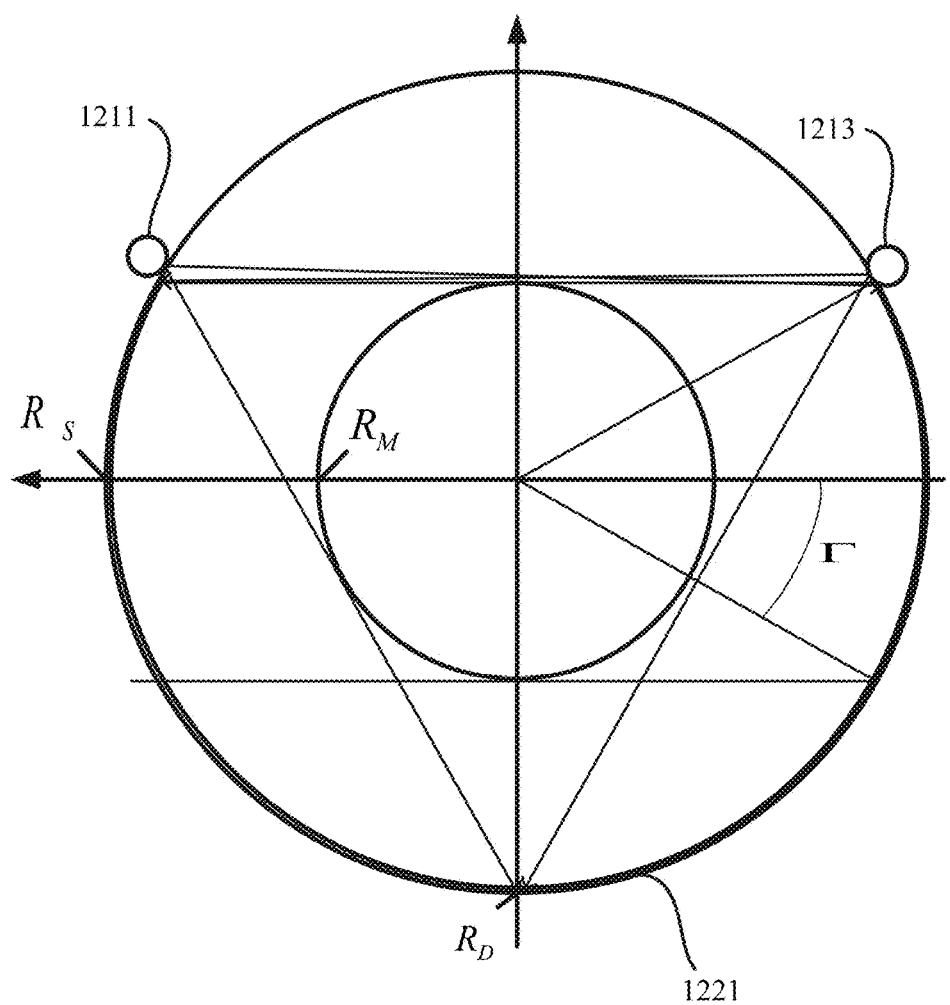
FIG. 12 illustrates a CT system with two radiation sources in a short geometry optimized for fast and efficient half-scan imaging, according to an embodiment.

FIG. 12 illustrates a CT system with two radiation sources 1211 and 1213 in such a short geometry. By construction, the two projected beams do not overlap on the detector 1221.

Figure 13:
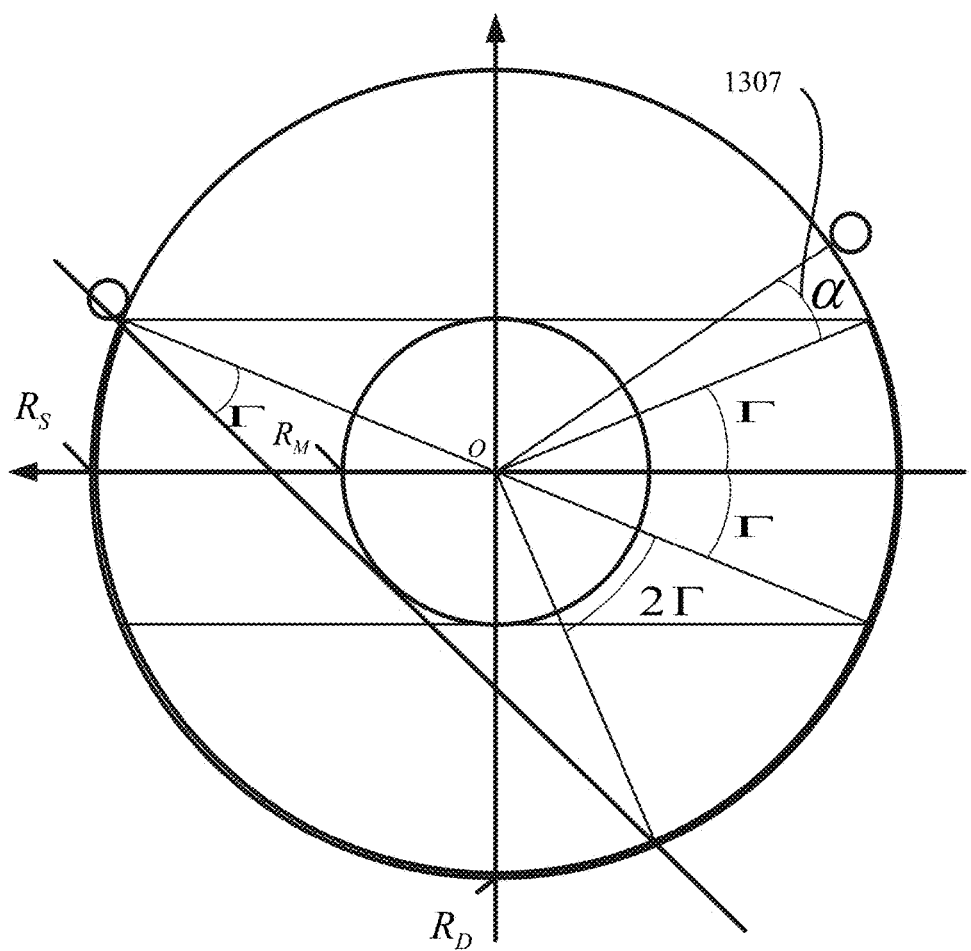
FIG. 13 describes a CT system with two radiation sources in a geometry typical of medical CT imaging with an angular offset $\alpha$ introduced between the two sources and optimized for fast and efficient half-scan imaging, according to an embodiment.

FIG. 13 presents an alternate method of optimizing the scanning times and speed-ups for a system with the geometry and typical medical imaging dimensions of FIG. 11. In this embodiment, an angle offset $\alpha$ 1307 is introduced such that: $\pi-2\Gamma-\alpha=4\Gamma+\alpha$. The associated a values is thus $\alpha=\pi/2-3\Gamma$, with a numerical value: $\alpha\sim0.21$ radians. Accordingly, the optimal source spacing is given by the expression:

$$\Delta\theta_s = \frac{\pi}{2} + \Gamma.$$

(It is noted that $\Delta\theta_s > 2\Gamma$ since $\frac{\pi}{2} > \Gamma$ always.)

Then $Q_s(\pi+2\Gamma)$ and the normalized ratio $\hat{Q}_s(\pi+2\Gamma)$ is given respectively by:

$$Q_s(\pi+2\Gamma)=\frac{\pi+2\Gamma}{\pi-2\Gamma-\alpha}; \hat{Q}_s(\pi+2\Gamma)=\frac{Q_s(\pi+2\Gamma)}{2},$$

with values:

$Q_s(\pi+2\Gamma)=2.0$ exactly; $\hat{Q}_s(\pi+2\Gamma)=1.0$ exactly.

Thus it is possible to optimize $Q_s(\pi+2\Gamma)$ and $\hat{Q}_s(\pi+2\Gamma)$ independently of adjusting $R_m$ and $R_s$, and obtain a factor two increase in half-scan acquisition speed and a relative efficiency factor equal to 1.0 in a typical medical imaging CT dimensions. In the geometry of FIG. 13, the source angular spacing is then:

$\Delta\theta_s=\pi-2\Gamma-\alpha\sim1.78$ radians, or about 102 degrees.

Here it is noted that a half-scan optimized system with two x-ray sources, a factor two in increased half-scan acquisition speed, and a relative efficiency equal to 1.0 is obtained in a typical medical imaging geometry. Because in this geometry, $$\Gamma \sim 0.455 < \pi/6 \sim 0.52 \text{ radians}, \Delta\theta_s = \frac{\pi}{2} + \Gamma > 4\Gamma$$

and the respective sources' beam projections do not overlap on the detector.

Naturally, the offset $\alpha$ may be split between the two sources for mechanical clearance reasons, such as source to detector, or other factors that may apply to the design; and the detector dimensions may be optimized with respect to the sources positions on the source arc.

This approach would apply also in the case of a long geometry ($4\Gamma<\Delta\theta_s$) with three radiation sources. However, in the case of a short geometry ($4\Gamma>\Delta\theta_s$) there is no speed improvement to be gained from this approach; nor is there from increasing the number of radiation sources (i.e., reduce $\Delta\theta_s$), since the constraint lies with the $4\Gamma$ term.

It is noted that in the geometry of the prior art system illustrated in FIG. 8, $R_s\sim595$ mm, $R_d\sim490$ mm, and thus $\Gamma\sim0.434$, leading to an optimized $\Delta\theta_s\sim115$ degrees, which is markedly different from the 95 degrees retained in that system.

Figure 14:
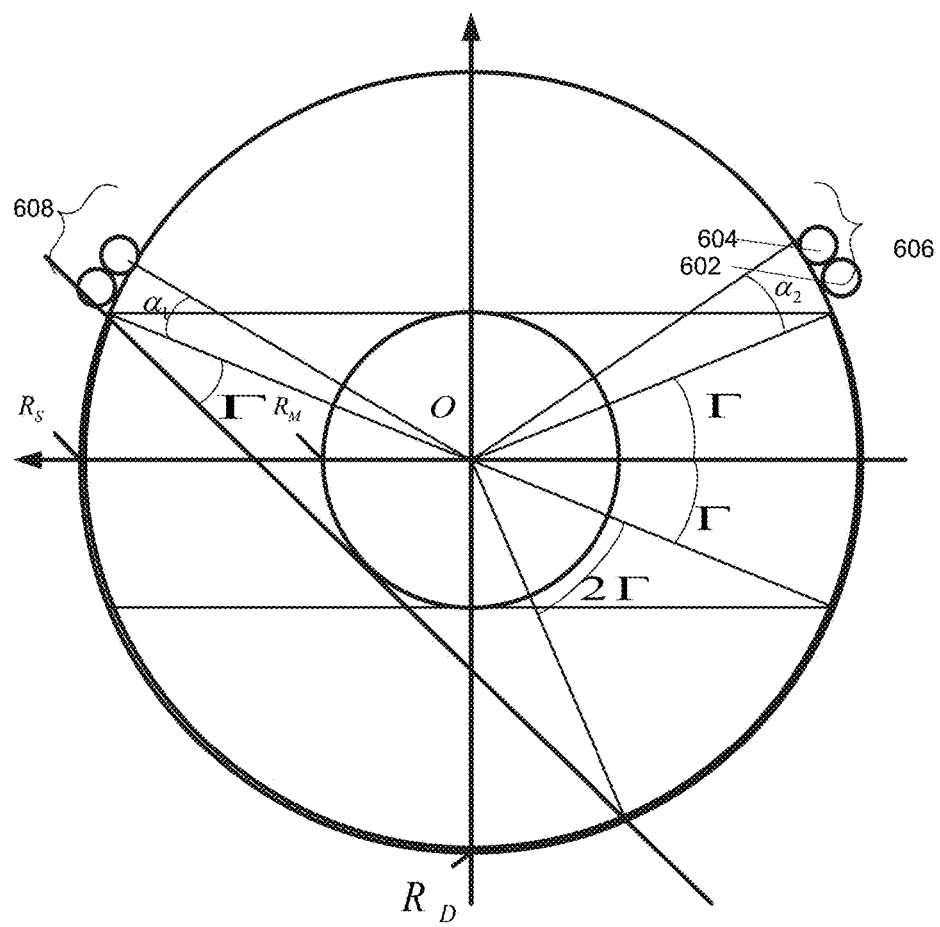
FIG. 14 presents a CT system with two pairs of radiation sources for dual-energy acquisition, with two angular offsets, and optimized for fast and efficient dual-energy half-scan imaging, according to an embodiment.

FIG. 14 presents an alternate embodiment suitable for dual-energy imaging. A system is configured with four sources, such as sources 602, 604, grouped by pairs, such as pair 606, 608; in each x-ray source pair 606, 608 one of the tubes is operated primarily at one energy level (with the other tube in the pair inactive) during the time necessary for acquisition of one or a group of a few projections. Then power to these two tubes is turned off and power to the other two tubes (one in each pair) is turned on. The other two tubes are energized at a different energy level during the time necessary for acquisition of one or a group of a few projections.

Depending on the specifics of the systems being designed, other approaches are possible for dual-energy that do not require a pair of tubes for each x-ray source. All dual-energy approaches known in the art could be implemented in the systems presented in this disclosure, for optimized data acquisition speed and efficiency.

To account for the physical dimensions of the tubes, the offset optimization angle $\alpha$ of FIG. 13 can be split into two components $\alpha_1$ and $\alpha_2$, such that $\alpha=\alpha_1+\alpha_2$ where a is an angle that, at the tube location on the gantry, subtends the exit port centroids of each of the two tubes 602, 604. A similar dual energy arrangement also applies to a modification of the system configuration of FIG. 9, where each of the three x-ray sources is replaced with a pair of x-ray tubes for dual-energy image acquisition.

Figure 15A:
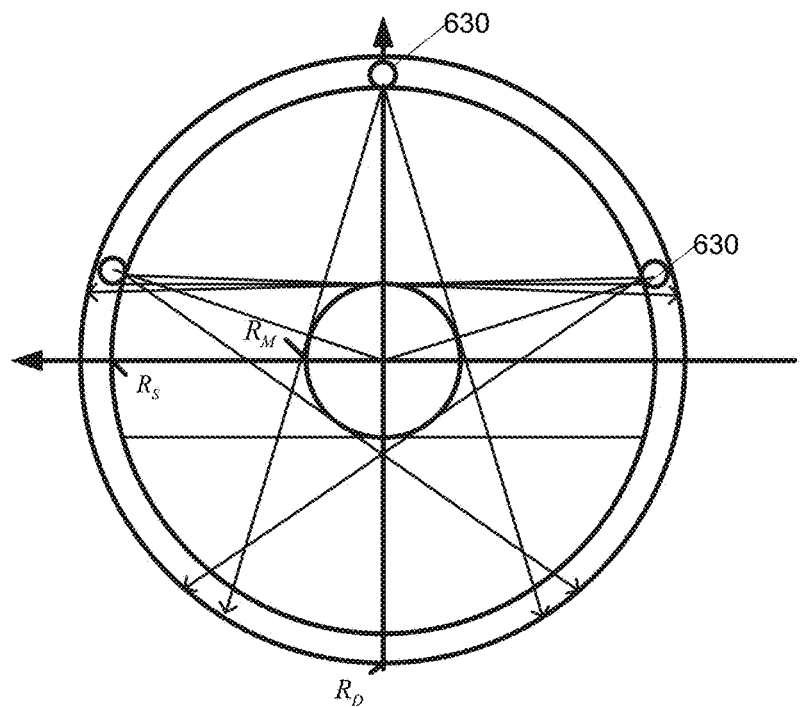
FIG. 15A shows a CT system with at least two adjustable apparatuses, each supporting a radiation source, in a geometry optimized for half-scan acquisition speed and efficiency, according to an embodiment; The apparatuses may be adjusted in between scans, in one embodiment.
Figure 15B:
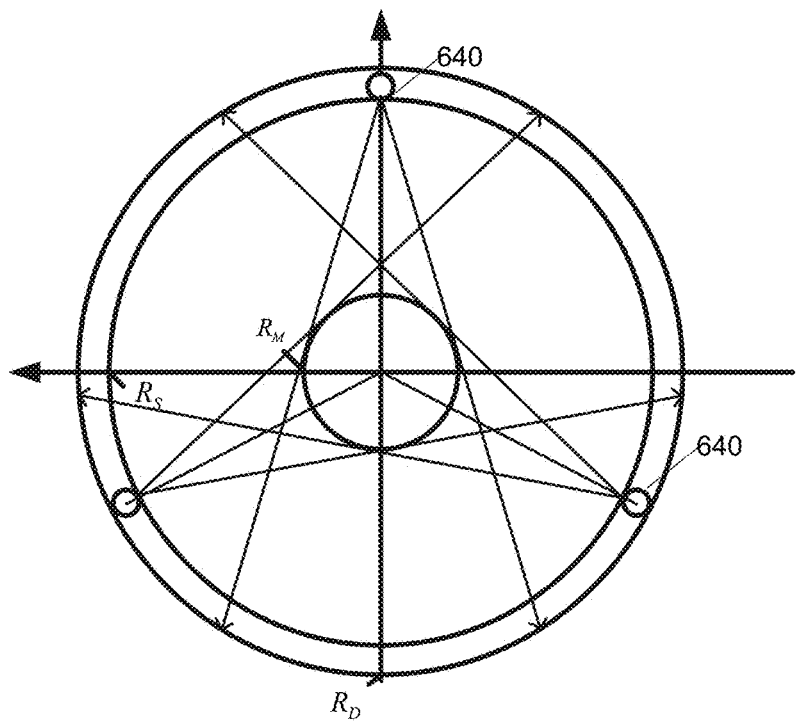
FIG. 15B shows the system of FIG. 13A, where the two adjustable apparatuses have been arranged in a geometry optimized for full-scan acquisition, according to an embodiment.

In a separate embodiment, the detector may be provided on a complete arc covering 360 degrees, and a rotating gantry supporting three sources is designed to rotate within the detector arc. The rotating gantry is provided with mechanically adjustable devices, so that the position of the two or three sources may be optimized for full-scan (equi-spacing of the tubes over 360 degrees) or optimized for half-scan (spacing of the tubes over an arc less than 180 degrees as described above). This is illustrated in FIGS. 15A and 15B, for a system with a geometry similar to that of FIG. 10B, but having three radiation sources 630, 640. Dashed lines represent the adjustable source central angles in the gantry. The configuration of FIG. 15A then corresponds to an optimized half-scan geometry; while that of FIG. 15B is optimized for full-scan geometry.

Distribution of the sources over a central angle of $\theta_s = \pi - 2\Gamma$ is generally preferable, as under this condition all x-ray sources' projections can be fully measured—that is without lateral truncation. Stated otherwise, a detector can be designed such that each of the $N_s$ sources fully illuminates the entire measured-field-of-view of radius $R_M$ (MFOV), and all projection rays intersect the detector and give rise to an associated measurement; under such a conditions, the sources are fully utilized and the fan-beam projections are not truncated.

Figure 16A:
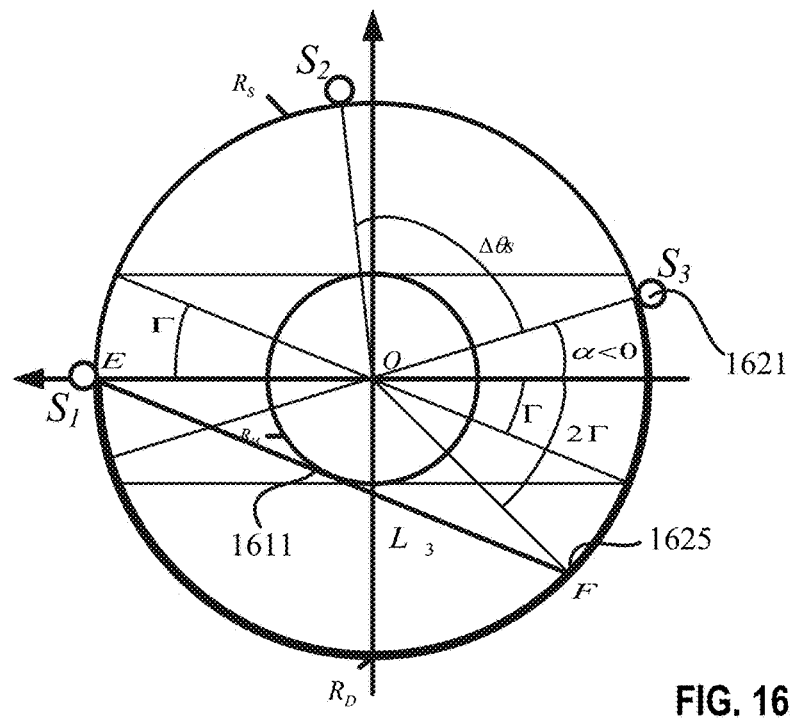
FIG. 16A presents a CT system with three sources equidistributed in an arc covering a central angle of $(\pi+\alpha)$ radians, for $\alpha<0$.
Figure 16B:
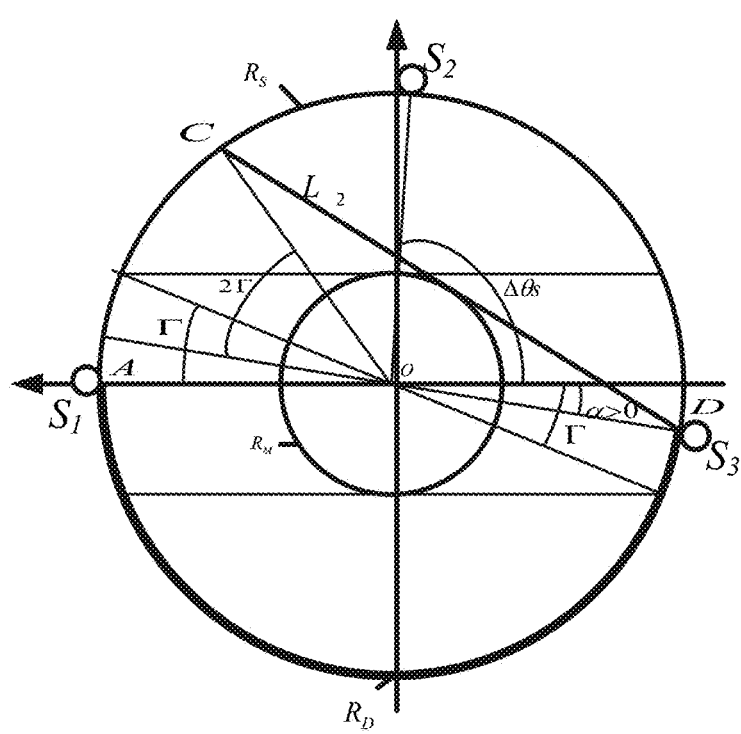
FIG. 16B presents a CT system with three sources equidistributed in an arc covering a central angle of $(\pi+\alpha)$ radians, for $\alpha>0$.

The distribution of the sources for a system having $N_s$ sources equispaced over an angle $\theta_s = \pi + \alpha$ radians and optimized for half-scan imaging is now described. As noted above, for $\alpha > -2\Gamma$ the projections of certain x-ray sources at or near the extreme ends of the angular range may be truncated, i.e. not fully measured due to the fact that certain rays originating at a source and intersecting the MFOV may intersect (at their far end) on within the source angular range; this is illustrated in FIG. 16B, where the central ray originating at $S_3$ intersects the source trajectory between sources $S_1$ and $S_2$. Accordingly, in certain cases, the derivations below provide an upper bound of performance.

It is assumed that the complementary arc (in $2\pi$ radians) of the source arc is substantially fully occupied by the detector arc. Because a measured line integral path necessarily originates at a source and ends at a detector, sources and detector play similar roles in the analysis below—with however the difference that the detector is assumed substantially continuous, as described previously in the context of FIG. 3. However for $\alpha > -2\Gamma$ we have a "deficit of detector."

Case $\alpha < 0$. FIG. 16A shows that to sample line $L_3$ 1611 the system needs to be rotated by $2\Gamma + |\alpha| = 2\Gamma - \alpha$ radians, to bring source $S_3$ 1621 in coincidence with point F 1625. To avoid any source/projection sampling gap, for a complete data acquisition, the system needs to be rotated by at least $\Delta\theta_s$. Thus the minimum gantry rotation is given by:

$$\max\{\Delta\theta_s, 2\Gamma - \alpha\} = \pi - 2\Gamma, \text{ or:}$$

$$\max\left\{\Delta\theta_s = \frac{\pi + \alpha}{N_s - 1}, 2\Gamma - \alpha\right\}.$$

For optimization, setting $$\frac{\pi + \alpha}{N_s - 1} = 2\Gamma - \alpha$$

leads to:

$$\alpha = \frac{2\Gamma(N_s - 1) - \pi}{N_s}.$$

Since $\alpha < 0$ by hypothesis this requires:

$$\Gamma \leq \frac{\pi}{2(N_s - 1)}.$$

Each choice of system F thus determines the maximum number of sources $N_s$ for this optimization to apply. The following equations thus describe the new geometries obtained:

$$N_s \leq \frac{\pi}{2\Gamma} + 1;$$

$$\alpha = \frac{2\Gamma(N_s - 1) - \pi}{N_s};$$

$$\theta_s = \pi + \alpha = \frac{(N_s - 1)}{N_s}(2\Gamma + \pi).$$

Under the medical imaging system dimensions previously described, $\Gamma \sim 0.455$ radians, $N_s \leq 4$ and the following optimized geometries are obtained:

| $N_S$ | $\alpha$ | $\theta_S$ |
|---|---|---|
| 2 | −1.12 | 2.03 |
| 3 | −0.44 | 2.70 |
| 4 | −0.10 | 3.04 |

For $N_s = 2$ the result obtained above is confirmed.

Case $\alpha = 0$. This leads to:

$$N_s = \frac{\pi}{2\Gamma} + 1.$$

To obtain an integer number of sources, this requires in turn:

$$\Gamma = \frac{\pi}{2(N_s - 1)}.$$

These values in turn lead to long geometries.

Case $\alpha > 0$. This case does not appear to lead to interesting results.

Figure 17:
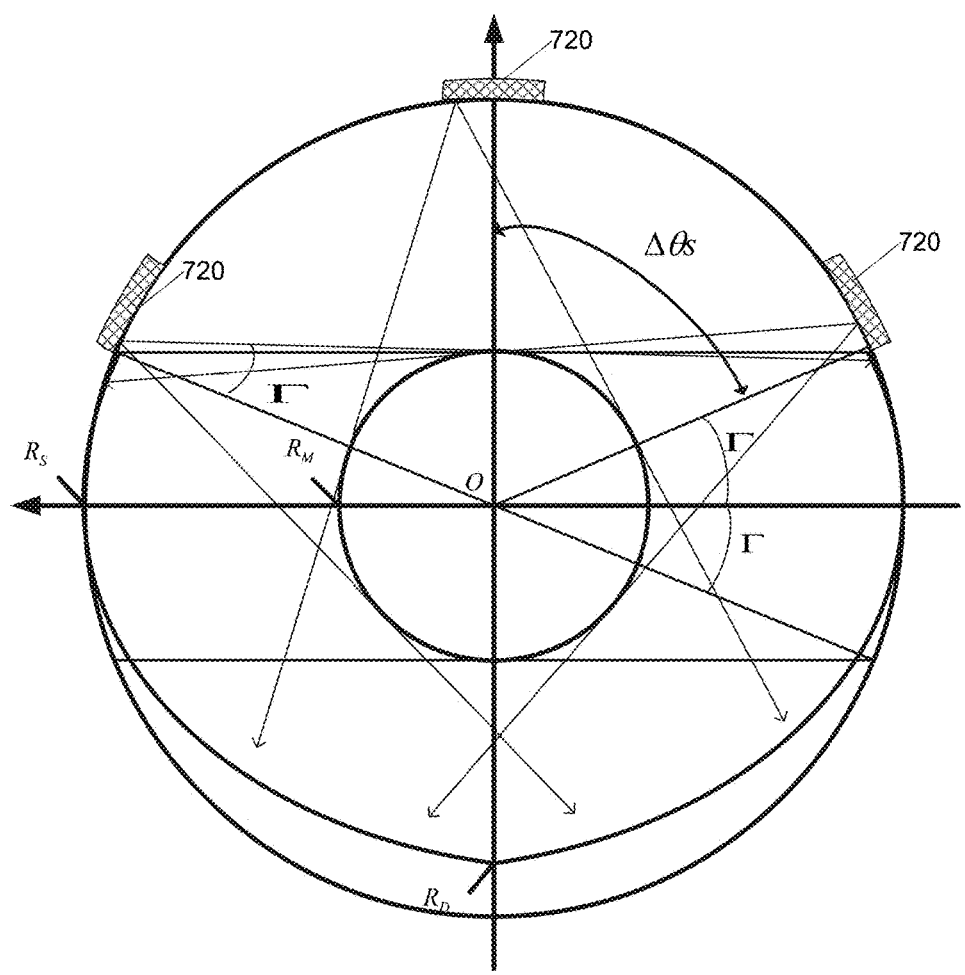
FIG. 17 illustrates a CT system as in FIG. 10A wherein the three sources have been replaced by three arrays of x-ray sources.

The CT system of FIG. 17 is similar to that of FIG. 9, except that the three individual x-ray tubes have been replaced by three arrays 720 of x-ray sources. These may be linear arrays (whether arranged to lie in the plane of the figure, or on a curve in 3D space with orthogonal projection as shown in the figure); or two-dimensional arrays. Different source cells in each of the arrays may be energized at different times.

Figure 18:
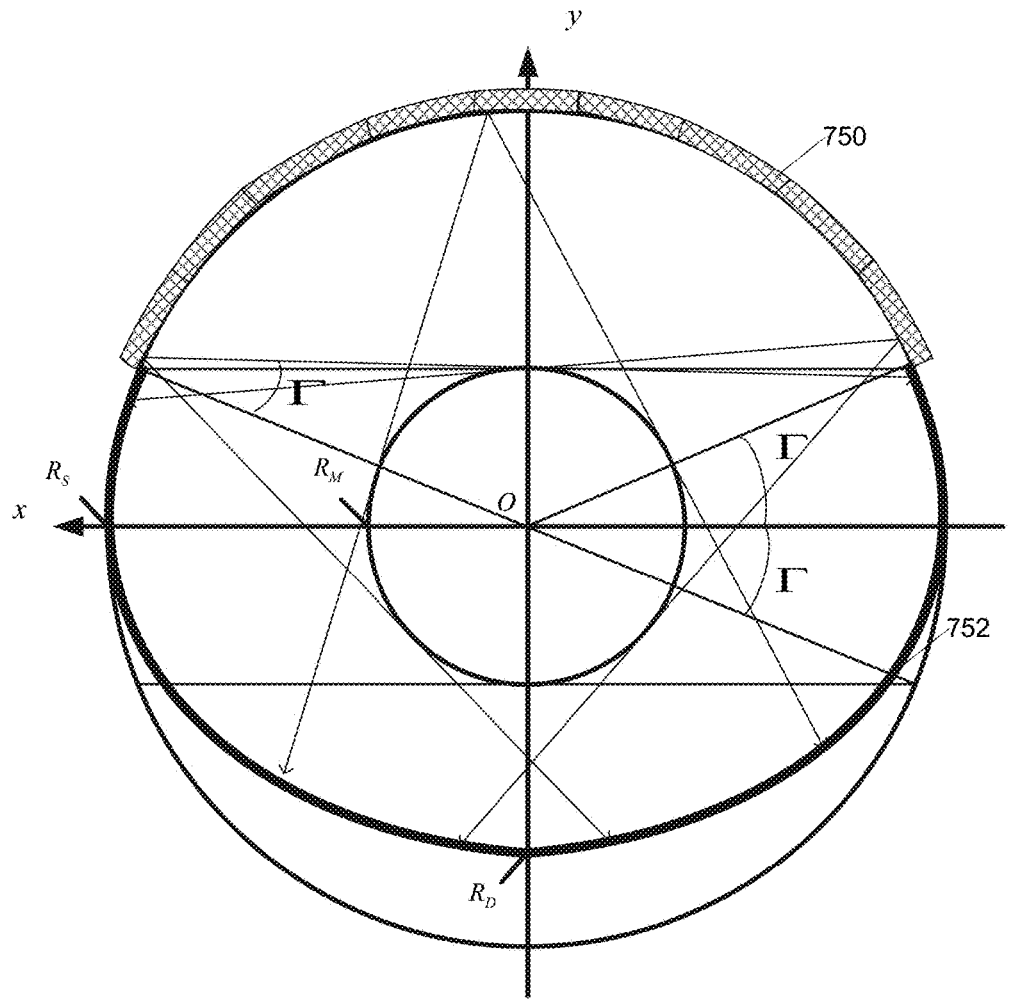
FIG. 18 shows a version of the CT system of FIG. 17 where the three x-ray source arrays have been replaced by a single x-ray source arrays substantially occupying an arc of $(\pi-2\Gamma)$ radians.

FIG. 18 presents a CT system similar to that of FIG. 17 except that the sources 750 are arranged on an array substantially covering a ($\pi - 2\Gamma$) radians arc, and a detector array 752 covers substantially a complementary arc of about ($\pi + 2\Gamma$) radians. As discussed previously in the context of FIG. 16A and FIG. 16B, this geometry generalizes to a set of discrete sources, or array(s) of sources, distributed over a central angle of $(\pi+\alpha)$ radians and a detector array covering substantially a complementary arc of about $(\pi-\alpha)$ radians. Such a design enables energizing the various source array cells in a sequence and allows the simultaneous exposure by a multiplicity of sources with projection overlap.

X-ray attenuation of a thin monochromatic (energy $E=h\nu$ where h is Planck's constant and $\nu$ the frequency of the emitted monochromatic radiation) pencil beam through a uniform slab of thickness L and attenuation $\mu(E)$ follows Beer's law of attenuation:

$$I(E,L,\mu)=I_0(E)\exp(-\mu(E) \times L),$$

where $I_0$ is the intensity of the impinging beam and I is the exiting beam intensity.

In a fourth-generation CT system, where a given detector cell acquires over time a set of data corresponding to one fan-beam projection, the situation is reversed in the sense that time variations in source output, if uncorrected, would introduce ray-to-ray intensity variations as well as possibly spectral artifacts in a single projection.

Figure 19:
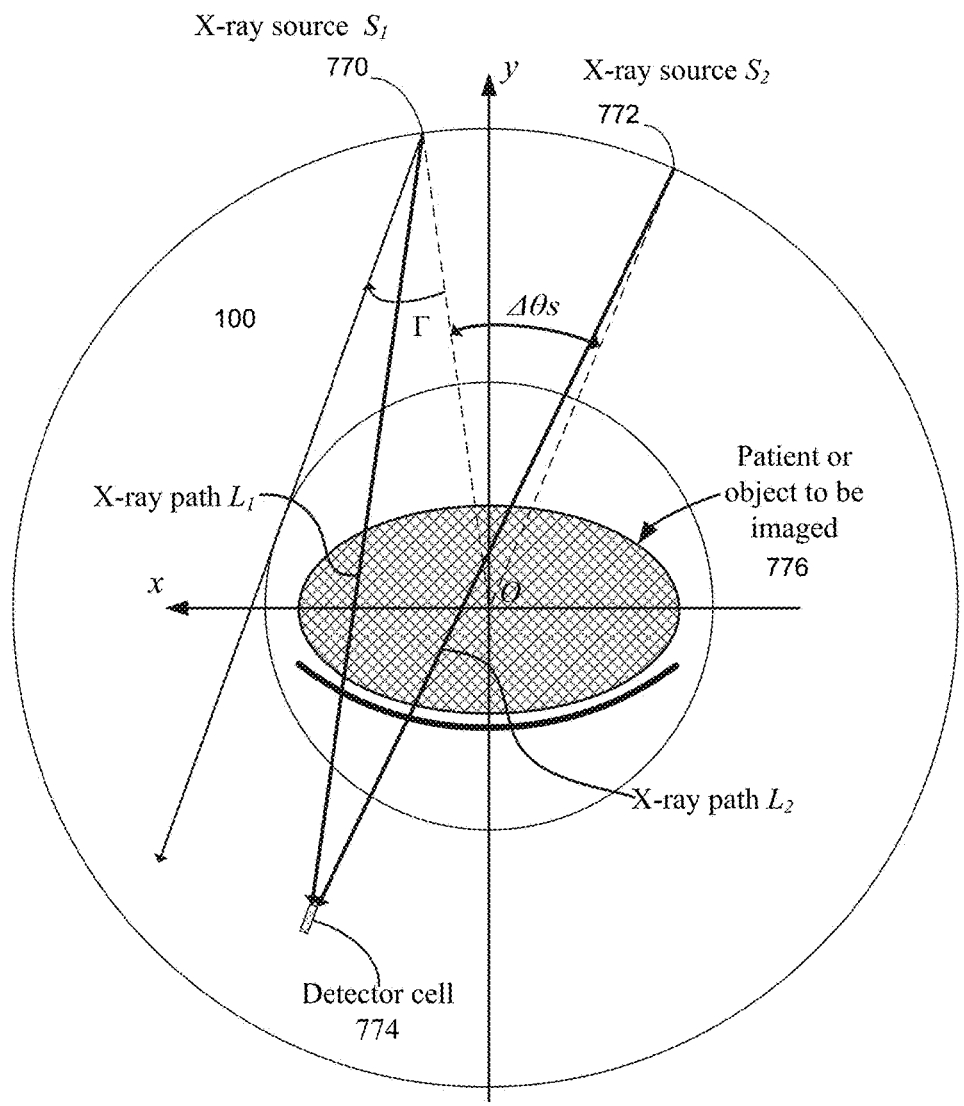
FIG. 19 presents sampling considerations for a CT system wherein at any time two x-ray sources are simultaneously active, simultaneously irradiating an object or patient to be imaged, and the two projections overlap at least in part at the entrance of a detector cell surface (virtual or not).

FIG. 19 presents an x-ray detector cell 774 being simultaneously exposed through a patient or body to be imaged by two spatially separated x-ray sources $S_1$ 770 and $S_2$ 772, at a given moment in time. According to Beer's law, the detected primary beam intensity is then:

$$I=\int_{Energies\ E}\{I_{0,1}(E)\exp(-\int_{Path\ L_1}\mu(l,E)dl)+I_{0,2}(E)\exp(-\int_{Path\ L_2}\mu(l,E)dl)\}dE, \quad (1)$$

where $I_{0,1}$ and $I_{0,2}$ are the intensities impinging on the object 776 from sources $S_1$ and $S_2$ respectively, and $\mu(l, E)$ represents the object's linear x-ray attenuation coefficient as a function of energy E along a path through the body, the paths considered here being paths $L_1$ and $L_2$ respectively from sources $S_1$ and $S_2$ to the detector cell. Since as discussed previously x-ray sources are generally broad-band, an integral over the sources energy E is necessary to most accurately model a measurement.

Figure 20:
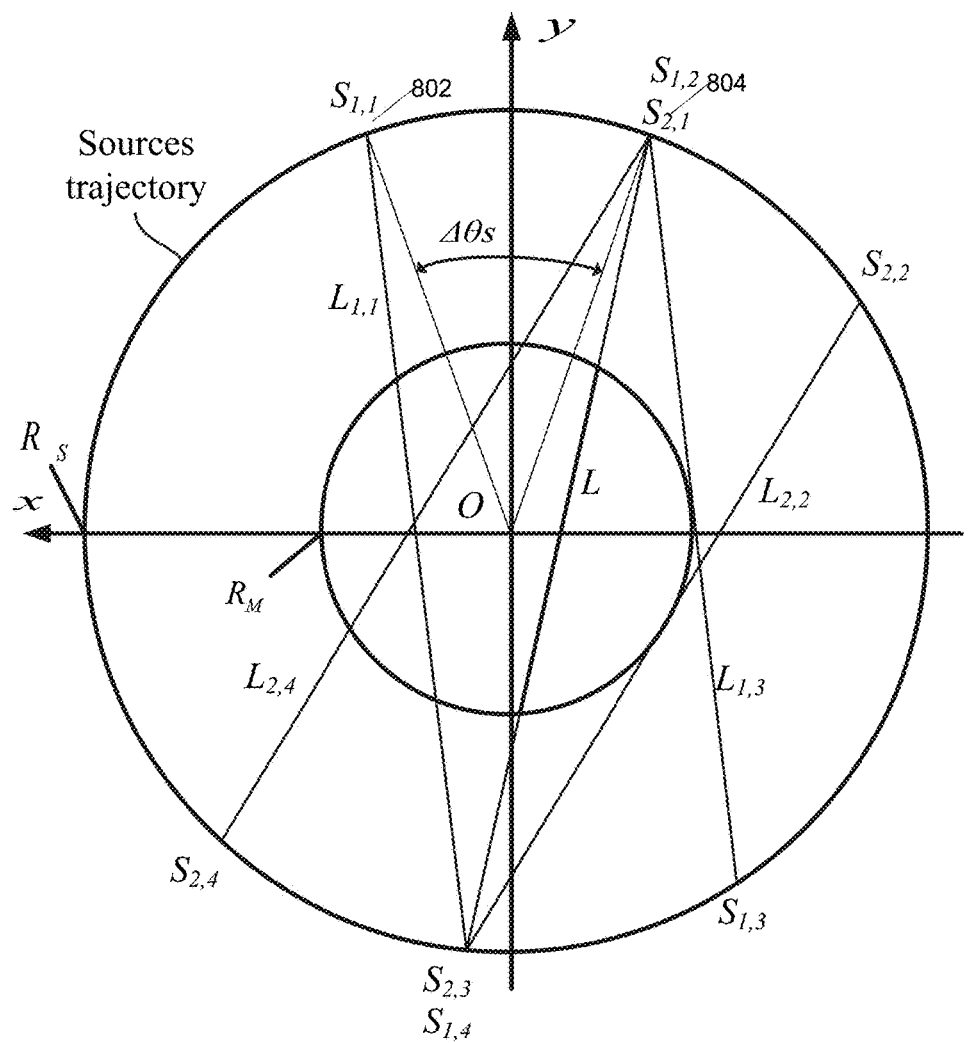
FIG. 20 expands on FIG. 19 to show the sampling of one given line L through the object in time as the source gantry with two simultaneously active x-ray sources separated by a central angle $\Delta\theta_S$ rotates 360 degrees.

In FIG. 20 a CT system with a rotating gantry supporting a detector array (not shown) and two x-ray sources 802, 804 is presented. The geometry is similar to that of a typical third-generation CT system except that two x-ray sources are mounted on the gantry, generally facing the detector. The source positions on the gantry are arbitrary, but in a practical implementation it might be desirable to determine their spatial separation in part by the geometry and extent of the detector array. In FIG. 20, the two sources (which may not be in the plane of the figure) are separated by an angle $\Delta\theta_s$ as measured from the system iso-center (a "central angle" $\Delta\theta_s$). The detector array is not shown in FIG. 20 as its shape is not critical to the description; it is assumed as usual that any x-ray beam through the measured field-of-view originating at one of the provided sources intersects the detector arc on the distal end of the beam. It is understood that the detector shape retained in a system designed for simultaneous exposure by two or more x-ray sources may have a shape, position, and extent specific for the targeted application.

FIG. 20 illustrates the sampling conditions for an arbitrary line L through the object, as obtained after a full $2\pi$ radians rotation of the system. Assuming a clockwise gantry rotation, line L is first traversed by an x-ray beam and gives rise to an associated line-integral measurement when source $S_2$ is at first position $S_{2,1}$. (The notation $S_{i,j}$ means the $j^{th}$ position of source i relevant to the sampling of line L.) Since both sources are by design simultaneously active, the associated x-ray measurement is thus modeled by:

$$I_1(\Delta t_n)=\int_{Energies\ E}\{I_{2,1}^0(E,\Delta t_n)\exp(-\int_{Path\ L(\Delta t_n)}\mu(l,E)dl)+I_{1,1}^0(E,\Delta t_n)\exp(-\int_{Path\ L_{1,1}(\Delta t_n)}\mu(l,E)dl)\}dE, \quad (2)$$

where $I_{2,1}^0$ and $I_{1,1}^0$ represents the sources outputs along the rays as a function of energy E as measured in the absence of object/patient in the system ("air calibration measurements").

Rewriting the above equation with variables $LI(i, j, \Delta t_n)$ representing the respective line-integrals, dropping the $\Delta t_n$ symbols, and with a slight abuse of notation on L:

$$I_1=\int_{Energies\ E}\{I_{2,1}^0(E)\exp(-L)+I_{1,1}^0(E)\exp(-LI(1,1))\}dE \quad (3)$$

We now take the common step as known in the art of re-writing the equation above for an effective energy $E_{eff}$, thus dropping the integral sign:

$$I_1=I_{2,1}^0(E_{eff})\exp(-L)+I_{1,1}^0(E_{eff})\exp(-L/(1,1)), \quad (4)$$

this can be rewritten simply as:

$$I_1=I_{2,1}^0\exp(-L)+I_{1,1}^0\exp(-L/(1,1)). \quad (5)$$

In equation (5) the term L represents the line for which we are interested in obtaining an estimate. The line-integral terms L and $LI(i, j)$ are the unknown, while the source terms $I_{i,j}^0$ are either under control of the system and well characterized by calibration measurements. Writing similar equations for all measurements that involve L, we get the linear system:

$$\begin{Bmatrix} I_1 \\ I_2 \\ I_3 \\ I_4 \end{Bmatrix} = \begin{Bmatrix} I_{1,1}^0\exp(-LI(1,1))+I_{2,1}^0\exp(-L) \\ I_{1,2}^0\exp(-L)+I_{2,2}^0\exp(-LI(2,2)) \\ I_{2,3}^0\exp(-L)+I_{1,3}^0\exp(-LI(1,3)) \\ I_{1,4}^0\exp(-L)+I_{2,4}^0\exp(-LI(2,4)) \end{Bmatrix}. \quad (6)$$

This is a linear system of four equations in five unknown; thus it is a-priori under-determined.

Now considering the sampling that occurs in a full rotation, lets denote by M the number of source projections over 360 degrees (for one source), and by N the number of samples per projection. In a typical medical CT scanner, M is of the order of 1,000 and N is also of the order of 1,000. In the geometry of the proposed system(s) with an extended detector arc, N will be larger, as much as twice the conventional number if the detector arc is twice that of a typical third-generation CT detector. We set the source separation angle $\Delta\theta_s$ such that it is an integral multiple of the source angular sampling $\Delta\theta_v$:

$$\Delta\theta_s = k_1 \frac{2\pi}{M} = k_1 \Delta\theta_v, k_1\ integer. \quad (7)$$

Thus it is not necessary for the sources to equispaced; however, for the sampling conditions described in this document to apply, the central angle between two adjacent sources must satisfy a condition (7).

When condition (7) is satisfied, then the number of source positions around the body remains M; each of those individual source position is occupied at different times by source $S_1$ and source $S_2$ in a complete 360-degree gantry rotation. In CT the angular sampling between detector cells is typically finer than the angular sampling between detector views; typically (although not always) by a factor of about three to four. In the following description we then assume that given lines L as indicated in the figure are indeed sampled multiple times (four times over a full gantry rotation for a system as in the figure). In the geometry of the system of FIG. 20, to obtain samplings for the same line L from source positions $S_{1,2}$ and $S_{2,1}$, we impose that the angular increment $\Delta\eta$ between detector cells measured as a central angle be a divisor of $\Delta\theta_v$:

$$\Delta\theta_v = k_2 \Delta\eta, \tag{8}$$

where, as indicated above, the integer $k_2$ is of the order of 3 or 4 in a typical medical imaging CT system. The conditions (7) and (8) are convenient and represent a preferred embodiment; however if they cannot be realized, it is always possible to interpolate the data either in the fan-direction (cell directions along the detector arc) or in the source-direction; and indeed interpolation is used in most, if not all, CT systems.

Figure 21:
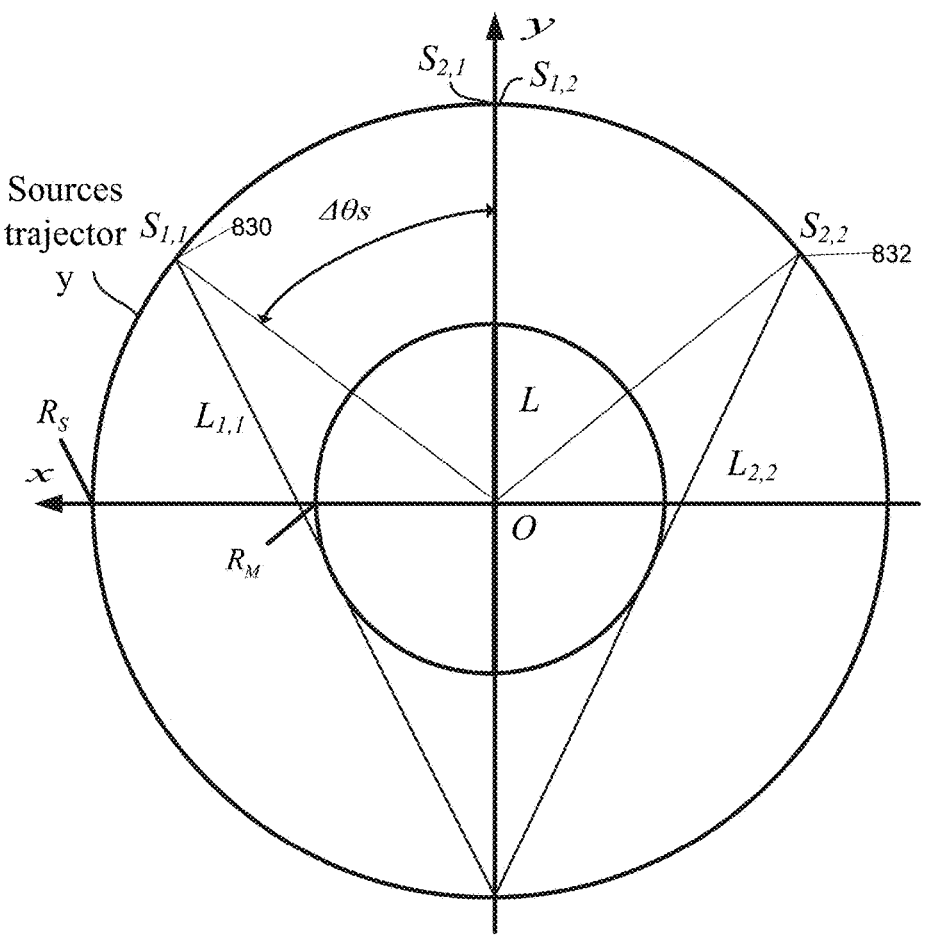
FIG. 21 describes a limiting condition related to the two sources angular separation $\Delta\theta_S$ for the sampling of a specific line L passing through the system iso-center O.

Returning now to a CT system having two x-ray sources (FIG. 21), 830, 832 we investigate conditions under which the linear system generated by equations (6) can be further simplified. Referring now to FIG. 21, we consider the limiting case of a line L passing through the system iso-center. When the source angle separation $\Delta\theta_s$ obeys the condition below, then half of the measurements involve only one of the two sources—the other of the two sources irradiates a path outside the measurement field-of-view (and such a path consists only of air in normal CT operating conditions; and in a properly operating system would be blocked by a source collimator (not shown) if possible):

$$\theta_s = \Delta\theta_s \geq a\sin\left(\frac{R_M}{R_d R_s} \times \left[R_s \cos(\Gamma) + \sqrt{R_d^2 - R_M^2}\right]\right). \tag{9}$$

In the particular case when $R_s = R_d$, this expression reduces to:

$$\theta_s = \Delta\theta_s \geq 2\Gamma. \tag{10}$$

Equation (9) is derived from simple geometry considerations involving a central ray (i.e. a ray from a source through the system iso-center O) and thus the distance $R_d$ of relevance is the distance from O to the detector along such a central ray. The specific of the detector shape are thus to be taken into account; and to derive a relevant condition, it is necessary to consider all the distances $R_{d(i)}$ from the various sources $S_i$ to the detector. Further, for a given source position, we have:

$$\Delta\theta_s = a\sin\left(\frac{R_M}{R_d R_s} \times \left[R_s \cos(\Gamma) + \sqrt{R_d^2 - R_M^2}\right]\right) < 2\Gamma \text{ when } R_d > R_s; \text{ and}$$

$$\Delta\theta_s = a\sin\left(\frac{R_M}{R_d R_s} \times \left[R_s \cos(\Gamma) + \sqrt{R_d^2 - R_M^2}\right]\right) > 2\Gamma \text{ when } R_d < R_s.$$

Thus whenever several differing distances $R_{d(i)}$ are found in a given system design, retaining the value $\min_i R_{d(i)}$ will ensure that an upper bound for $\Delta\theta_s$ for all source intervals is found. In practice this does not present a difficulty since all/most practical detectors are closest to system iso-center at the middle of the detector arc (that is, at a distance associated with the central ray of an actual or virtual source positioned in the middle of the source distribution angular range $\theta_s$).

In the particular case of a detector occupying an arc of the source trajectory, $R_{d(i)}$=constant and (10) is an exact simplified relationship.

It is noted here that the conditions (9) and (10) are specific to a system with $N_s=2$. Generalization to $N_s \geq 3$ is given below.

Figure 22:
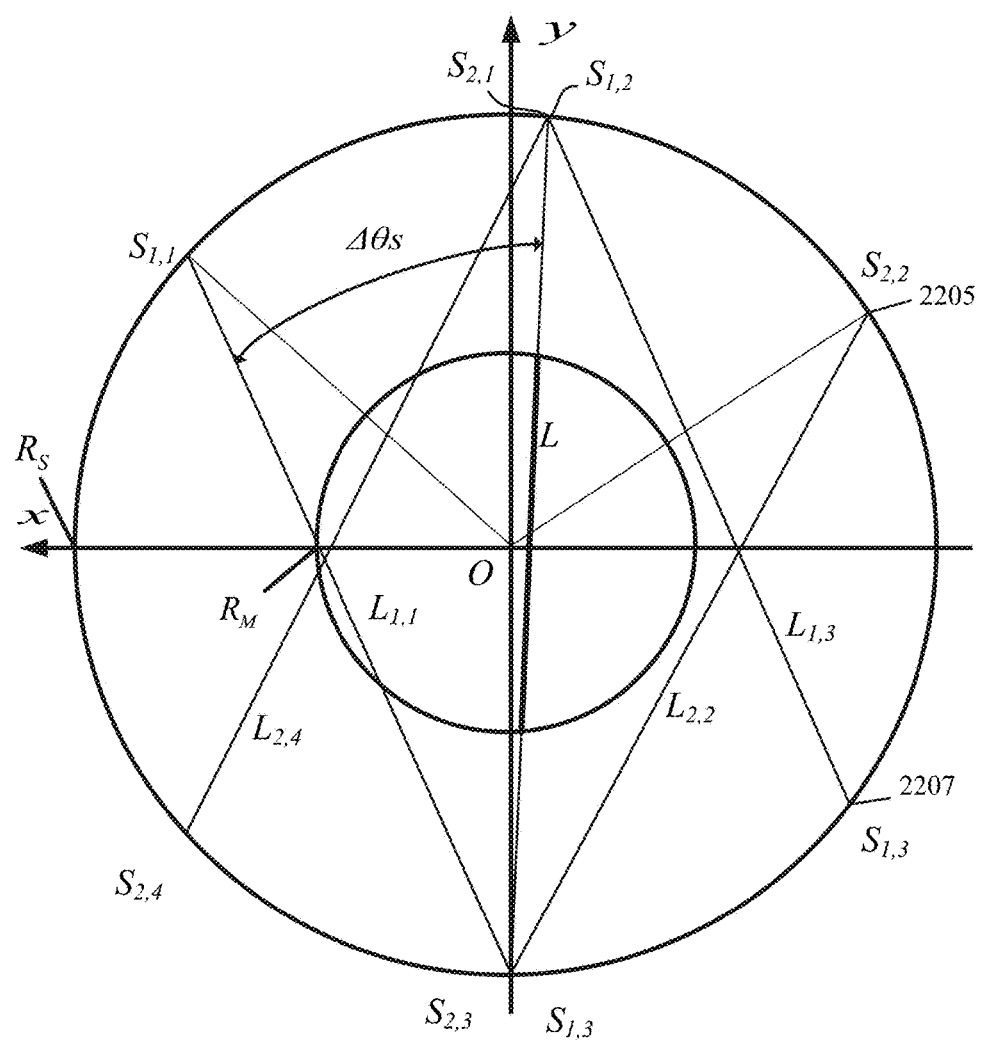
FIG. 22 illustrates the sampling of an arbitrary line L through the object under the separation condition illustrated in FIG. 21.

Under such conditions (9) or (10), and as illustrated in FIG. 22, the measurements associated with sources positions $S_{2,2}$ 2205 and $S_{1,3}$ 2207 are outside the measured field of view and thus system (6) reduces to:

$$\begin{Bmatrix} I_1 \\ I_2 \\ I_3 \\ I_4 \end{Bmatrix} = \begin{Bmatrix} I_{1,1}^0 \exp(-LI(1,1)) + I_{2,1}^0 \exp(-L) \\ I_{1,2}^0 \exp(-L) + I_{2,2}^0 \\ I_{2,3}^0 \exp(-L) + I_{1,3}^0 \\ I_{1,4}^0 \exp(-L) + I_{2,4}^0 \exp(-LI(2,4)) \end{Bmatrix}, \tag{11}$$

A system of four equations in three unknowns; and thus is directly invertible. It is noted that in most cases the lines that lie entirely outside the measured field-of-view would not be exposed to radiation, due to source collimation. Accordingly, with source collimation such that only the measured field-of-view is irradiated by any of the sources, the equations above become:

$$\begin{Bmatrix} I_1 \\ I_2 \\ I_3 \\ I_4 \end{Bmatrix} = \begin{Bmatrix} I_{1,1}^0 \exp(-LI(1,1)) + I_{2,1}^0 \exp(-L) \\ I_{1,2}^0 \exp(-L) \\ I_{2,3}^0 \exp(-L) \\ I_{1,4}^0 \exp(-L) + I_{2,4}^0 \exp(-LI(2,4)) \end{Bmatrix}, \tag{12}$$

a system of four equations in three unknowns; and the system is overdetermined, enabling a better statistical estimate of the unknowns.

The conditions under which we can approximate equation (3) by equation (4) are extensively described in the literature, and mostly consist of beam-hardening and scatter corrections, typically requiring calibration scans with various phantoms approximating the body composition of patients of various sizes. These beam hardening calibrations and corrections are complemented by various artifact reduction methods, such as bone and metal-induced beam hardening; and ad-hoc methods such as streak and ring artifact corrections. The capability of defining x-ray beams with relatively narrow spectral bands, such as in dual-energy or multi-spectral imaging, will make the approximations more rigorous.

Figure 23:
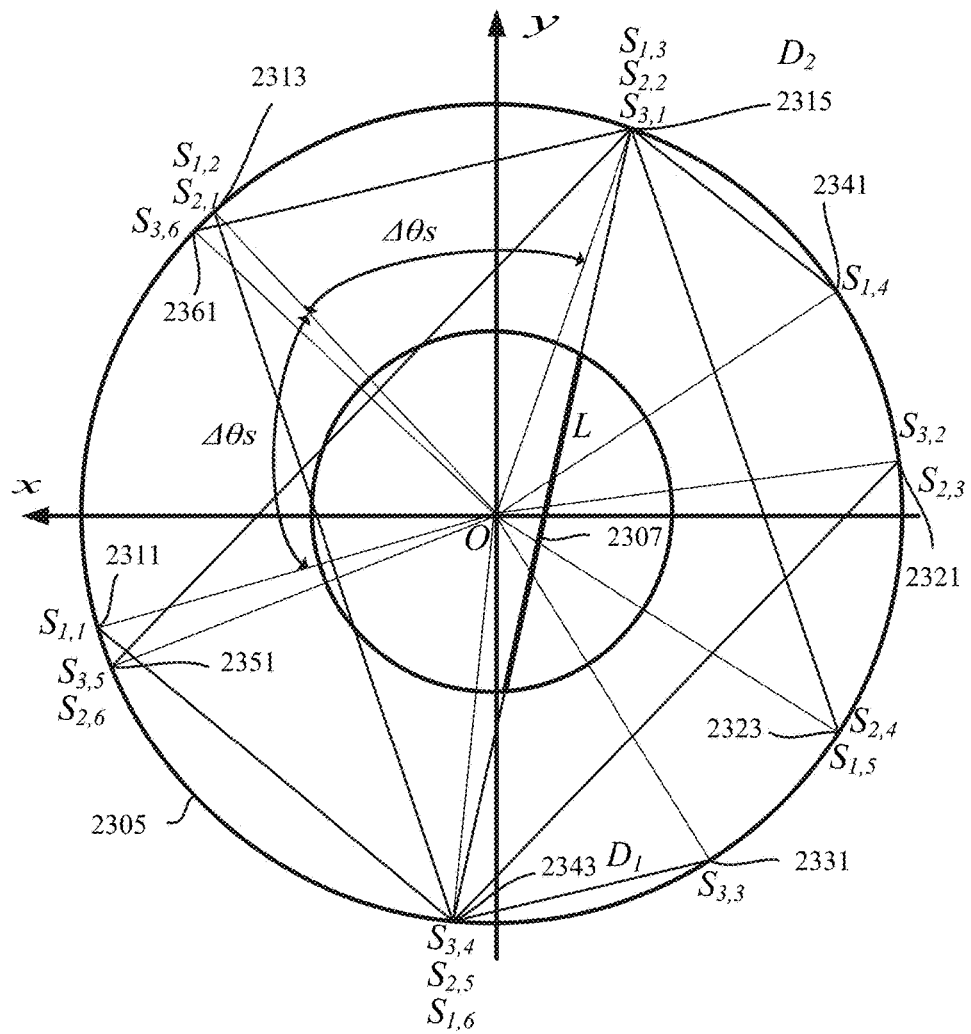
FIG. 23 shows the sampling of an arbitrary line L through the object obtained by a CT system with three x-ray sources distributed over an angle substantially equal to $(\pi-2\Gamma)$ radians, when the gantry undergoes a full 360-degree rotation, under a more general sources separation condition.

In FIG. 23 a CT system with three x-ray sources $S_1$, $S_2$, and $S_3$, distributed over the angle $(\pi-2\Gamma)$ is illustrated, together with the sampling conditions for a given, arbitrary line L through the field-of-view. The sources respective positions when one of them is coincident with the intersection of line L and the source trajectory circle are shown by letters $S_{i,j}$. Because each source intersects line L twice (for a $2\pi$ gantry rotation), there are six such positions for each source; thus $1 \leq i \leq 3$ and $1 \leq j \leq 6$. At time $t_1$ source $S_1$ is at position 2311; source $S_2$ at position 2313; and source $S_3$ at position 2315. At time $t_2$ source $S_1$ is at position 2313; source $S_2$ at position 2315; and source $S_3$ at position 2321. At time $t_3$ source $S_1$ is at position 2315; source $S_2$ at position 2321; and source $S_3$ at position 2331. At time $t_4$ source $S_1$ is at position 2341; source $S_2$ at position 2323; and source $S_3$ at position 2343. At time $t_5$ source $S_1$ is at position 2323; source $S_2$ at position 2343; and source $S_3$ at position 2351. Finally, At time $t_6$ source $S_1$ is at position 2343; source $S_2$ at position 2351; and source $S_3$ at position 2361.

Using typical medical imaging CT dimensions, $R_s$=570 mm, $R_d$=$R_s$, and $R_M$=250 mm, $$\Gamma = a\sin\left(\frac{R_M}{R_s}\right) \sim 0.45 \text{ radians, and } \Delta\theta_s = \frac{(\pi - 2\Gamma)}{2} \sim 1.12 > 2\Gamma,$$

leading to:

$$\theta_s = 2\Delta\theta_s = (\pi - 2\Gamma) > 4\Gamma. \tag{13}$$

As indicated above, equation (13) is a particular case of the more general condition:

$$\theta_s \geq 2\ a\sin\left(\frac{R_M}{R_d R_s} \times \left[R_s \cos(\Gamma) + \sqrt{R_d^2 - R_M^2}\right]\right). \tag{14}$$

Thus the condition of equation (14) is satisfied, and every measurement involves only two active sources/two lines through the object; this is consistent with the observation that in the geometry of the figure, the two extreme source projections do not overlap on the detector. If there is no quarter offset, analysis leads to the following linear set of equations that relate to the sampling of arbitrary line L (in the equations below the gain terms have been omitted for clarity):

$$\begin{Bmatrix} I_1 \\ I_2 \\ I_3 \\ I_4 \\ I_5 \\ I_6 \end{Bmatrix} = \begin{Bmatrix} I_{2,1}^0 \exp(-LI(2,1)) + I_{3,1}^0 \exp(-L) \\ I_{1,2}^0 \exp(-LI(2,1)) + I_{2,2}^0 \exp(-L) \\ I_{1,3}^0 \exp(-L) \\ I_{3,4}^0 \exp(-L) \\ I_{3,5}^0 \exp(-LI(3,5)) + I_{2,5}^0 \exp(-L) \\ I_{1,6}^0 \exp(-L) + I_{2,6}^0 \exp(-LI(3,5)) \end{Bmatrix}. \tag{15}$$

System (13) of six equations in three unknowns is amenable to inversion in the least-squares sense.

In the case of a "half gantry rotation," sufficient to collect data for all lines L, the system (15) becomes:

$$\begin{Bmatrix} I_1 \\ I_2 \\ I_3 \end{Bmatrix} = \begin{Bmatrix} I_{2,1}^0 \exp(-LI(2,1)) + I_{3,1}^0 \exp(-L) \\ I_{1,2}^0 \exp(-LI(2,1)) + I_{2,2}^0 \exp(-L) \\ I_{1,3}^0 \exp(-L) \end{Bmatrix}, \tag{16}$$

and again the system is directly invertible via least-squares methods.

In general it is the case that for a system with $N_s$ simultaneously active sources, when the extreme source projections do not overlap on the detector, then the linear system of equations associated with the measurement is directly and locally invertible, that is, we do not require a full rotation data acquisition to recover the individual line integral estimates. Consider the system of FIG. 24, with $N_s$ simultaneously active sources ($N_s$=10 illustrated). We consider the samplings of an arbitrary line L acquired with such a system. When any of the $N_s$ sources are in the upper part of the plane (above the x-axis), it is seen that under the extreme source separation condition $$\theta_S \geq 2\ a\sin\left(\frac{R_M}{R_d R_s} \times \left[R_S \cos(\Gamma) + \sqrt{R_d^2 - R_M^2}\right]\right) \tag{14}$$

at most $N_s$-2 lines are measured simultaneously with a measurement pertaining to line L; this is because, for a system satisfying condition ( ) (or it's simpler version ( ) for a system such as that illustrated with a detector arc essentially located on part of the source circular trajectories) at most $N_s$-1 lines are traced within the field-of-view of radius $R_M$, including line L. Thus the total number of lines when any source is in the upper half of the plane and one source is in position to sample line L (as source $S_7$ at position $D_2$ is in FIG. 24) is no more than $N_s$-1 (it could be less, depending on the specific of the geometry). Thus a system of $N_s$ equations is obtained, one equation for each source position associated with point $D_2$ in the figure; and the total number of unknown figuring in the system is $N_s$-1. Thus the system is "locally invertible," in the sense described above. Because the line joining $S_1$ and $S_{10}$ in the figure does not intersect the measured-field-of-view of radius $R_M$, we have: $\theta_s < (\pi - 2\Gamma)$ and each source's projection encompasses the full field-of-view (without projection truncation) and thus leads to a full projection measurement data set. Since the condition ( ) is satisfied we have, in the geometry of the figure, $4\Gamma < \theta_s$ (the condition that leads to local inversion of the measurement system of equations).

Thus in the geometry of the figure, we have the following equations, that correspond to a preferred embodiment of the invention:

$$4\Gamma \leq \theta_s \leq (\pi - 2\Gamma). \tag{17}$$

This in turn leads to the geometric constraint:

$$\Gamma = a\sin\left(\frac{R_M}{R_S}\right) \leq \pi/6, \tag{18}$$

which gives and upper bound on $R_S$ as a function of a chosen $R_M$.

In the general geometry case, these equations are respectively:

$$2\ a\sin\left(\frac{R_M}{R_d R_s} \times \left[R_S \cos(\Gamma) + \sqrt{R_d^2 - R_M^2}\right]\right) \leq \theta_S \leq (\pi - 2\Gamma), \tag{19}$$

And a geometric constraint expressed as:

$$\Gamma + a\sin\left(\frac{R_M}{R_d R_s} \times \left[R_S \cos(\Gamma) + \sqrt{R_d^2 - R_M^2}\right]\right) \leq \pi/2, \tag{20}$$

which in the general case needs to be solved numerically.

Now returning to FIG. 23, we observe that during a full 360-degrees rotation of the system, line L will be sampled again from the other side of the gantry; that is, when any of the $N_s$ sources is present in the lower half of the plane (y<0) and at position $D_1$ 2343, then a sampling involving line L is acquired. As described above, no more than $N_s$-1 lines are traced between the sources and the point $D_2$ 2315 (where a detector cell has now moved). Thus again a system of $N_s$ equations in $N_s$-1 unknown is obtained; which as above is locally invertible.

In the absence of detector quarter-offset, or when applying interpolation, it is possible to consider that new measurements indeed involving line L have been obtained; it is thus possible to combine the systems of equations, to obtain a new system of $2N_s$ equations in $N_s-2$ unknown.

When quarter offset is present, then a line L' generally parallel to line L is sampled, at a lateral distance equal to about half the detector cell spacing (this argument is rigorous only for lines passing through the system iso-center O). Thus the measurements of L and L' cannot be co-mingled; then two systems each of $N_s$ equations in $N_s-1$ unknown are obtained, with no common unknown between the two systems. This, as is known in the art, allows improving spatial resolution in CT imaging.

Figure 24:
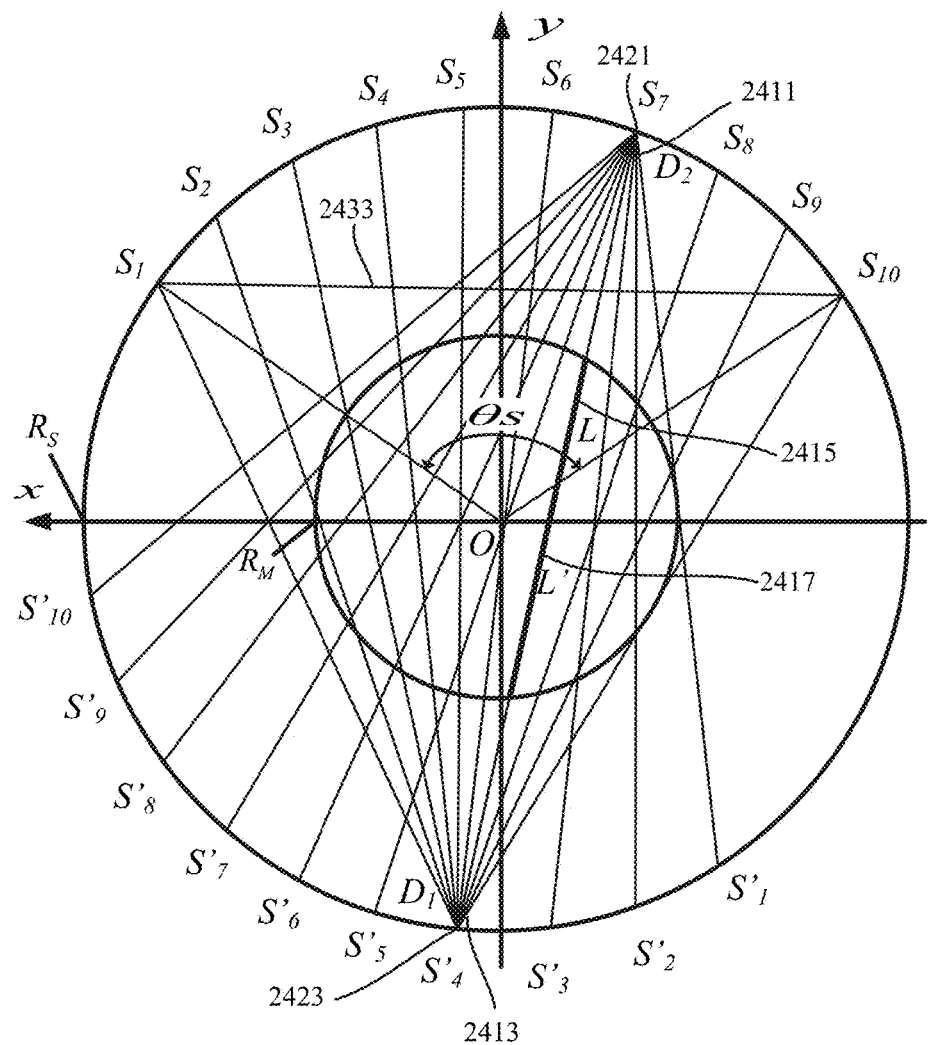
FIG. 24 shows the sampling of a given line L by a system having $N_s=10$ sources, under the more general source separation condition.

In FIG. 24, the line bundles 2411 and 2413 associated to a specific line L 2415, otherwise arbitrary, are shown, for a $2\pi$ gantry rotation of a system with $N_s=10$ radiation sources generally arranged on a central angle equal or less than $(\pi-2\Gamma)$ radians (this is shown by the fact that the line 2433 joining source $S_1$ to source $S_{10}$ does not intersect the MFOV). The figure shows two line bundles, bundle 2413 associated with vertex $D_1$ at position 2423 and associated with sources $S_1$ to source $S_{10}$ passage though $D_2$ at 2421 and a second bundle 2411 associated to vertex $D_2$ at position 2421 and corresponding to the data acquisitions related to source position $S_1'-S_{10}'$. This second bundle is really associated to line L' 2417, but under certain conditions these two lines L and L' may be considered to coincide, see below.

Figure 25:
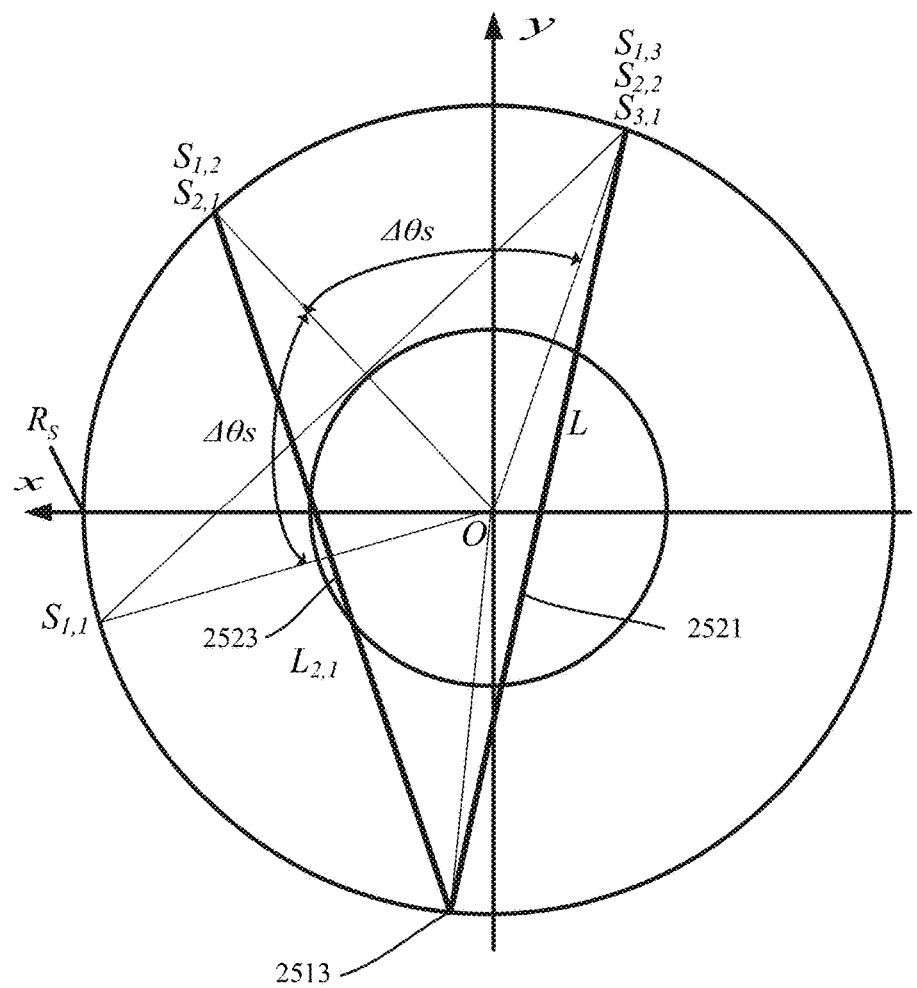
FIG. 25 illustrates the concept of a projection ray bundle for a system with three sources under a general source separation condition.

FIG. 25 illustrates the simpler line bundle 2513 for a system with three simultaneously active sources, $$2a\sin\left(\frac{R_M}{R_d R_s} \times \left[R_S \cos(\Gamma) + \sqrt{R_d^2 - R_M^2}\right]\right) \le \theta_S = 2\Delta\theta_S \le (\pi - 2\Gamma),$$

only two simultaneously overlapping on part of the detector area, and a half-scan data acquisition. In this particular case, the line bundle associated to L is reduced to two line-integrals, L 2521 and $L_{2,1}$ 2523.

Figure 26:
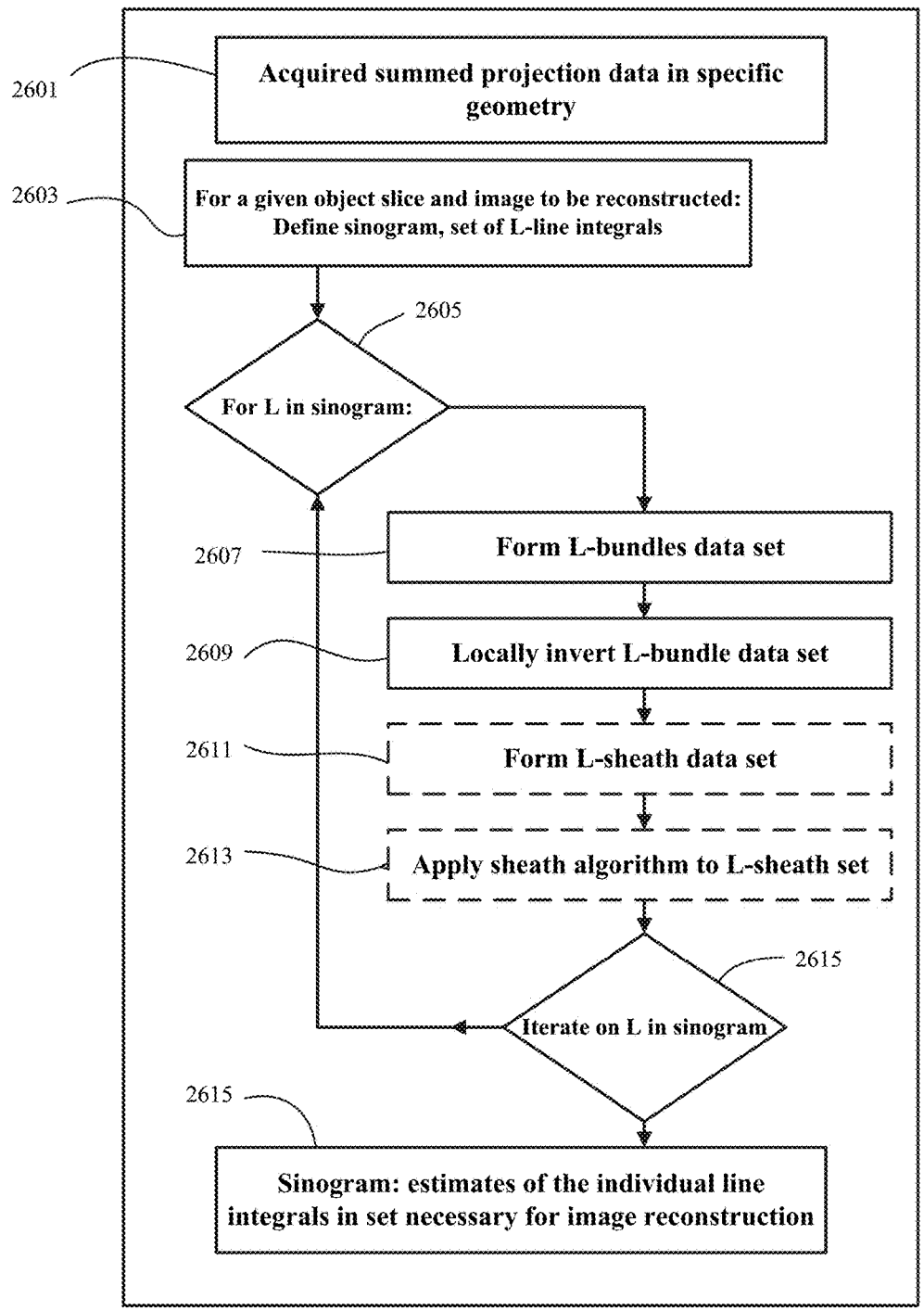
FIG. 26 presents a method to recover the individual line integrals from the summed projection data under the general source separation condition.

FIG. 26 presents a method flow-chart for a "local" inversion algorithm to obtain an estimate of the line-integral L from summed measurements. Only lines belonging to the L-bundle are involved in the system of equations. When linearized, this system of equation presents a number of unknowns that is always less than the number of equations.

FIG. 26 presents a method flow-chart for a "local" inversion algorithm to obtain an estimate of the line-integral L from summed measurements. Under the extreme source central angle $\theta_s$ separation condition of equation:

$$2a\sin\left(\frac{R_M}{R_d R_s} \times \left[R_S \cos(\Gamma) + \sqrt{R_d^2 - R_M^2}\right]\right) \le \theta_S$$

and when the sources in view of the detector span a central angle $\theta_s \le (\pi-2\Gamma)$, the following specific properties apply. The set of lines involved in summed measurements also involving a given line-integral (line for short) L is called the L-bundle.

It is now established that the binary relation defined on the set of acquired line-integrals L that intersect the MFOV:

$$\mathcal{R}: L_1 \mathcal{R} L_2 \text{ if and only if } L_1 \text{ belongs in the } L\text{-bundle of } L_2$$

is an equivalence relation. This applies when only one intersection of the mathematical line that the path L covers with the sources trajectory is considered: That is, the following argument does not take into consideration the possible conjugate measurements that can be acquired when a source is at the position of the other intersection of line L with the sources trajectory; such a conjugate measurement will be associated with its own L-bundle, as further described below, due to either the presence of detector quarter offset or of focal spot deflection, as is known in the art.

(1) Because L always belongs in its own L-bundle, $L\mathcal{R}L$, and the relation $\mathcal{R}$ is reflexive;

(2) If $L_1 \mathcal{R} L$, then there exists a gantry position with a source $S_{i_1}$ such that a ray originating at $S_{i_1}$ and tracing the path of $L_1$ and terminating at a detector cell position d and there exists another source $S_{i_j}$ such that a ray originating at $S_{i_j}$ and tracing the path of L also terminates at cell position d; therefore L is in the L-bundle of $L_1$; and $L\mathcal{R}L_1$. Thus the relation $\mathcal{R}$ is symmetric.

(3) Assume $L_1 \mathcal{R} L_2$ and $L_2 \mathcal{R} L_3$. Then $L_1$ is in the L-bundle of $L_2$ and $L_2$ is in the L-bundle of $L_3$. By construction this means that there exists a gantry position with a source $S_{i_1}$ with a ray originating at $S_{i_1}$ and tracing the path of $L_1$ and terminating at a detector cell position d and there exists another source $S_{i_2}$ such that a ray originating at $S_{i_2}$ and tracing the path of $L_2$ also terminates at cell position d; and, there exists a gantry position with a source $S_{i_2}'$ with a ray originating at $S_{i_2}'$ and tracing the path of $L_2$ and terminating at the detector cell position d and there exists another source $S_{i_3}'$ and a ray originating at $S_{i_3}'$ and tracing the path of $L_3$ and also terminating at the same cell position d. Because the set of line-integrals intersecting the MFOV and terminating at a given, fixed detector cell position span an angle equal or less than $$2a\sin\left(\frac{R_M}{R_d R_s} \times \left[R_S \cos(\Gamma) + \sqrt{R_d^2 - R_M^2}\right]\right),$$

there also exists a gantry position such that there exist sources $S_{i_1}''$, $S_{i_2}''$, and $S_{i_3}''$, with rays originating from these sources and terminating at the same cell position d and intersecting the FMOV. Thus, $L_1$ is in the L-bundle of $L_3$, $L_1 \mathcal{R} L_3$ and the relation $\mathcal{R}$ is transitive.

Accordingly, $\mathcal{R}$ is an equivalence relation. From set theory, this means that the equivalence classes (the L-bundles) form a partition of the set of individual line-integrals L associated with summed measurements and necessary for image reconstruction. That is to say, any given line-integral L belongs to one L-bundle and only one L-bundle set.

Considering an acquired data set for a given object, 2601, the first step consists of defining the slice for which an image reconstruction is required. Given the parameters defining this slice of interest, the method determines at 2603 the set of relevant line-integrals L that will contribute to the tomographic image reconstruction. For any L in the sinogram, 2605, the method then forms the corresponding L-bundle set, step 2607. This is achieved from the knowledge of the system geometry, the number of sources $N_s$, and the parameters of the data acquisition. Once the L-bundle has been determined, the corresponding set of linear equations, with the unknowns corresponding to the exponentials of the negative of the line-integrals in the L-bundle, each weighted by the corresponding source intensity, is inverted at step 2609. As is known in the art, when the linear system consists of more equations than unknown, then a least-squares estimate is obtained as a result of the inversion for the individual line integral L and all the individual line-integrals figuring in the L-bundle.

Accordingly, a step in the inversion algorithm consists of forming, for each measured (measured in as part of a sum) line-integral L intersecting the MFOV, the L-bundle set. Since only lines belonging to the L-bundle are involved in recovering the line-integral L, and since the number of unknown is always equal or less than the number of measurements $N_s$, the linear system of equations associated with each L-bundle is locally invertible, in the least-squares meaning of the term "invertible." It is "locally" invertible, because the recovery of an estimate for line-integral L involves only at most $N_s$ unknowns.

So the next step in the inversion algorithm consists of inverting the linear system associated with the L-bundle, 2609. Optional sheath processing method steps 2611 and 2613 are described below.

In the final step at 2615, the process is iterated over all line-integrals in the sinogram associated with a given slice for which a tomographic reconstruction is sought. When all such line integrals have been examined in turn, the method terminates at 2615, and a complete sinogram comprising estimates for all the individual line-integrals L necessary for a specific image reconstruction has been obtained.

All of the pre-reconstruction inversion method steps described above in the context of L-bundle processing are carried out in the system firmware, block 118 of FIG. 1. This firmware resides within the CT system data and image processor sub-system 114.

Generally, for a given line-integral L and associated path through the MFOV, it is necessary for the acquisition of an L-bundle that all of the system $N_s$ sources pass through the intersection of one specified line path with the sources circle trajectory; the corresponding minimum gantry rotation depends on the specific of a system configuration and location of the line path L within the MFOV, the gantry position at the start of the scan; and the scan total gantry rotation. However, it can be stated that for a $2\pi$ gantry rotation, each of the two line intersections with the source trajectory will be sampled by each of the $N_s$ system sources (in the absence of quarter offset; or, if quarter offset can be ignored); therefore under such a gantry rotation condition, and in the absence of object motion during the gantry rotation, two L-bundles will have been acquired for any line-integral L through the MFOV. The two L-bundles are said to correspond to "conjugate" measurements associated with L.

When a data acquisition is such that for the path associated with a given line-integral L, complete source measurement sets are available corresponding to source positions on both ends of the path (again, ignoring quarter offset), then the corresponding line integral L figures in a plurality of conjugate L-bundles (such as: two conjugate L-bundles for an effective gantry rotation equal to $2\pi$ radians; four for an effective gantry rotation equal to $4\pi$ radians; etc.), then two or more estimates for the line-integral L are available, each associated with its corresponding L-bundle. The collection of the L-bundles, for a line-integral L, forms the L-sheath set.

Figure 27:
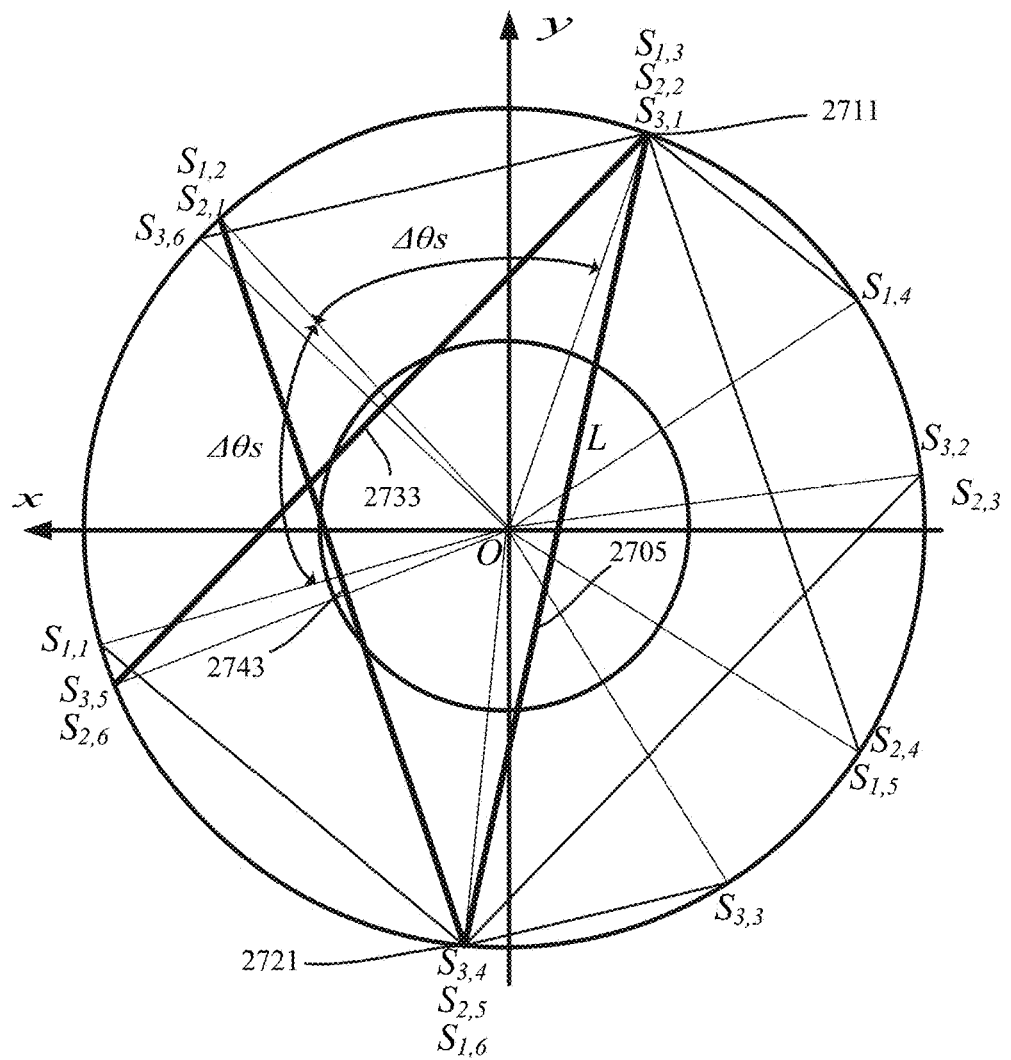
FIG. 27 illustrates the concept of a projection ray sheath formed by a collection of bundles.

FIG. 27 shows the L-sheath associated with line-integral L 2705 for a system data acquisition extending over $2\pi$ worth of gantry rotation. The L-sheath is seen to be composed of the two L-bundles 2711 and 2721 associated with the respective "half-system rotations." For a system with three radiation sources as illustrated in the figure, the first bundle includes a measurement for L and a measurement for a second line-integral 2733; the second L-bundle also has a measurement for L, and a measurement for a third line-integral 2743. The set of equations associated to this L-sheath thus has four rows and three unknowns. Accordingly a redundant estimate for line-integral L is available.

In the case of FIG. 24, two L-bundles are shown for conjugate measurements associated with line-integral L. With $N_s=10$, it is seen that the first bundle comprises L and 8 additional lines; this is also the case for the second L-bundle; thus the L-sheath contains two measurements involving L, and a total of 16 other individual line-integral terms contributing to summed terms. Thus, the system of equations over the L-sheath has 18 rows in 17 unknowns. Again, two separate estimates are available for the line-integral L.

Thus a first sheath algorithm consists of sampling averaging the two estimates, thus reducing the noise contribution by a factor of about square-root of 2.

More sophisticated methods are also available to improve the estimates of line-integral L. For example, the two estimates may be weighted as a function of the total noise in the measurements, which may be estimated separately from standard signal processing techniques; thus a weighted-least-square combined estimate can be formed for L based on the L-sheath.

Further, more sophisticated statistical models such as maximum-likelihood and when a-priori information is available Bayesian approaches may be applied to obtain an improved estimate for line-integral L.

Figure 28:
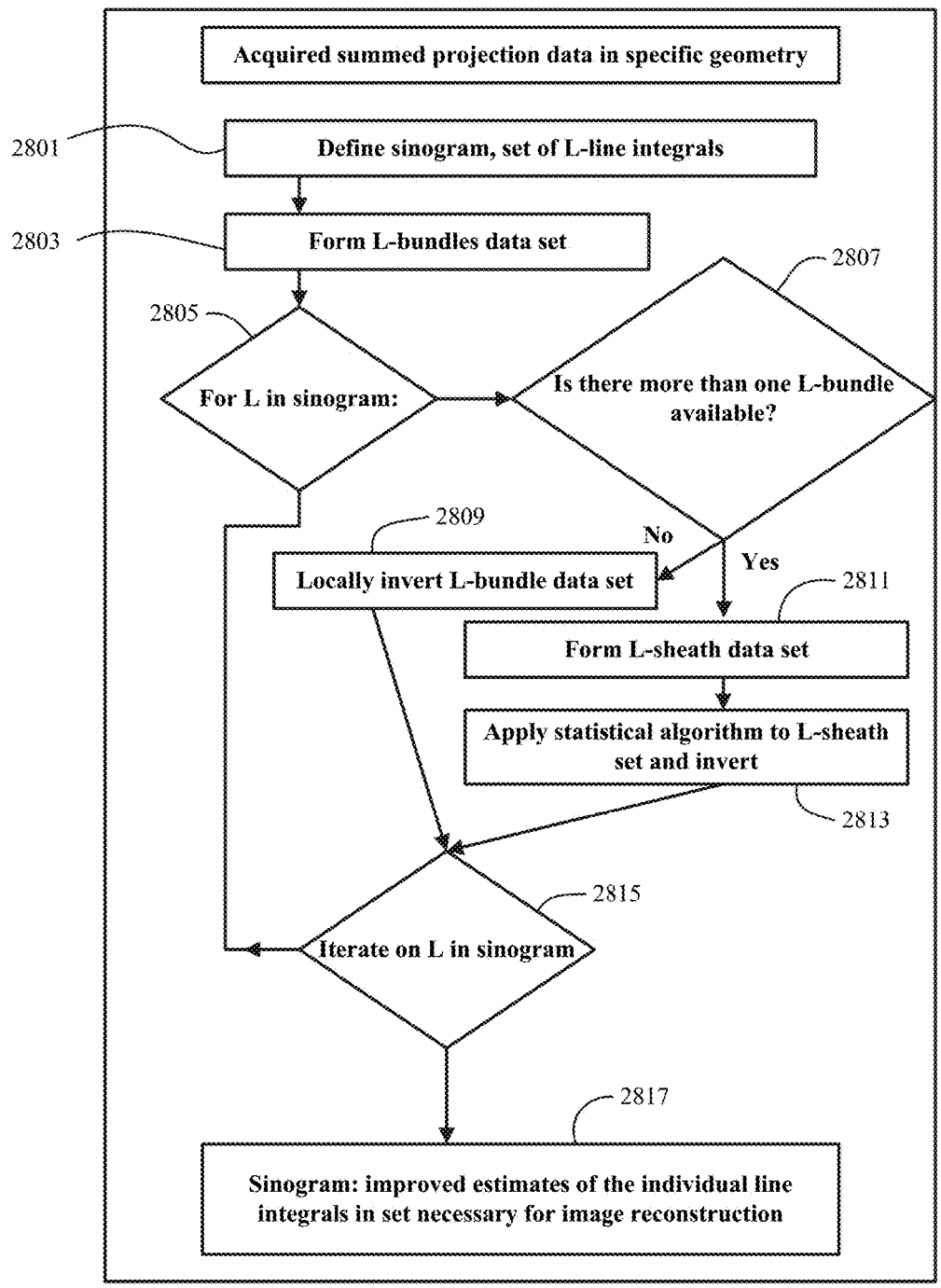
FIG. 28 presents a method to recover the individual line integrals from the summed projection data under the general source separation condition.

Accordingly, FIG. 28 presents a method flow-chart for a "local" inversion algorithm to obtain an estimate of the line-integral L from summed measurements. Only lines belonging to the L-sheath are involved in the system of equations. When linearized, this system of equation presents a number of unknowns that is always less than the number of equations. Given a set of acquired measurements from a CT scan, for a given tomographic image a sinogram set is defined at step 2801. From the sinogram, and given the system geometry and parameters, as well as the parameters of the scan, the L-bundle sets are formed which form partition(s) of the acquired data (ignoring redundant L-bundles such as conjugate L-bundles); step 2803. For each line-integral L in the sinogram, that is every line-integral required for the particular image reconstruction method retained, the method determines at step 2807 whether or not more than one complete L-bundle is available for line-integral L; this determination is based on the specifics of the system configuration, geometry, and data acquisition parameters. In the negative, the method proceeds as previously described at step 2809 with a local inversion of the L-bundle data set. In the affirmative, at step 2811 L-sheath data sets are formed as the collection of the complete available L-bundles for line integral L. Then a statistical algorithm is applied at step 2813 as previously described; the resulting inversion process provides a better estimate for line-integral L: less noisy: more precise, and more accurate, in general. The method iterates at step 2815 on all line-integrals within the sinogram. Every line-integral that figures in an L-sheath is marked as already processed. Thus at step 2817 the method terminates at the end of the iteration of step 2815, and an improved sinogram is obtained for the particular image to be reconstructed.

Generally speaking, and as is known from linear algebra, the inversion of a linear system $Ax=y$ where y is the data vector and x the unknown vector to be recovered, when matrix A is not square, and in particular when A has more rows (measurements) than columns (unknown) is performed by first considering the normal form of the linear system:

$$Ax=y$$

$$A^TAx=A^Ty,$$

where $A^T$ is the transpose of matrix A. Matrix $A^TA$ is always square. When it is also invertible, the solution:

$$x=[A^TA]^{-1}A^Ty$$

corresponds to the least-squares estimate. When matrix $A^TA$ is not invertible, or has a large condition number, the normal system can be regularized, for instance following Tikhonov:

$$x=[A^TA+\lambda I]^{-1}A^Ty,$$

where I is the identity matrix and is a regularization parameter.

These methods apply to inversion of L-bundles linear systems as well as to inversion of L-sheath linear systems.

All of the pre-reconstruction inversion method steps described above in the context of L-sheath processing are carried out in the system firmware, block 118 of FIG. 1. This firmware resides within the CT system data and image processor sub-system 114.

Figure 29:
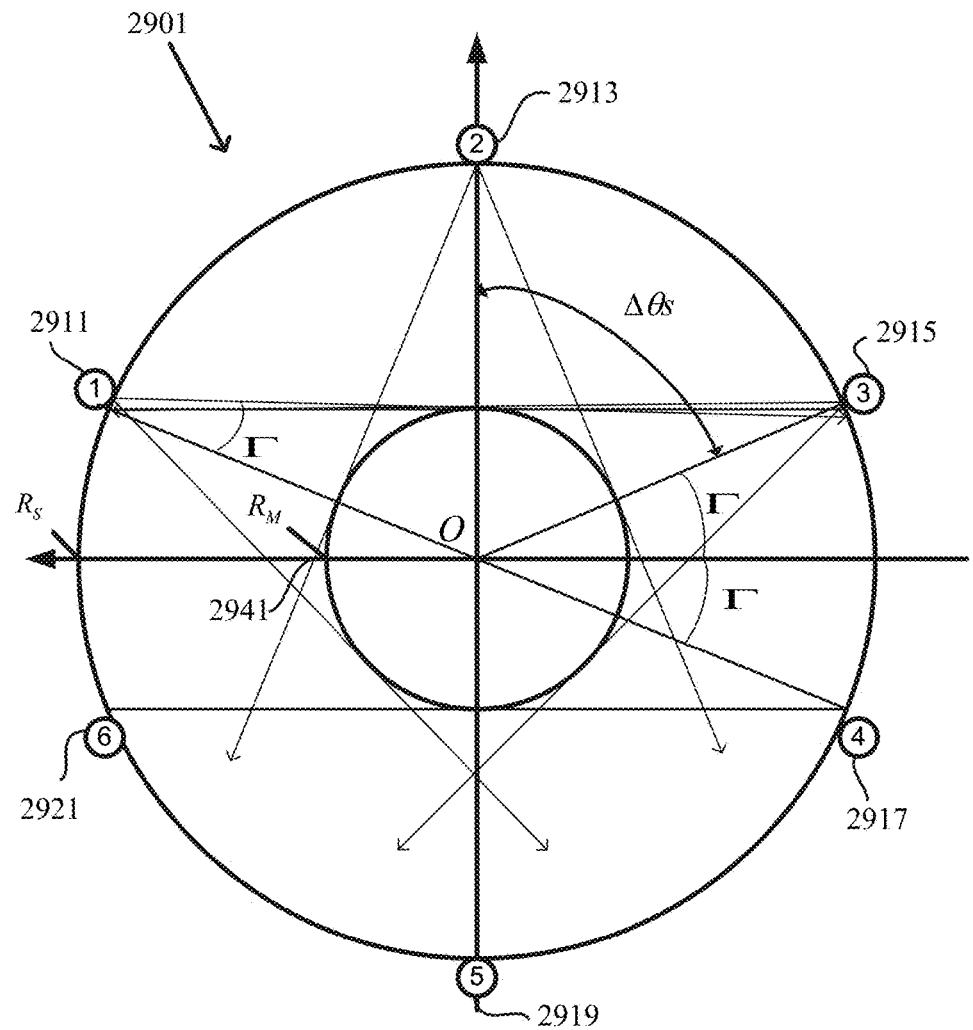
FIG. 29 illustrates a CT system with six radiation sources angularly distributed over 360-degrees, and a detector array substantially covering a full 360-degree range.

FIG. 29 presents a CT system 2901 with six radiation sources ($S_1$-$S_6$) 2911, 2913, 2915, 2917, 2919, and 2921 angularly distributed over 360-degrees, and a detector array substantially covering a full 360-degree range (not shown). The radiation sources and the detector are mounted on the same rotating gantry. Apertures are provided for the six radiation sources through the radiation detector to let the corresponding radiation beams pass there-through and illuminate the object/patient to be imaged. The radiation sources may present offsets in z (the rotation axis) with respect to the gantry central plane. The radius $R_M$ 2941 of the imaged field-of-view may be optimized such that the projections from every other sources do not overlap on the detector (if sources are consecutively numbered 1, 2 . . . 6, as shown, the projections from radiation sources $S_1$, $S_3$, and $S_5$ do not overlap on the detector; nor do the projections from radiation sources $S_2$, $S_4$, and $S_6$). In such a system, appropriate for security imaging and inspection imaging, the sources may be grouped by three; and each group of three sources fired in an alternative sequence, for example.

Figure 30A:
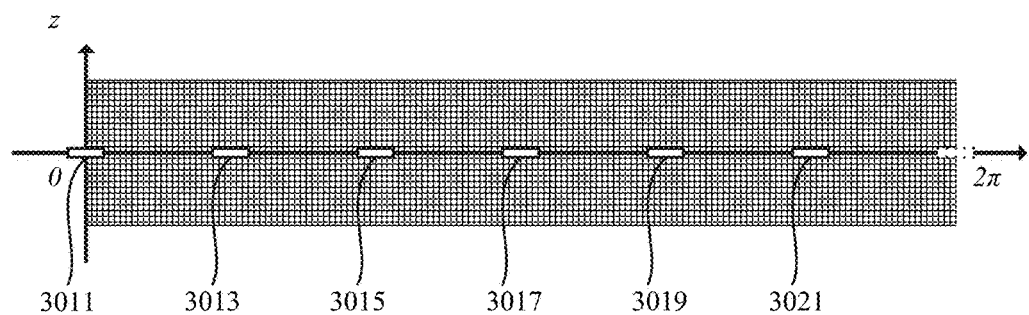
FIGS. 30A, 30B and 30C are partial views of the system of FIG. 29, showing several configurations for the six radiation sources with respect to the gantry and detector array.
Figure 30B:
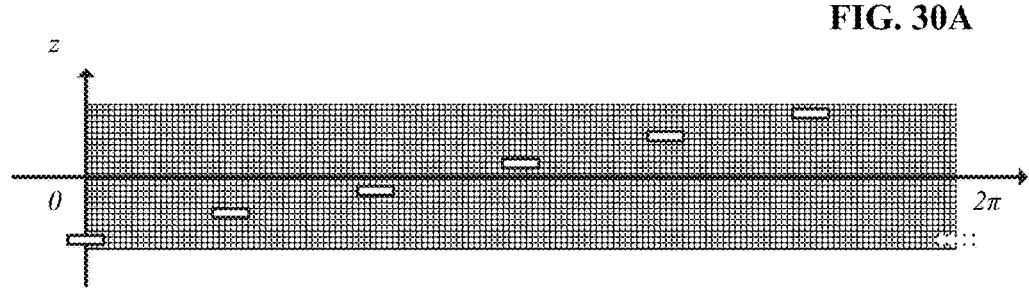
Figure 30C:
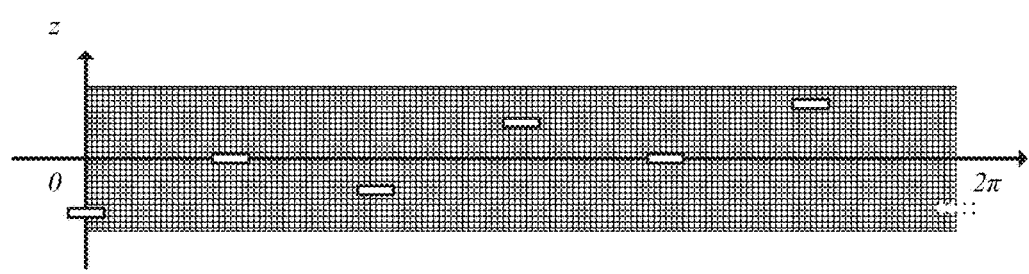

In FIGS. 30A-30C, the entire gantry angular extent for the system of FIG. 29 and as viewed from iso-center is laid out flat on the plane of the figure. Several configurations for the radiation sources and apertures 3011, 3013, 3015, 3017, 3019, 3021 are illustrated in FIGS. 30A to 30C. Although only z-offsets are shown for the apertures, more general arrangements are possible and within the scope of the invention. In one particular embodiment, three radiation sources are simultaneously active, with projected beam possibly non-overlapping on the detector; and the power is toggled in time between two sets of three sources, so as to achieve practical dual-energy imaging. A system per this embodiment would find natural application to security imaging and industrial inspection, in particular. In a security imaging application, where the system pitch, that is the ratio of the advance of the object through the gantry along the rotation axis divided by the detector z-aperture, is fixed, and the z-offsets of the various radiation sources and detector apertures are pre-calculated as part of a specific system design.

In one embodiment, multiple apertures are provided in the detector array, and the sources are re-configurable to expose the object through a specific imaging configuration.

Figure 31:
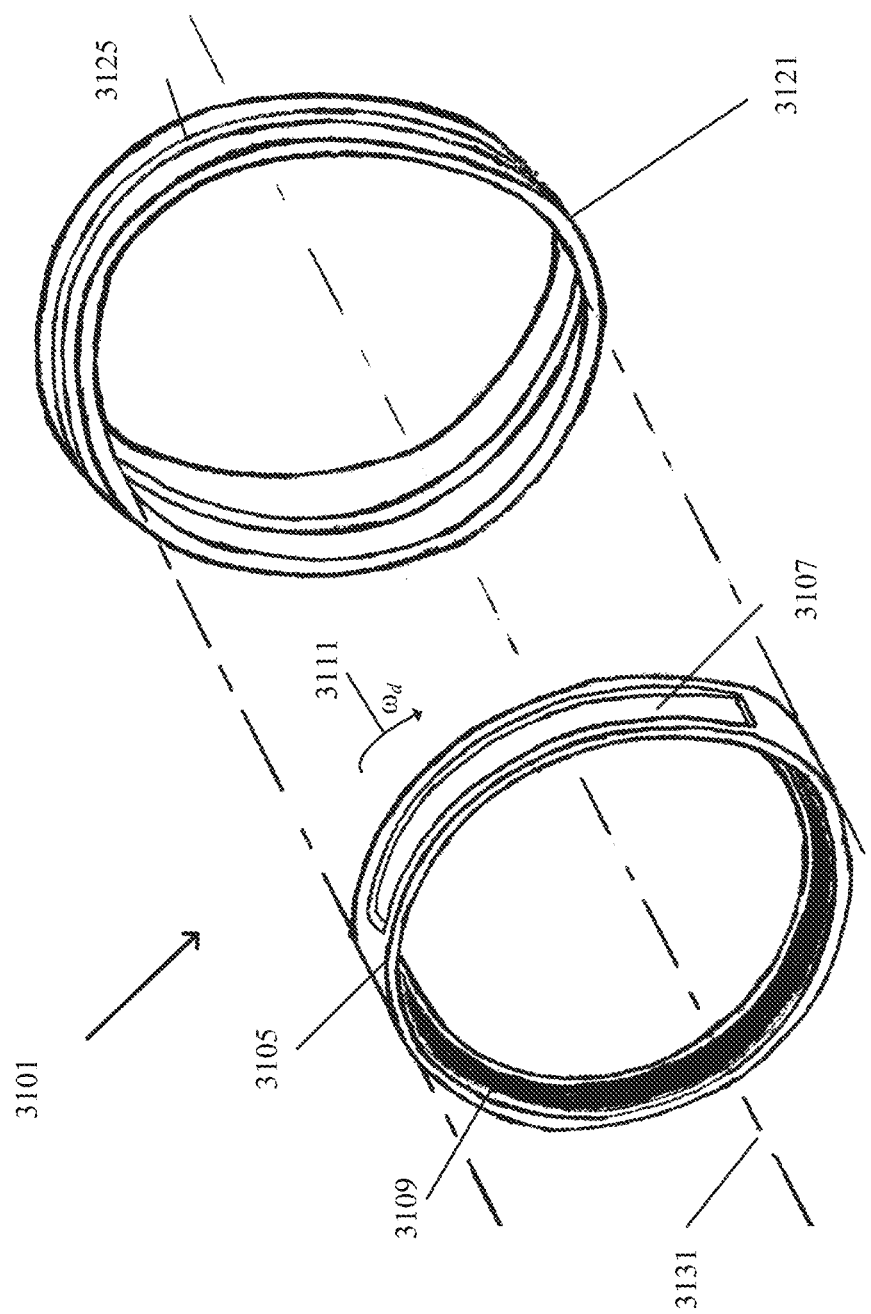
FIG. 31 illustrates the concept of a flying detector for use in either a fixed or a rotating gantry.

FIG. 31 illustrates a flying detector, 3101. In this document, the term "flying detector" refers a detector mounted on the inside surface of a rotating gantry 3105; the rotating gantry being generally cylindrical in shape and centered on the system axis of rotation 3131. The flying detector rotates at angular velocity $\omega_d$, 3111. Angular velocity $\omega_d$ can be positive or negative. In operation, the flying detector rotates inside an external gantry 3121 that supports a plurality of radiation sources (not shown). The flying detector comprises an extended aperture 3107 of dimensions such that x-ray sources arranged on the gantry external to the flying detector can illuminate therethrough over a central angle substantially equal to $(\pi-2\Gamma)$ radians; therefore, depending on the geometry of the system, and the dimension of the outer gantry supporting the sources, the actual aperture 3107 dimensions may differ to some extent from the nominal $(\pi-2\Gamma)$ radians; this aperture 3107 is referred to as the "extended flying detector aperture" or "extended aperture" for short. The outer gantry, supporting the x-ray sources, may be either rotating or fixed in the laboratory reference frame (if it rotates, it can rotate in either direction with respect to the flying detector rotation direction). The external gantry 3121 also comprises aperture(s) 3125 so that radiation sources mounted on the external gantry may expose the imaging field-of-view through aperture(s) 3125 and flying detector extended aperture 3107. The external gantry aperture(s) 3125 may comprise a number of openings, as when the system comprises a few radiation sources and external gantry 3121 also rotates; alternatively, and as shown in the figure, the aperture 3125 can extend substantially throughout the circumference of the external gantry 3121, such as when a fixed external gantry 3121 is provided with multiple source arrays (not shown). The flying detector gantry further comprises active detector cells on radiation detector array 3109 distributed over a central angle substantially equal to the complementary arc in $2\pi$ radians, that is $(\pi+2\Gamma)$ radians. The flying detector may comprise one or a plurality of detector cell rows, generally arranged along the z direction, generally coinciding with the axis of rotation direction. It may comprise other elements as known in the art, including anti-scatter-grids (ASGs); the ASGs lamellas may be arranged in a direction generally parallel to the central imaging plane defined by axes x and y in a plane perpendicular to the axis of rotation 3131. The flying detector may comprise indirect or direct radiation detection elements as known in the art.

Figure 32:
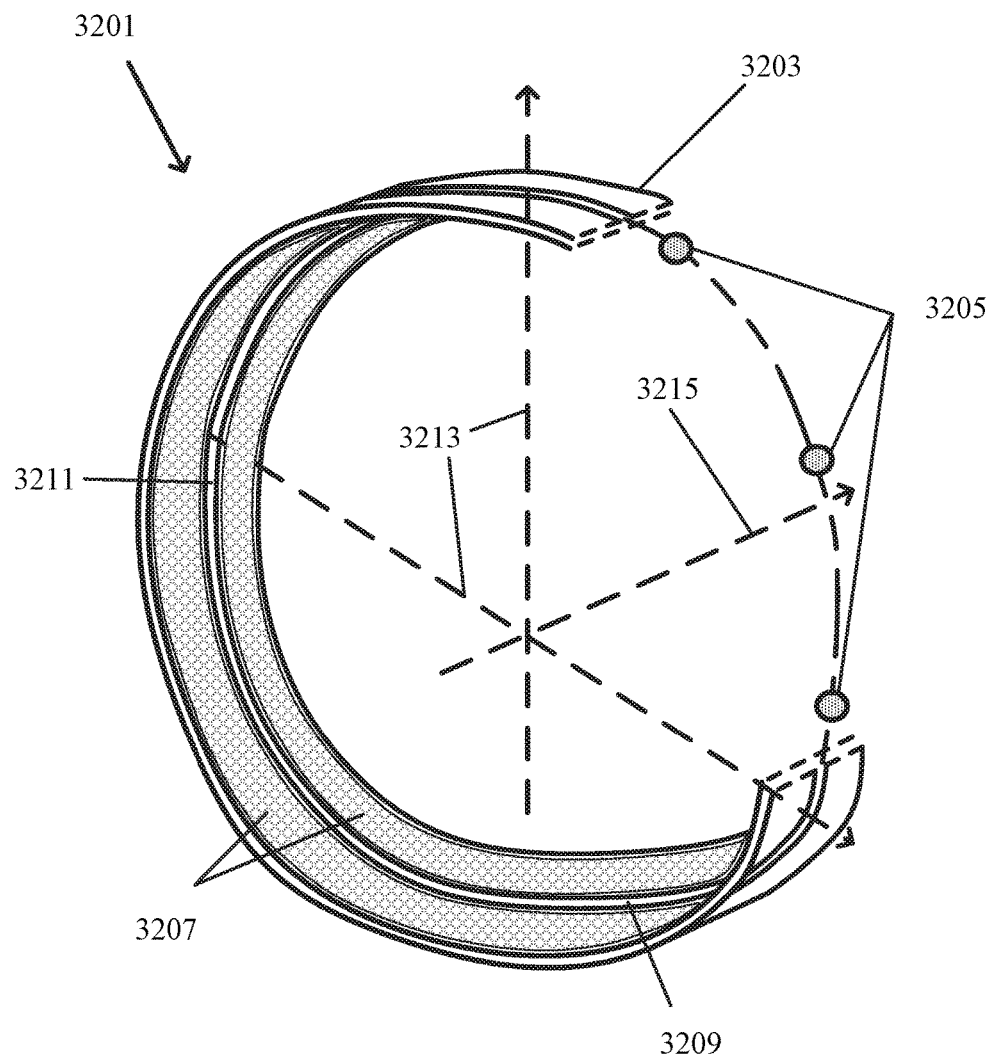
FIG. 32 describes a hybrid 3rd-4th generation CT system with multiple sources per an embodiment of the present invention (illustrated with three x-ray sources).

FIG. 32 presents a hybrid $3^{rd}$-$4^{th}$ generation CT system 3201 with multiple x-ray sources, per an embodiment of the present invention. In FIG. 32, three simultaneously active radiation sources 3205 are illustrated, provided on a rotating gantry 3203. On the rotating gantry 3203 an extended radiation detector component 3207 is provided. In operation, the radiation beams from the simultaneously active radiation sources overlap at least in part on part of extended detector component array 3207. The detector array 3207 presents an extended aperture 3209 in the gantry central plane defined by axes 3213 (x and y) generally orthogonal to system rotation axis 3215 (z). The aperture 3209 extents substantially throughout the rotating detector array 3207 and allows part of respective radiation beams from plurality of sources 3205 to pass through. On the fixed part of the system gantry (not shown), a second detector array component 3211 is provided. The fixed radiation detector component 3211 in one embodiment is provided as a ring array and extends substantially through a 360-degrees central arc, and thus provides detector reading throughout complete system rotations. The fixed detector component 3211 is designed to capture the sources radiation that passes through the rotating detector component 3207 central aperture 3209. In another embodiment, as appropriate for imaging of inanimate objects, the substantially continuous arc of stationary radiation detector cells arranged on fixed arc 3211 can be replaced by a few detector cells distributed at specific central angle intervals (not shown).

Figure 33:
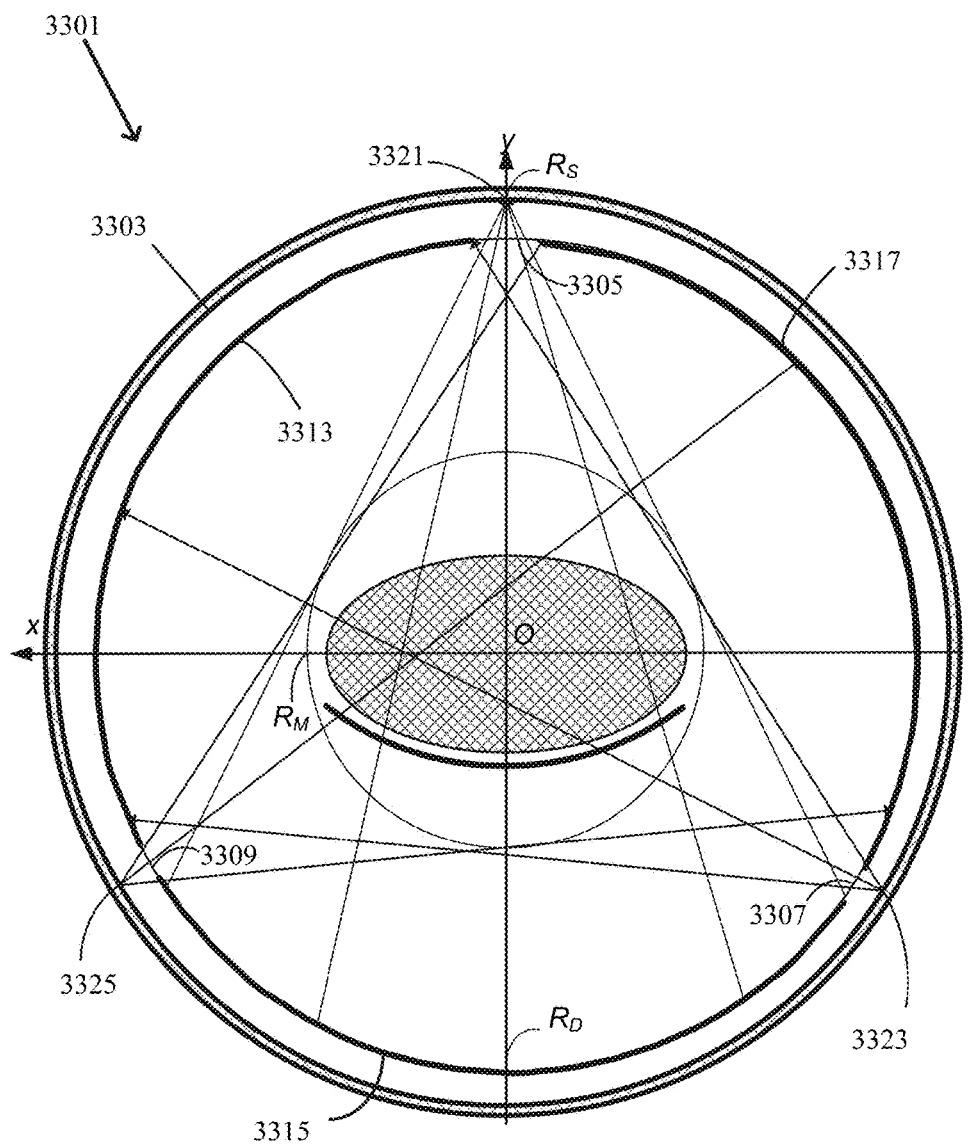
FIG. 33 presents a CT system with a stationary array of x-ray sources and a rotating detector, the detector having three apertures therethrough for optimized full-scan imaging in a system with medical CT dimensions.

FIG. 33 presents a CT system 3301 with a stationary array of x-ray sources 3303 and a rotating detector, the detector comprising three apertures 3305, 3307, and 3309, therethrough for optimized full-scan imaging in a system with medical CT dimensions. The rotating detector thus consists of three separate arrays 3313, 3315 and 3317 rotating together on the rotating gantry. The x-ray sources are mounted as a substantially continuous array on the fixed part of the gantry (not shown). By "substantially continuous" it is meant that there are no gaps in the angular x-ray source distribution significantly larger than the source-to-source pitch in the array/arrays). This geometry enables a factor three speed-up as compared to a single-source CT system in full-scan imaging. Depending on the power characteristics of the available source arrays, the geometry of the system may be modified to enable larger apertures 3305, 3307, and 3309 while still providing un-truncated projection measurements. At a given instant in time, radiation is emitted simultaneously from source array cells n, p and q referred to by numerals 3321, 3323, and 3325 respectively. The timing of the respective cells activation corresponds with the passage of respective detector apertures in front of the individual radiation cells in the array(s).

Figure 34A:
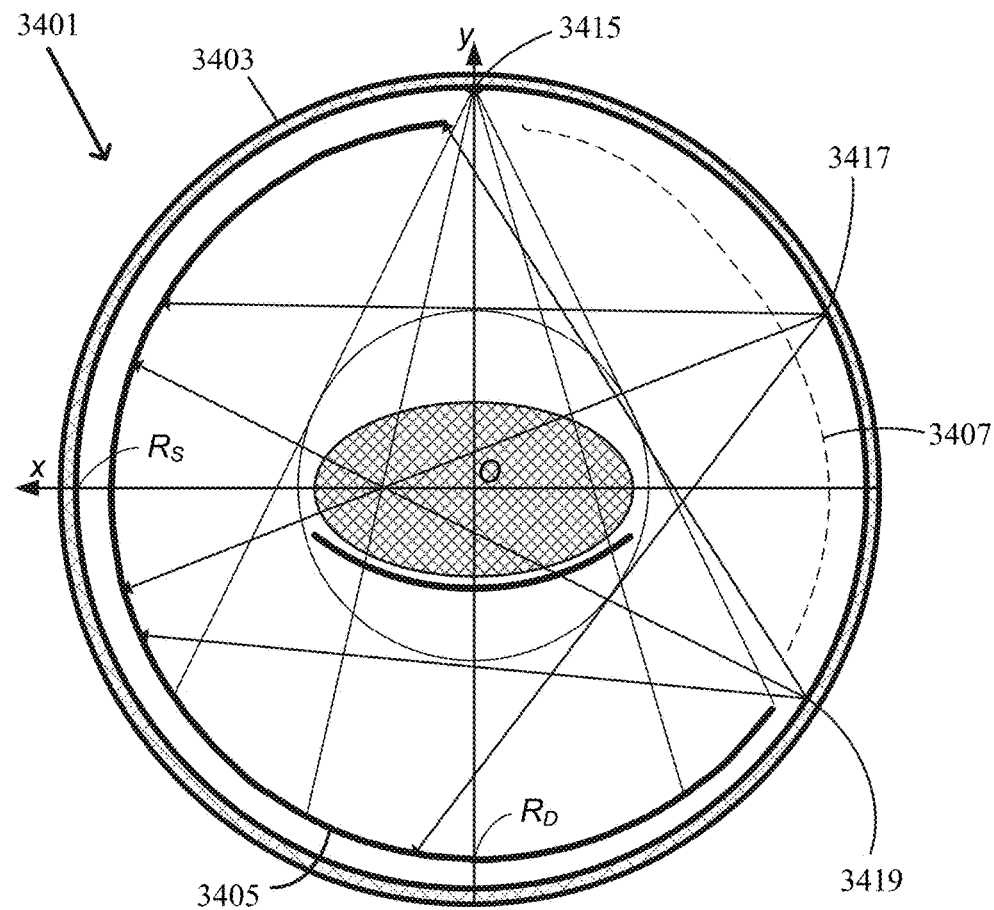
FIG. 34A and FIG. 34B present a CT system with a stationary array of x-ray sources, and a flying detector rotating within the stationary source gantry, and optimized for fast-imaging leveraging multiple simultaneous exposure by a multiplicity of x-ray sources.
Figure 34B:
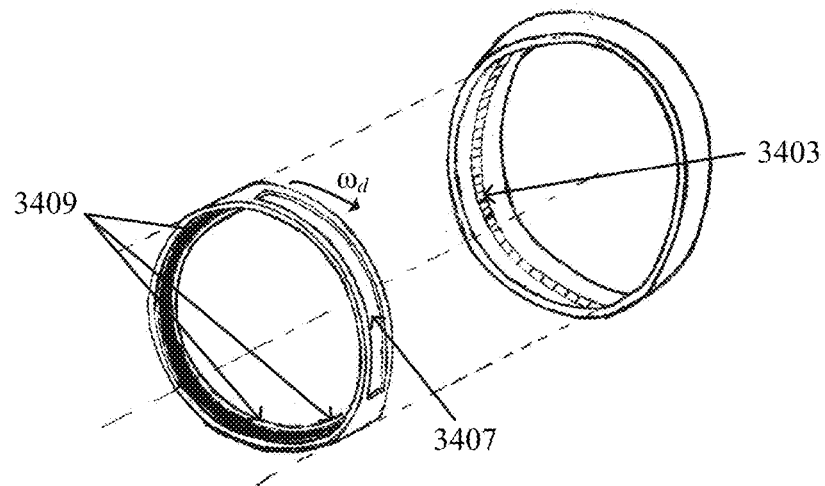

FIG. 34A and FIG. 34B present a CT system 3401 with a stationary array of x-ray sources 3403, and a flying detector 3405, rotating within the stationary source gantry 3401, and designed for fast-imaging leveraging multiple simultaneous exposure by a multiplicity of x-ray sources. The flying detector 3405 present an extended aperture indicated by dashed line 3407 of central angle designed such that the active and partially overlapping radiation sources are distributed over a central angle $\theta_s$ substantially equal to $(\pi-2\Gamma)$ radians at any instant in time during imaging; thereby allowing simultaneous exposure by a multiplicity of x-ray sources per the present invention. A significant advantage of this design is that the detector array may be made to rotate at much higher speeds than current gantries angular rotation speeds, leading to significant temporal resolution gains. Further, the number of simultaneously active sources partially overlapping on extended detector array 3409 can be selected as a function of the desired speed of examination, the amount of power and/or beam flux required for the selected object or patient to be imaged, and other parameters of CT imaging as known in the art. In an illustrative embodiment, FIG. 34A shows three simultaneously active and partially overlapping radiation sources 3415, 3417, and 3419. Under the two extreme sources separation condition described herein such that the projections associated with the two extreme sources in view of the detector 3415 and 3419 do not overlap on the detector, the pre-reconstruction inversion problem becomes solvable locally as described in this document.

Figure 35A:
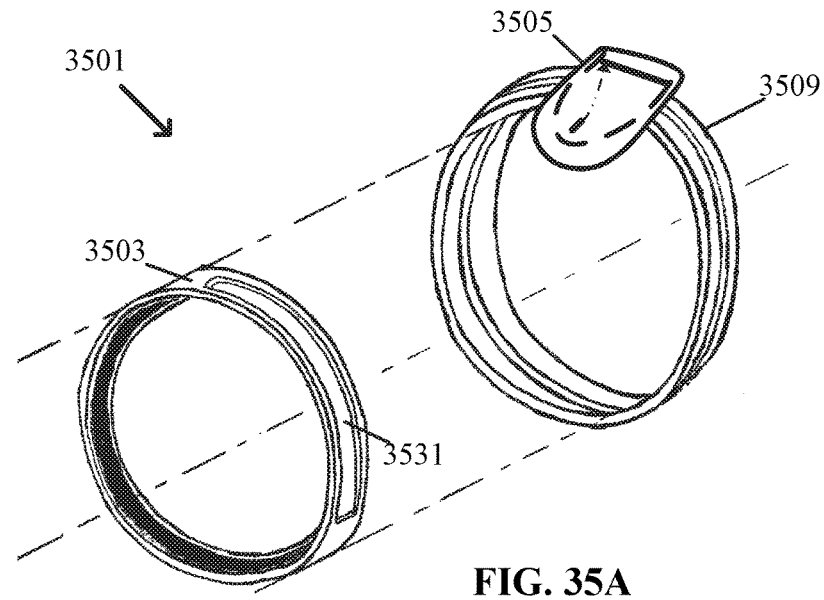
FIG. 35A and FIG. 35B shows a CT system with a flying detector rotating within a fixed gantry supporting a plurality of electron-beam x-ray sources (one illustrated).
Figure 35B:
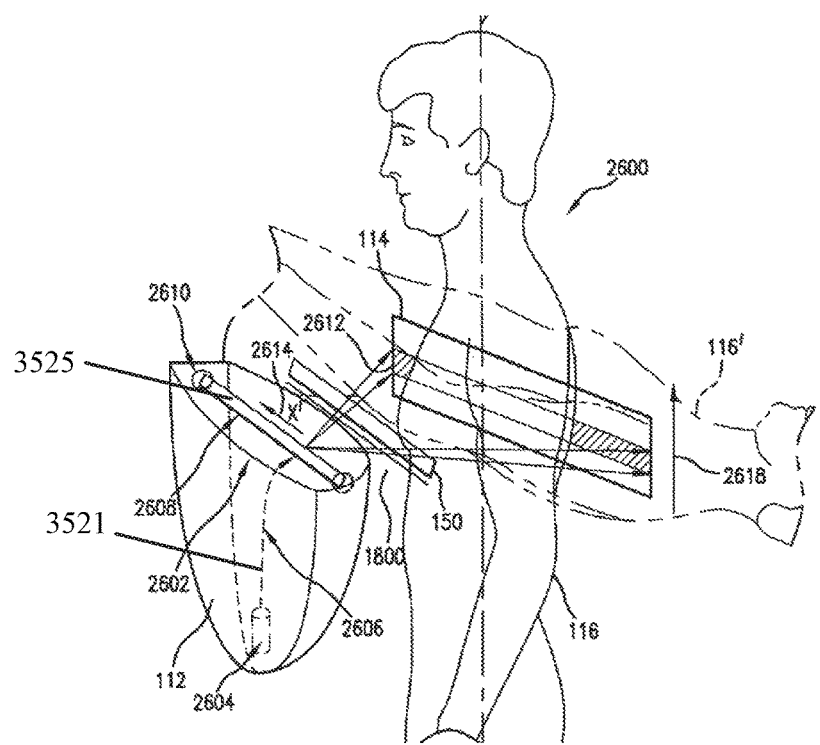

FIG. 35A presents an alternate embodiment of a CT system 3501 comprising a flying detector 3503, and a plurality of electron-beam sources 3505 (one shown) arranged on a fixed or rotating gantry 3509. Referring to FIG. 35B, the electron beam 3521 is swept across a target 3525, either stationary or rotating with respect to an axis, and the timing of the electron-beam sweep is made to coincide with the passage of the flying detector extended aperture 3531. The electron-beam source illustrated in FIG. 35A is from U.S. Pat. No. 6,973,158 "Multi-target x-ray tube for dynamic multi-spectral limited-angle CT imaging" issued to the author of the present disclosure.

Figure 36:
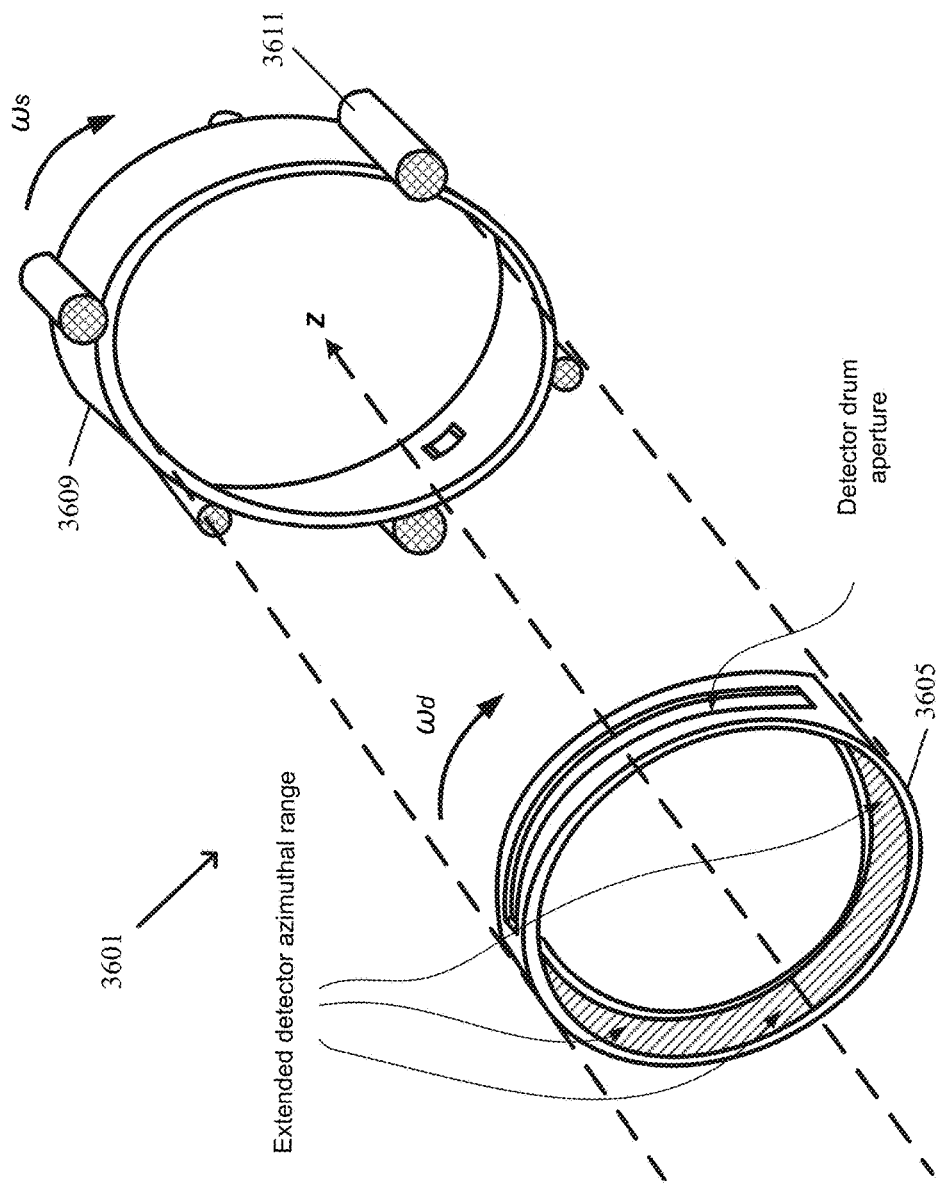
FIG. 36 presents a flying detector rotating within a rotating external gantry supporting a plurality of x-ray sources, in geometric dimensions optimized for the number of x-ray sources.

FIG. 36 presents an exploded perspective view of a CT system 3601 comprising a flying detector 3605, an external rotating gantry 3609 supporting $N_s$ sources 3611, in optimized geometric dimensions as described below.

In such a configuration, we consider a system with $N_s$ sources distributed over $2\pi$ radians; thus $$\Delta\theta_S = \frac{2\pi}{N_S}.$$

The narrowest active/visible source separation $\theta_s$ is achieved when $(\pi-=k\Delta\theta_s$; then: $\theta_s=(k-1)\Delta\theta_s$.

Writing:

$$g(\Gamma) = 2 a\sin\left(\frac{R_M}{R_d R_s} \times \left[R_S \cos(\Gamma) + \sqrt{R_d^2 - R_M^2}\right]\right),$$

the source separation condition for local system inversion becomes:

$\theta_S=(k-1)\Delta\theta_s \geq g(\Gamma)$; Thus we get the relationship:

$$(\pi - 2\Gamma) - \frac{2\pi}{N_S} \geq g(\Gamma); \text{ or } F(N_S, \Gamma) \geq 0.$$

In general, the functional F needs to be analyzed numerically. When $R_d \sim R_s$ these relationships become, with $g(\Gamma) \sim 4\Gamma$ and $6\Gamma < \pi$:

$$N_S \geq \frac{2\pi}{\pi - 6\Gamma}; \Gamma \leq \frac{\pi}{6} \frac{(N_S - 2)}{N_S}.$$

The last relationship enables a calculation of the minimum CT system dimension $R_s$ from the number of sources $N_s$; it constitutes more of a constraint for a relatively small number of sources:

| $N_S$ | $\Gamma$ (radians) | $R_S$(mm) |
|---|---|---|
| 6 | 0.35 | 730.95 |
| 9 | 0.41 | 631.19 |
| 12 | 0.44 | 591.55 |
| 24 | 0.48 | 541.42 |
| 36 | 0.49 | 526.76 |
| 100 | 0.51 | 509.26 |
| 600 | 0.52 | 501.52 |

This table applies with $$\Gamma = a\sin\left(\frac{R_M}{R_s}\right)$$

and for a system with $R_M$=250 mm.

Figure 37:
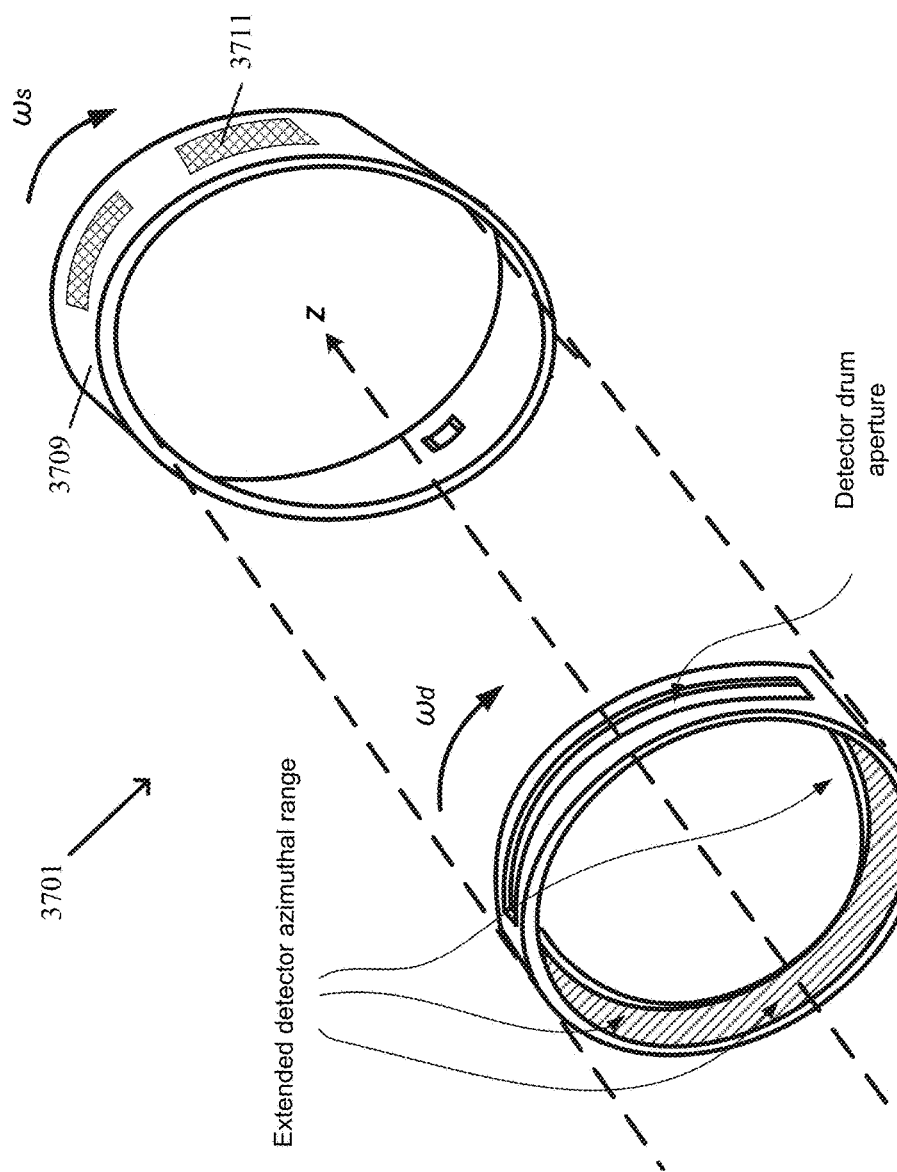
FIG. 37 shows a flying detector rotating within an external gantry supporting arrays of radiation sources.

The CT system illustrated in FIG. 37 is similar to the system of FIG. 36, except that the plurality of individual radiation sources 3611 is replaced with a plurality of radiation source arrays 3711 arranged on the external gantry 3709.

Figure 38A:
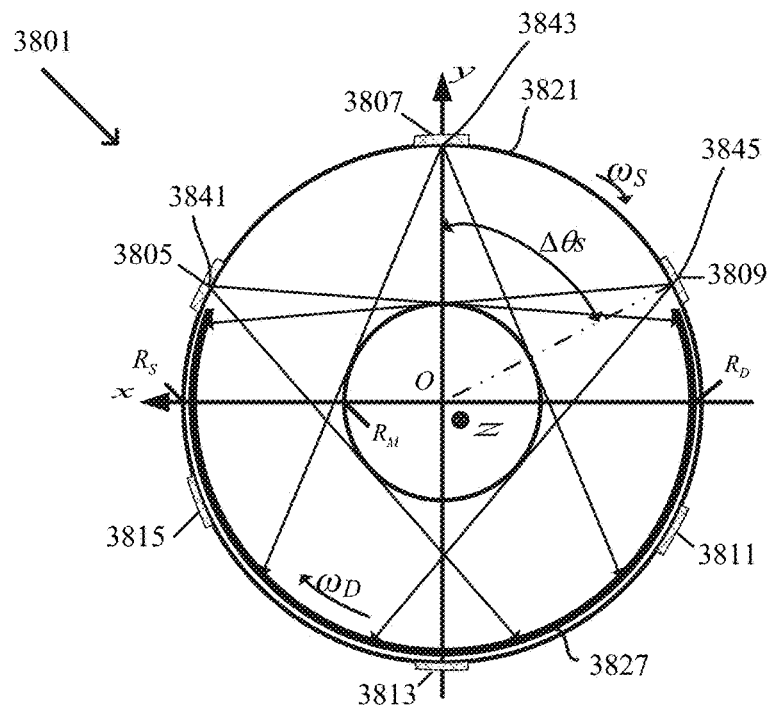
FIGS. 38A and 38B illustrate the use of source array timing sequences in a CT system with one rotating gantry and three radiation source arrays.
Figure 38B:
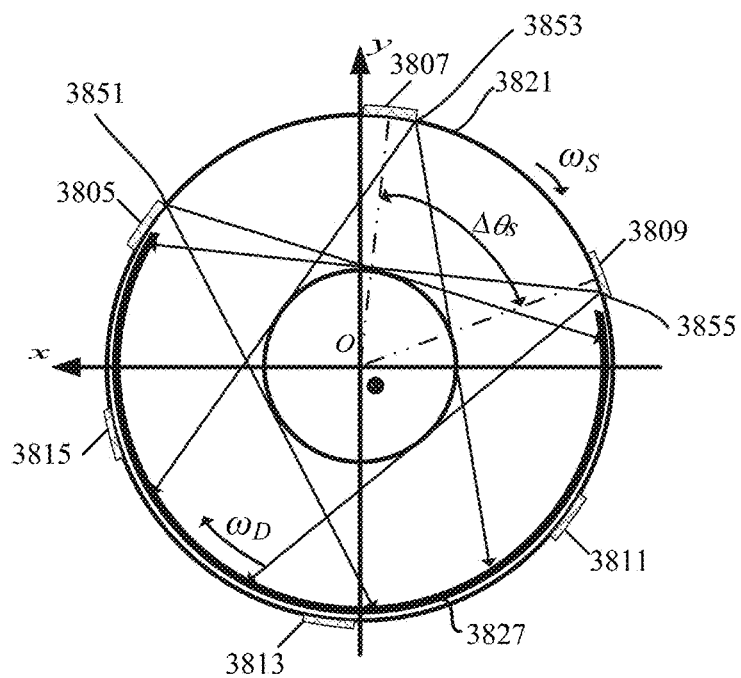

FIGS. 38A and 38B show a CT system 3801 as in FIG. 37 and further illustrate the use of timing sequences for the triggering of individual radiation sources within specific source arrays. In the embodiment pictured in FIG. 38A at time instant t, system 3801 has six separate radiation source arrays 3805, 3807, 3809, 3811, 3813, and 3815 distributed on the external rotating gantry 3821. In the source gantry and flying detector 3837 positions, three individual sources 3841, 3843, and 3845 respectively part of source arrays 3805, 3807 and 3809 are simultaneously active and partially overlapping on the detector. When extreme sources 3841 and 3845 satisfy the separation condition:

$$\theta_S(t) \geq 2 a \sin\left(\frac{R_M}{R_d R_s} \times \left[R_S \cos(\Gamma) + \sqrt{R_d^2 - R_M^2}\right]\right),$$

as shown in the figure, then their respective projections do not overlap on the detector and the pre-reconstruction inversion problem is locally invertible. This remains the case whether 3, 5, 11 or any larger number of individual source elements are simultaneously active, under the above extreme source separation condition.

In FIG. 38B, the respective gantries of system 3801 shown at a later instant in time t' have rotated. Now possibly different individual source elements 3851, 3853 and 3855 on source arrays 3805, 3807 and 3809 are simultaneously active and partially overlapping on the detector. The two extreme sources 3805 and 3809 define a new extreme angle $\theta_s'(t')$. As long as $\theta_s'(t')$ satisfies the separation condition above, the associated systems of equations are locally invertible.

Figure 39:
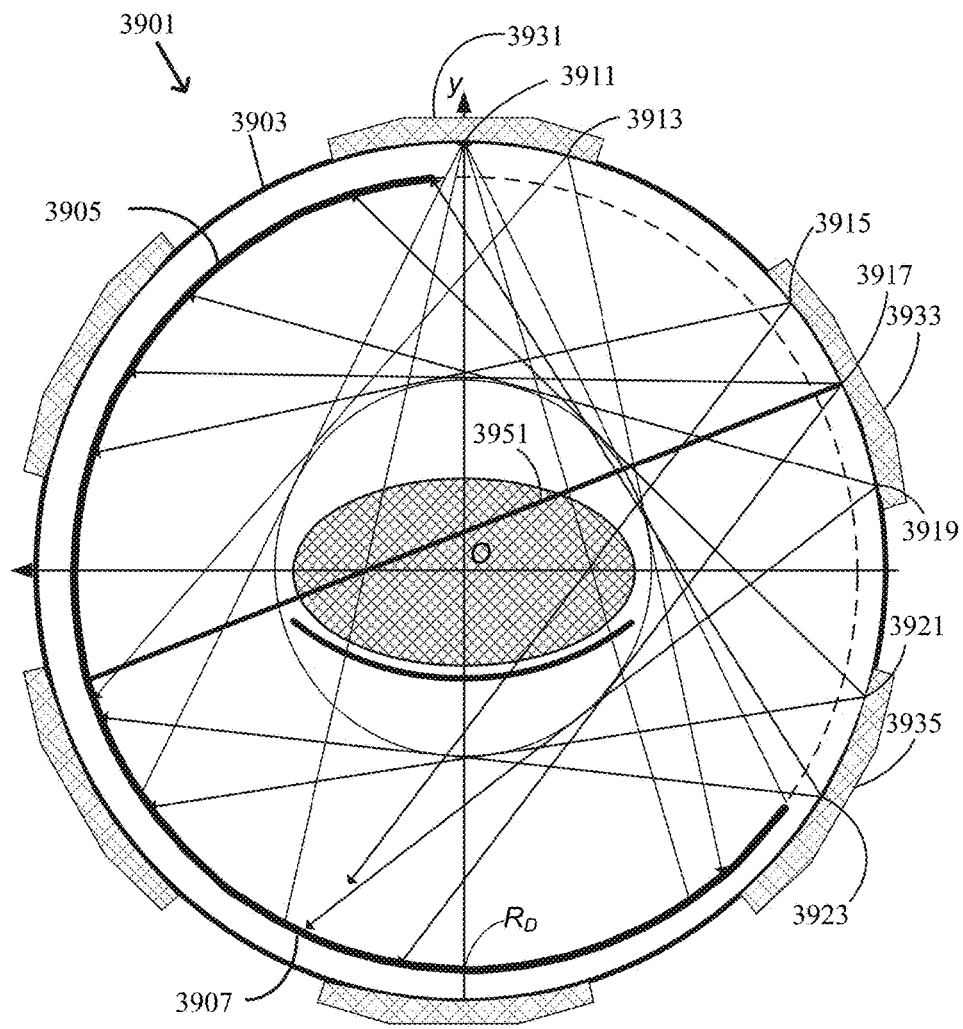
FIG. 39 presents a CT system with a flying detector and an external rotating gantry with multiple radiation source arrays.

FIG. 39 presents a planar cross-section for a CT system 3901 similar to the CT system 3701 of FIG. 37, and illustrates the timing of individual cell triggering within separate source arrays. It is noted that triggering is not necessarily limited to a single cell within a given array at a specific instant in time. In FIG. 39, CT imaging system 3901 has a rotating external source gantry 3903 and a rotating flying detector 3905. Source arrays 3931, 3933 and 3935 have simultaneously active radiation source elements 3911 and 3913 on source array 3931; elements 3915, 3917, and 3919 on source array 3933; and elements 3921 and 3923 on source array 3935. These seven individual source elements are in view of the flying detector 3905 and their respective projections partially overlap on the radiation detection surface 3907. Further, the two extreme sources 3911 and 3923 have projections that do not overlap on the detector; therefore, the L-bundle associated to a given line-integral L 3951 has seven summed measurements involving six individual line-integrals (including L), and an associated system of equations that has seven rows and six unknown; and it is locally invertible.

Figure 40A:
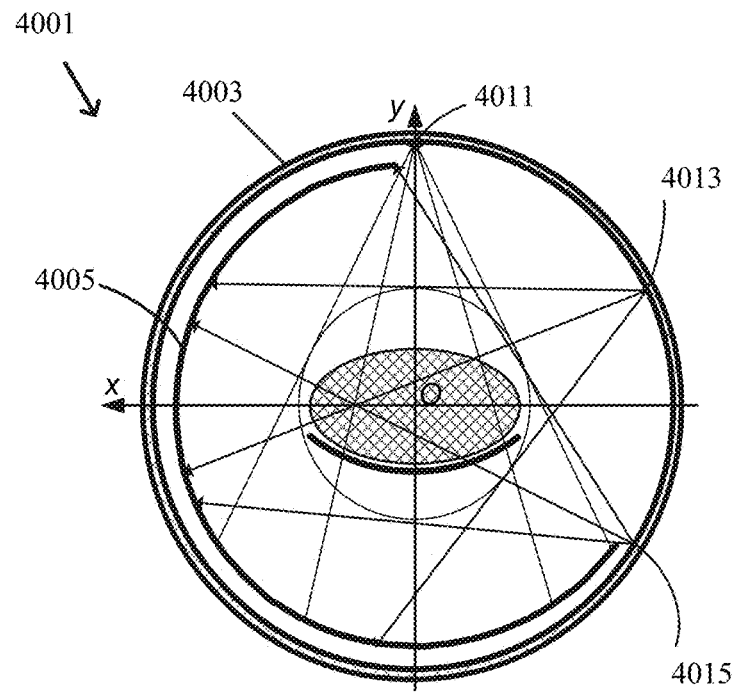
FIGS. 40A and 40B show a CT system with a flying detector and an external stationary gantry having multiple radiation source arrays substantially covering 360 degrees in central angle, and further illustrates the use of source timing sequences.

FIG. 40A presents a CT imaging system 4001 as in FIGS. 34A and 34B, and further illustrates the application of individual source triggering to a stationary source array substantially covering the entire stationary gantry interior surface. The system 4001 has non-rotating radiation source array(s) 4003 and a flying detector 4005. At the instant in time t illustrated in FIG. 40, three individual source elements 4011, 4013, and 4015 are simultaneously active, irradiating the object to be imaged, and partially overlapping on the flying detector 4005.

Figure 40B:
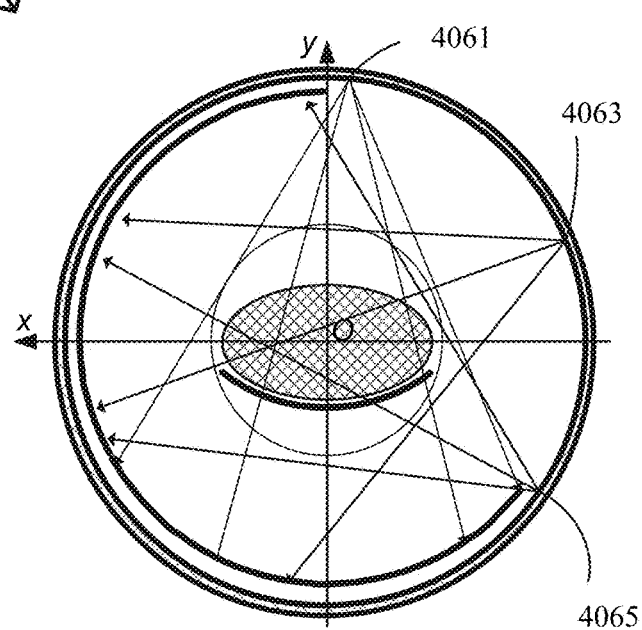

FIG. 40B presents the CT system 4001 at a different instant in time t', 4051, the flying detector having rotated with respect to the system rotation axis as compared to the position at time t. Now, individual radiation source elements within the array(s) 4061, 4063, and 4065 are simultaneously active, irradiating the object to be imaged, and partially overlapping on the flying detector.

Figure 41:
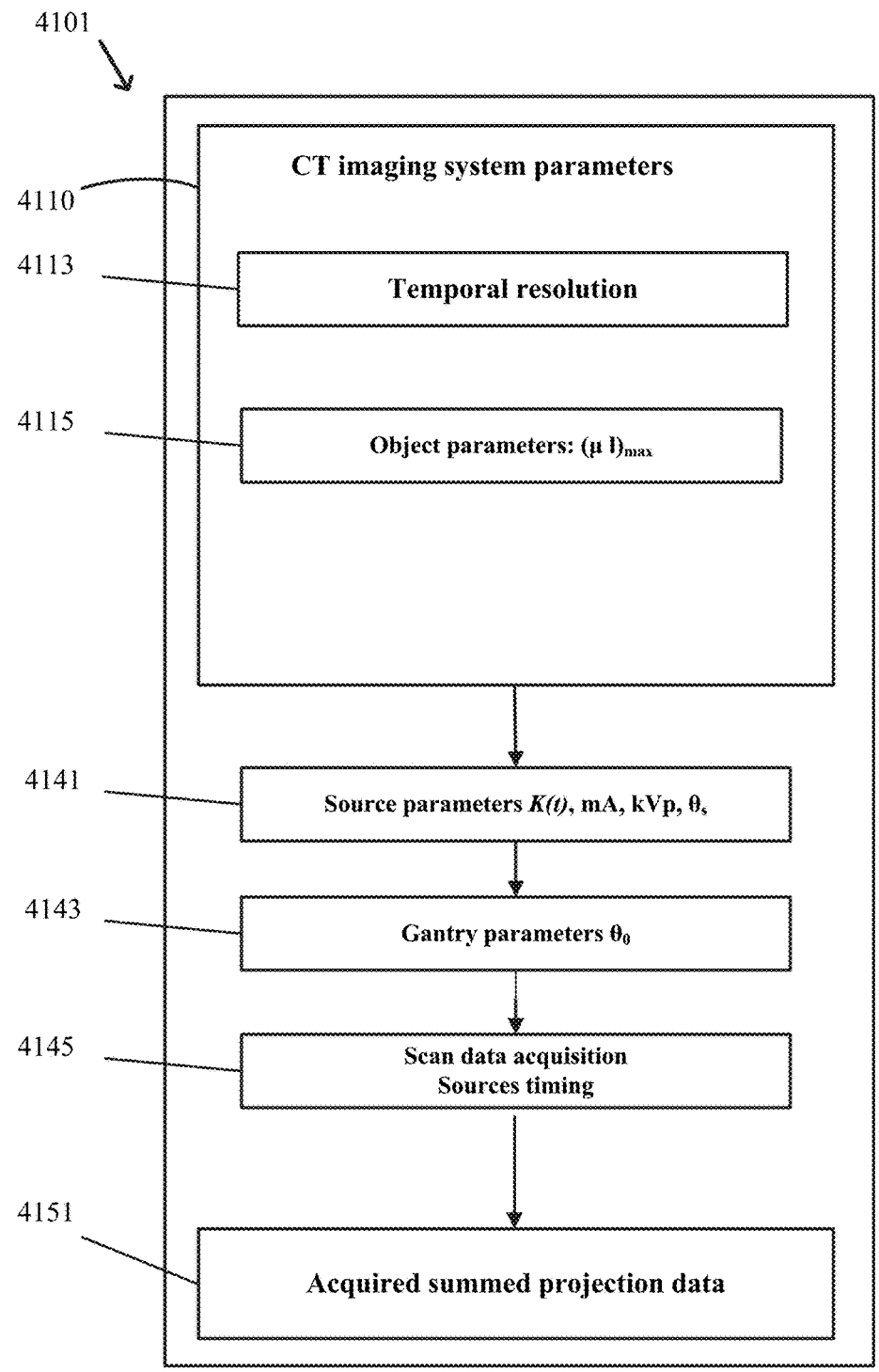
FIG. 41 presents a flowchart for a method to implement a source timing sequence on a system provided with a rotating detector and a set of radiation source arrays.

FIG. 41 presents a method 4101 of imaging for a CT system having array(s) of source elements, the individual source elements within the array(s) being individually controllable, whether or not the gantry supporting the source array(s) rotates. Given CT system parameters 4110 including geometry, number of sources, various specified distances, and the typical other specification parameters; and given inputs at 4113 regarding desired temporal resolution (normally guided by clinical considerations); and given 4115 object/patient a-priori information such as age, maximum line-integral attenuation (as typically obtained from a prior "scout" or "topogram" exam as known in the art), the method determines at 4141 for each instant t during a scan imaging sequence the number of radiation sources K(t) in view of the radiation detector and simultaneously active and radiating the patient/object of interest, the instantaneous extreme central angle, and the various source parameters such as beam intensity (mA) and peak-kilo-voltage (kVp) for each active source at each instant t.

The method also determines at 4143 the initial gantry angles $\theta_0$ as well as the various gantry velocities $\omega_S$ and $\omega_d$ for each time t. Based on this information, the method determines at 4145 the precise timing sequences for each individual source array to be activated during the scan. The scan sequence is then completed by the machine, and the method terminates at 4151 with the acquisition of summed projection data sufficient for image reconstruction over the volume of interest for this particular CT imaging scan.

In a CT systems with $N_s$ sources optimized for low-dose imaging, the detector aperture along the z-axis is relatively narrow, on the order of 10 to 20 mm, as measured on iso-center along the z-axis. The detector is made of a continuous direct conversion material, such as CZT (Cadmium Zinc Telluride) or CdTe, (Cadmium Telluride) as known in the art. The conversion material is sandwiched between two electrodes, and a bias voltage is applied; thus the individual detector cells are defined by the area of one of the two facing electrodes. With no ASG lamellas shadowing the entrance surface of the detector, geometric detection efficiency is nearly 100%; an about 30% increase in efficiency as compared to scintillator-based material. The narrow aperture is effective at rejecting scatters; optionally, two ASG lamellas are provided on both z-edges of the active detector area, to reduce the detection of scatter events at an angle with respect to the main imaging plane, x-y. Thus the systems and methods disclosed therein allow the trading of a large detector aperture along z for a significantly increased temporal resolution; thus enabling the acquisition of scan data with a 30% dose efficiency increase while retaining practical organ coverage speed. Such a CT system has applications in all area where radiation dose is a concern; and particularly for the CT imaging of pediatric patients.

The advantages of the above described apparatus embodiments, improvements, and methods should be readily apparent to one skilled in the art, as to enabling the design of computed tomography systems acquiring full sets of projection data and optimized for both speed of data acquisition and efficiency of design with respect to the number of radiation sources employed. Additional design considerations may be incorporated without departing from the spirit and scope of the invention. It should thus be noted that the matter contained in the above description and/or shown in the accompanying drawings should be interpreted as illustrative and not in a limiting sense. Accordingly, the following claims are intended to cover all generic and specific features described herein, as well as all statements of the scope of the present methods, and systems which, as a matter of language, might be said to fall there between.

The advantages of the above described apparatus embodiments, improvements, and methods should be readily apparent to one skilled in the art, as to enabling the design of computed tomography systems acquiring full sets of projection data and optimized for both speed of data acquisition and efficiency of design with respect to the number of radiation sources employed. Additional design considerations may be incorporated without departing from the spirit and scope of the invention. It should thus be noted that the matter contained in the above description and/or shown in the accompanying drawings should be interpreted as illustrative and not in a limiting sense. Accordingly, the following claims are intended to cover all generic and specific features described herein, as well as all statements of the scope of the present methods, and systems which, as a matter of language, might be said to fall therebetween.

What is claimed is:

1. A computed tomography (CT) imaging system comprising:
    a radiation detector array;
    a rotating gantry supporting a plurality $N_s$ of radiation sources, the radiation sources configured to project partially overlapping projections on the radiation detector array, the radiation sources configured to radiate simultaneously during at least part of imaging, the plurality of radiation sources including at least first and second extreme sources, the first and second extreme sources defining a central angle $\theta_s$ between them and other radiation sources of the plurality of radiation sources are between the first and second extreme sources;
    wherein the central angle $\theta_s$ is less than $\pi$ radians and sufficiently large that the respective projections of radiation from the two extreme sources do not overlap each other on the radiation detector array;
    at least two of the radiation sources producing partially overlapping projections on the radiation detector array; and
    a processor coupled to receive data from the radiation detector array and having a memory, the memory containing firmware for performing a pre-reconstruction inversion process on the data from the radiation detector array.

2. The CT imaging system of claim 1, wherein the firmware for performing a pre-reconstruction inversion process partitions the data from the radiation detector into L-bundles related to specific line-integrals L, applying knowledge of the projections to construct a linear system; and
    wherein the firmware for performing a pre-reconstruction inversion process inverts the linear system to produce line integral data representing individual contributions of each radiation source at each element of the radiation detector array.

3. The CT imaging system of claim 2, further comprising CT image reconstruction firmware in the memory, the CT image reconstruction firmware adapted to derive a plurality of CT images from the data representing individual contributions of each radiation source at each element of the radiation detector array.

4. The system of claim 3 wherein the system has an imaging-field-of-view centered on an axis of rotation of the gantry and of radius $R_M$ as measured from the rotation axis, the radiation sources being at a minimum distance $R_S$ from the rotation axis, and each radiation source has fan-angle $\Gamma$ sufficient to illuminate the field of view,
    wherein the central angle $\theta_s$ is less than $\pi$ radians minus a system fan angle $\Gamma$ representing a maximum of the fan-angles of the radiation sources.

5. The CT imaging system of claim 4 wherein the central angle $\theta_s$ is equal to or less than $\pi$ radians minus twice the system fan-angle.

6. The CT imaging system of claim 4, wherein substantially $$\Gamma = \arcsine\left(\frac{R_M}{R_S}\right)$$

and $\theta_s \leq \pi - 2\Gamma$ radians.

7. The CT imaging system of claim 4 further defining a detector distance $R_d$, wherein substantially $$\theta_S \geq 2\arcsine\left(\frac{R_M}{R_d R_s} \times \left[R_S \cosine(\Gamma) + \sqrt{R_d^2 - R_M^2}\right]\right).$$

8. The CT imaging system of claim 4 for $N_s$=3 or 4 in an optimized geometry, wherein:
    the system has an imaging-field-of-view centered on the rotation axis and of radius $R_M$ as measured from the rotation axis, the radiation sources being at a minimum distance $R_S$ from the rotation axis;
    the system fan-angle $\Gamma$ is approximately $$\Gamma = \arcsine\left(\frac{R_M}{R_s}\right);$$

and
    wherein substantially $$\theta_s = (2\Gamma + \pi) \times \frac{(N_s - 1)}{N_s}.$$

9. The CT imaging system of claim 2, wherein each radiation source comprises a pair of adjacent radiation emitters operable at different energies.

10. The CT imaging system of claim 4, wherein the radiation detector is mounted on the rotating gantry.

11. The CT imaging system of claim 4, the rotating gantry defining a main plane of rotation, wherein at least one of the $N_s$ radiation sources are offset along the rotation axis with respect to another radiation source of the radiation sources.

12. The CT imaging system of claim 2, wherein the radiation sources are provided as arrays of individually controllable radiation sources and wherein individual source elements in the source arrays can be activated in sequence.

13. The CT imaging system of claim 2, wherein the radiation detector is mounted on the rotating gantry.

14. The CT imaging system of claim 2, wherein at least part of the radiation detector is fixed to a frame within which the gantry rotates.

15. The CT imaging system of claim 1, the rotating gantry defining a main plane of rotation, wherein at least one of the $N_s$ radiation sources are offset along the rotation axis with respect to another radiation source of the radiation sources.

16. The CT imaging system of claim 1, wherein the radiation detector array is divided into a fixed component and a rotating component mounted on the rotating gantry.

17. The CT imaging system of claim 16 wherein the rotating component of the radiation detector array has an opening aligned to permit radiation to pass through the opening onto the fixed component of the radiation detector array.

18. The CT imaging system of claim 1, wherein the radiation detector array and the plurality of radiation sources are located at a same distance from an axis of rotation of the rotating gantry.

19. The CT imaging of claim 1, wherein the central angle between any two adjacent radiation sources is substantially equal to an integer multiple of the central angle between two adjacent projections as acquired by the system during imaging.

20. A method of performing a computed tomography (CT) scan of an object in an imaging zone, comprising:
providing a plurality of radiation sources, each radiation source directed at an imaging zone;
providing a radiation detector array disposed to receive radiation projected through the field of view by the radiation sources;
wherein the radiation projected by a first source of the plurality of radiation sources overlaps on the detector array at least in part radiation projected by a second source of the plurality of radiation sources;
enabling the plurality of radiation sources of the radiation detector array;
measuring radiation received by elements of the radiation detector array through the detector integration time as a set of measurements; and
recovering estimates of individual line integrals, recovering further comprising:
partitioning the set of measurements into a set of summed line-integrals partitioned into sub-sets; and inverting a linear system associated to each subset to provide individual line integral data.

21. The method of claim 20 further comprising reconstructing at least one tomographic slice of the object.

22. The method of claim 21 wherein the recovering comprises inverting a linear system wherein the unknowns are given by the exponentials of the negative of the line-integral terms.

23. The method of claim 22, wherein the linear system comprises K or fewer rows and the number of unknown is less than the number of rows, where K is the number of active sources contributing to the measurements in a given partitioned set.

24. A computed tomography (CT) imaging system comprising:
a stationary gantry with a plurality $N_s$ of partially overlapping radiation sources;
a flying detector array with an extended aperture and a radiation detector array,
a controller coupled to control motion of the detector array and operation of the overlapping radiation sources, the controller configured to define an instant of time t wherein a plurality greater than or equal to two of K active radiation sources of the partially overlapping radiation sources are in view of the detector and configured to simultaneously irradiate the detector array with overlapping radiation projections on the detector array, the at least two active radiation sources comprising two extreme radiation sources in view of the detector array at instant t;
wherein the two extreme radiation sources in view of the radiation detector at time t define a central angle $\theta s$ such that the respective projections of the two extreme sources do not overlap on the detector array.

25. The CT imaging system of claim 24 wherein the plurality greater than or equal to two of K active radiation sources is greater than or equal to three.

26. The CT imaging system of claim 24, further comprising an image processor having a memory, image processor coupled to receive data from the radiation detector array, the memory containing firmware for performing a pre-reconstruction inversion process on the data received from the radiation detector and create therefrom data comprising line integrals from each radiation source to each element of the radiation detector array.

27. The CT imaging system of claim 26, wherein the firmware for performing a pre-reconstruction inversion process is configured to select a set of line integrals necessary for reconstruction of a CT image and partitions the set of measurements into L-bundles related to specific line-integrals L, and to construct a linear system of equations therefrom.

28. The CT imaging system of claim 27, wherein the firmware for performing a pre-reconstruction inversion process inverts the linear system of equations to produce a system of line integrals L.

29. The CT imaging system of claim 28 further comprising image reconstruction firmware adapted to construct at least one tomographic image from the line integrals L.

30. The CT imaging system of claim 24, wherein the radiation detector array substantially extends over a central angle sufficient for the detector to obtain non-truncated projection measurements for all K active sources in view of the radiation detector array.

31. The CT imaging system of claim 24 having
an imaging-field-of-view centered on a rotation axis of the rotating gantry of radius $R_M$ as measured from the rotation axis;
a distance $R_S$ from the rotation axis defining a minimum distance from the rotation axis for the radiation sources;
a system fan-angle $\Gamma$ defined as a function of $R_S$ and $R_M$;
wherein the system fan-angle $\Gamma$ is given by $\Gamma$=arcsine $(R_M/R_S)$, and substantially $\theta_s \leq \pi - 2\Gamma$ radians.

32. The CT imaging system of claim 31 further defining a detector distance $R_d$ from an axis of rotation of the flying detector, and where the system fan-angle $\Gamma$ is given by $\Gamma$=arcsine $(R_M/R_S)$;
wherein:

$$2 \arcsine\left(\frac{R_M}{R_d R_s} \times \left[R_s \cosine(\Gamma) + \sqrt{R_d^2 - R_M^2}\right]\right) \leq \theta_s \leq \pi - 2\Gamma.$$

33. The CT imaging system of claim 24 wherein the radiation sources are provided as arrays of individually controllable radiation emitters.

34. The CT imaging system of claim 24 wherein the radiation sources are provided as a plurality of electron-beam radiation sources, wherein an electron beam can be swept laterally within an extended vacuum envelope to move a point of emission of x-ray radiation.

35. The CT system of claim 24, wherein the central angle between any two adjacent active radiation sources is substantially equal to an integer multiple of the central angle between two adjacent projections as acquired by the system during imaging.

36. A computed tomography (CT) imaging system comprising:
a rotating source gantry with a plurality $N_s$ of partially overlapping radiation sources mounted thereon, the rotating source gantry configured to rotate around a rotation axis;
a flying detector gantry with an extended aperture and a radiation detector array, the rotating gantries configured such that at a particular instant in time t a plurality K≥2 of active radiation sources are in view of the detector, a subset of the plurality K of active radiation sources simultaneously irradiating during at least part of imaging, the subset further defining two extreme radiation sources in view of the detector at instant t, the flying detector gantry configured to rotate about the rotation axis; an image processor coupled to receive data from the radiation detector array and having a memory, the memory containing firmware adapted to perform a pre-reconstruction inversion process;
wherein two of the partially overlapping radiation sources are extreme radiation sources in view of the detector at time t and define a central angle $\theta_s$ such that the respective projections of the two extreme sources do not overlap on the detector.

37. The CT imaging system of claim 36, wherein the firmware for performing a pre-reconstruction inversion process selects a set of summed measurements necessary for reconstruction of a CT image and partitions the set of measurements into L-bundles related to specific line-integrals L, and inverts a linear system of equations with as many or fewer rows than K and as many or fewer unknowns than rows, the linear system of equations derived from the L-bundles.

38. The CT imaging system of claim 37, wherein the radiation detector substantially extends over a central angle sufficient for non-truncated projection measurements from K of the plurality of radiation sources in view of the detector.

39. The CT imaging system of claim 38 wherein an imaging-field-of-view is centered on the rotation axis, the field of view being of radius $R_M$ as measured from the rotation axis;
wherein the radiation sources are located at a minimum distance $R_S$ from the rotation axis;
a system fan-angle $\Gamma$ is defined as $$\Gamma = \text{arcsine}\left(\frac{R_M}{R_s}\right),$$

and substantially $\theta_s \leq \pi - 2\Gamma$ radians.

40. The CT imaging system of claim 39, further defining a detector distance $R_d$, wherein substantially $$\theta_s \geq 2 \text{ arcsine}\left(\frac{R_M}{R_d R_s} \times \left[R_s \text{cosine}(\Gamma) + \sqrt{R_d^2 - R_M^2}\right]\right).$$

41. The CT imaging system of claim 39 wherein $$\Gamma \leq \frac{\pi}{6} \times \frac{(N_s - 2)}{N_s}.$$

42. The CT imaging system of claim 36, wherein the central angle between any two adjacent sources is substantially equal to an integer multiple of the central angle between two adjacent projections as acquired by the system during imaging.

43. A computed tomography (CT) system having an imaging-field-of-view centered on a rotation axis of radius $R_M$, the system comprising:
a rotating gantry supporting two radiation sources at a minimum distance $R_S$ from the rotation axis and separated by a central angle $\Delta\theta_s$;
a system fan-angle $\Gamma$ given by $\Gamma = \text{arcsine } (R_M/R_S)$;
wherein the central angle between the sources is substantially equal to $\Delta\theta_s = \pi/2 + \Gamma$.

44. The CT system of claim 43, wherein each radiation source has at least two radiation emitters operable at different energies.

45. A CT system in an optimized geometry having an imaging-field-of-view centered on a rotation axis and of radius $R_M$ as measured from the rotation axis; the system comprising:
a rotating gantry supporting two radiation sources located at a minimum distance $R_S$ from the rotation axis and separated by a central angle $\Delta\theta_s$;
the system having a system fan-angle $\Gamma$ given by $$\Gamma = \text{arcsine}\left(\frac{R_M}{R_s}\right);$$

wherein substantially $$\Gamma = \frac{\pi}{6}$$

and the central angle between the two radiation sources is substantially:

$$\Delta\theta_s = \pi - 2\Gamma = \frac{2\pi}{3}.$$

46. The system of claim 45, wherein each radiation source is a pair of adjacent radiation emitters operable at different energies.

47. A CT system in an optimized geometry having an imaging-field-of-view of centered on a rotation axis and of radius $R_M$ as measured from the rotation axis; the system comprising:
a rotating gantry supporting three radiation sources at a minimum distance $R_S$ from the rotation axis and defining two extreme radiation sources separated by a central angle $\theta_s$;
a system fan-angle $\Gamma$ given by $$\Gamma = \text{arcsine}\left(\frac{R_M}{R_s}\right);$$

wherein substantially $$\Gamma = \frac{\pi}{10}$$

and the central angle between the two extreme radiation sources is substantially:

$$\theta_s = \pi - 2\Gamma = \frac{4\pi}{5}.$$

48. The system of claim 47, wherein the three radiation sources are equispaced, and the central angle between two adjacent radiation sources $\Delta\theta_s$ is substantially equal to:

$$\Delta\theta_s = \frac{\pi - 2\Gamma}{2} = \frac{2\pi}{5}.$$

49. The system of claim 47, wherein each radiation source is replaced by a pair of adjacent radiation sources operating at different energies.

50. A CT system in an optimized geometry having an imaging-field-of-view centered on a rotation axis and of radius $R_M$ as measured from the rotation axis;

a rotating gantry supporting five radiation sources at a minimum distance $R_S$ from the rotation axis, and configured to rotate about the rotation axis;

a system fan-angle $\Gamma$ given by $$\Gamma = \arcsine\left(\frac{R_M}{R_s}\right);$$

wherein substantially $$\Gamma = \frac{\pi}{10}$$

and the radiation sources are substantially equispaced over a central angle equal to $2\pi$.

* * * * *